US012680103B2

(12) United States Patent
Thompson

(10) Patent No.: US 12,680,103 B2
(45) Date of Patent: Jul. 14, 2026

(54) COMPOSITION FOR REGULATING PRODUCTION OF INTERFERING RIBONUCLEIC ACID

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 0 days.

(21) Appl. No.: 19/271,317

(22) Filed: Jul. 16, 2025

(65) Prior Publication Data

US 2025/0340889 A1      Nov. 6, 2025

Related U.S. Application Data

(60) Continuation of application No. 18/968,659, filed on Dec. 4, 2024, now Pat. No. 12,540,329, which is a division of application No. 18/582,272, filed on Feb. 20, 2024, now Pat. No. 12,522,831.

(51) Int. Cl.
*C12N 15/113*          (2010.01)
*C12N 15/86*          (2006.01)

(52) U.S. Cl.
CPC .......... *C12N 15/1138* (2013.01); *C12N 15/86* (2013.01); *C12N 2310/141* (2013.01); *C12N 2750/14143* (2013.01)

(58) Field of Classification Search
CPC .................. C12N 15/86; C12N 15/111; C12N 2310/141; C12N 2750/14141; C12N 15/1138; C12N 2750/14143
See application file for complete search history.

(56) References Cited

U.S. PATENT DOCUMENTS

| | | | |
|---|---|---|---|
| 11,085,055 B2 | 8/2021 | Mallol et al. | |
| 11,162,102 B2 | 11/2021 | Minshull et al. | |
| 11,530,423 B1 | 12/2022 | Thompson | |
| 11,873,505 B2 | 1/2024 | Thompson | |
| 12,018,274 B2 | 6/2024 | Thompson | |
| 12,134,770 B1 * | 11/2024 | Thompson ............. | C12N 15/86 |
| 12,195,747 B1 | 1/2025 | Thompson | |
| 12,281,309 B1 | 4/2025 | Thompson | |
| 2016/0304869 A1 | 10/2016 | Maclean et al. | |
| 2024/0026377 A1 | 1/2024 | Thompson | |

FOREIGN PATENT DOCUMENTS

| | | | |
|---|---|---|---|
| CA | 2721333 A1 | 10/2009 | |

OTHER PUBLICATIONS

Homo sapiens 5HT1b, mRNA, NCBI Reference Sequence NM_000863. 3_HTR1B, version Feb. 2024, 9 pages, retrieved from the internet Mar. 24, 2025 (Year: 2024).*

O'Brien et al. "Overview of microRNA biogenesis, mechanisms of actions, and circulation." Frontiers in endocrinology 9 (2018): 402.

Bofill-De Ros et al. "Guidelines for the optimal design of miRNA-based shRNAs." Methods 103 (2016): 157-166.

Denzler et al. "Impact of microRNA levels, target-site complementarity, and cooperativity on competing endogenous RNA-regulated gene expression." Molecular cell 64.3 (2016): 565-579.

Van Den Berg et al. "Design of effective primary microRNA mimics with different basal stem conformations." Molecular Therapy Nucleic Acids 5 (2016).

Nature (2010. Gene Expression. Scitable. Available online at Nature. com) <https://www.nature.com/scitable/topicpage/gene-expression-14121669> (2010).

Tritschler et al. "Concepts and limitations for learning developmental trajectories from single cell genomics." Development 146.12 (2019): dev170506.

Ying et al. "The microRNA (miRNA): overview of the RNA genes that modulate gene function." Molecular biotechnology 38 (2008): 257-268.

Lam et al. "siRNA versus miRNA as therapeutics for gene silencing." Molecular therapy Nucleic acids 4 (2015).

Zuo et al. "5—Hydroxytryptamine receptor 1D aggravates hepatocellular carcinoma progression through Fox06 in AKT—dependent and independent manners." Hepatology 69.5 (2019): 2031-2047.

Volpicelli et al. "The micro RNA-29A modulates 5-HTR7 expression and its morphogenic effects in hippocampal neurons." (2019).

Yang et al. "Expression of mRNA for multiple serotonin (5-HT) receptor types/subtypes by the peripheral blood mononuclear cells of rhesus macaques." Journal of neuroimmunology 178.1-2 (2006): 24-29.

Gorski et al. "RNA-based recognition and targeting: sowing the seeds of specificity." Nature Reviews Molecular Cell Biology 18.4 (2017): 215-228.

Millan, Mark J. "MicroRNA in the regulation and expression of serotonergic transmission in the brain and other tissues." Current opinion in pharmacology 11.1 (2011): 11-22.

Le François et al. "A novel alternative splicing mechanism that enhances human 5-HT1A receptor RNA stability is altered in major depression." Journal of Neuroscience 38.38 (2018): 8200-8210.

(Continued)

*Primary Examiner* — Catherine Konopka
*Assistant Examiner* — Shabana S Meyering
(74) *Attorney, Agent, or Firm* — Gowling WLG (Canada) LLP

(57)          ABSTRACT

Some embodiments of the present disclosure relate to one or more compositions that upregulate the production of one or more sequences of micro-interfering ribonucleic acid (miRNA). The sequences of miRNA may be complementary to a sequence of target messenger RNA (mRNA) that encodes for translation of a target biomolecule and the miRNA can cause the target mRNA to be degraded or inactivated, thereby causing a decrease in bioavailability of the target biomolecule because it is degraded or inactivated by the miRNA, thereby decreasing the bioavailability of the target biomolecule within a subject that is administered the one or more compositions. In some embodiments of the present disclosure, the target biomolecule is a serotonin receptor, such as serotonin receptor 5HT1a, 5HT1b, 5HT1d, 5HT1e, 5HT1f, 5HT2a, 5HT2b, 5HT2c, 5HT3, 5HT4, 5HT6, or 5HT7.

2 Claims, No Drawings

Specification includes a Sequence Listing.

(56) References Cited

OTHER PUBLICATIONS

*Homo sapiens* 5ht1a, mRNA, NCBI Reference Sequence NM (2024).

*Homo sapiens* 5HTR7, mRNA, NCBI Reference Sequence (2024).

Bottoni et al. "Targeting BTK through microRNA in chronic lymphocytic leukemia." Blood, The Journal of the American Society of Hematology 128.26 (2016): 3101-3112.

Brutons Tyrosine Kinase Genbank Sequence (2023).

Christensen et al. "Recombinant adeno-associated virus-mediated microRNA delivery into the postnatal mouse brain reveals a role for miR-134 in dendritogenesis in vivo." Frontiers in neural circuits 3 (2010): 848.

GenBank EGF Sequence (2023).

Ahmadzadeh et al. "BRAF mutation in hairy cell leukemia." Oncology reviews 8.2 (2014): 253.

Patton et al. "Biogenesis, delivery, and function of extracellular RNA." Journal of extracellular vesicles 4.1 (2015): 27494.

Clark et al. "Detection of BRAF splicing variants in plasma-derived cell-free nucleic acids and extracellular vesicles of melanoma patients failing targeted therapy therapies." Oncotarget 11.44 (2020): 4016.

NCBI search results for SEQ ID No. 5 (2024).

NCBI Nucleotide Sequence ALK Lingand, search performed Dec. 26, 2024 (2023).

NCBI Nucleotide Sequence ALK Receptor, search performed Dec. 26, 2024 (2023).

GenBank EGFR Sequence (2023).

Genbank FLT3 Sequence 2024.

NCBI Nucleotide Sequence for PARP, search performed Dec. 26, 2024 (2024).

Kondratov et al. "Direct head-to-head evaluation of recombinant adeno-associated viral vectors manufactured in human versus insect cells." Molecular Therapy 25.12 (2017): 2661-2675.

Wang et al. "Adeno-associated virus vector as a platform for gene therapy delivery". Nat Rev Drug Discov. May 2019; 18(5):358-378. (Year: 2019).

* cited by examiner

COMPOSITION FOR REGULATING PRODUCTION OF INTERFERING RIBONUCLEIC ACID

CROSS REFERENCE TO RELATED APPLICATION

The present application is a continuation of U.S. patent application Ser. No. 18/968,659 filed Dec. 4, 2024, entitled "COMPOSITION FOR REGULATING PRODUCTION OF INTERFERING RIBONUCLEIC ACID" currently pending, which is a division of U.S. patent application Ser. No. 18/582,272 filed Feb. 20, 2024, entitled "COMPOSITION FOR REGULATING PRODUCTION OF INTERFERING RIBONUCLEIC ACID" currently pending, the entirety of which are incorporated herein by reference.

SEQUENCE LISTING

This application contains a Sequence Listing electronically submitted via Patent Center to the United States Patent and Trademark Office as an XML Document file entitled "A8149441US-Sequence Listing.xml" created on 2024-02-12 and having a size of 110,545 bytes. The information contained in the Sequence Listing is incorporated by reference herein.

TECHNICAL FIELD

The present disclosure generally relates to compositions for regulating production of interfering ribonucleic acid (RNA). In particular, the present disclosure relates to compositions for regulating gene expression and therefore, the production of interfering RNA, that will suppress serotonin receptor expression.

BACKGROUND

Bioactive molecules, including complements and factors, are necessary for the homeostatic control of biological systems.

When bioactive molecules are over-expressed, under-expressed or mis-expressed, homeostasis is lost, and disease is often the result.

As such, it may be desirable to establish therapies, treatments and/or interventions that address when homeostasis and regulation of bioactive molecules is lost to prevent or treat the resulting disease.

SUMMARY

Some embodiments of the present disclosure relate to one or more compositions that upregulate the production of one or more sequences of micro-interfering ribonucleic acid (miRNA). The sequences of miRNA may be complementary to a sequence of target messenger RNA (mRNA) that encodes for translation of a target biomolecule and the miRNA can cause the target mRNA to be degraded or inactivated, thereby causing a decrease in bioavailability of the target biomolecule because it is degraded or inactivated by the miRNA, thereby decreasing the bioavailability of the target biomolecule within a subject that is administered the one or more compositions. In some embodiments of the present disclosure, the target biomolecule is a serotonin receptor. In some embodiments of the present disclosure, the target biomolecule is a serotonin receptor such as serotonin receptor 5HT1a. In some embodiments of the present disclosure, the target biomolecule is a serotonin receptor such as serotonin receptor 5HT1b. In some embodiments of the present disclosure, the target biomolecule is a serotonin receptor such as serotonin receptor 5HT1c. In some embodiments of the present disclosure, the target biomolecule is a serotonin receptor such as serotonin receptor 5HT1d. In some embodiments of the present disclosure, the target biomolecule is a serotonin receptor such as serotonin receptor 5HT1e. In some embodiments of the present disclosure, the target biomolecule is a serotonin receptor such as serotonin receptor 5HT1f. In some embodiments of the present disclosure, the target biomolecule is a serotonin receptor such as serotonin receptor 5HT2a. In some embodiments of the present disclosure, the target biomolecule is a serotonin receptor such as serotonin receptor 5HT2b. In some embodiments of the present disclosure, the target biomolecule is a serotonin receptor such as serotonin receptor 5HT2c. In some embodiments of the present disclosure, the target biomolecule is a serotonin receptor such as serotonin receptor 5HT3. In some embodiments of the present disclosure, the target biomolecule is a serotonin receptor such as serotonin receptor 5HT4. In some embodiments of the present disclosure, the target biomolecule is a serotonin receptor such as serotonin receptor 5HT6. In some embodiments of the present disclosure, the target biomolecule is a serotonin receptor such as serotonin receptor 5HT7.

In some embodiments of the present disclosure the compositions comprise a plasmid of deoxyribonucleic acid (DNA) that includes one or more insert sequences of nucleic acids that encode for the production of miRNA and a backbone sequence of nucleic acids that facilitates introduction of the one or more insert sequences into one or more of a subject's cells where it is expressed and/or replicated. Expression of the one or more insert sequences by one or more cells of the subject results in an increased production of the miRNA and, therefore, decreased translation or production of the target biomolecule by one or more of the subject's cells.

Some embodiments of the present disclosure relate to compositions that upregulate the production of miRNA that degrades, or causes degradation of, or inactivates or causes the inactivation of, the target mRNA of the target biomolecule.

Some embodiments of the present disclosure relate to a recombinant plasmid (RP). In some embodiments of the present disclosure, the RP comprises a nucleotide sequence of SEQ ID NO. 1 and SEQ ID NO. 2. The RP comprises a nucleotide sequence encoding one or more nucleotide sequences encoding a miRNA sequence that targets the mRNA of serotonin receptor 5HT1a.

Some embodiments of the present disclosure relate to a recombinant plasmid. In some embodiments of the present disclosure, the RP comprises a nucleotide sequence of SEQ ID NO. 1 and SEQ ID NO. 3. The RP comprises a nucleotide sequence encoding one or more nucleotide sequences encoding a miRNA sequence that targets the mRNA of serotonin receptor 5HT1b.

Some embodiments of the present disclosure relate to a recombinant plasmid. In some embodiments of the present disclosure, the RP comprises a nucleotide sequence of SEQ ID NO. 1 and SEQ ID NO. 4. The RP comprises a nucleotide sequence encoding one or more nucleotide sequences encoding a miRNA sequence that targets the mRNA of serotonin receptor 5HT1d.

Some embodiments of the present disclosure relate to a recombinant plasmid. In some embodiments of the present disclosure, the RP comprises a nucleotide sequence of SEQ ID NO. 1 and SEQ ID NO. 5. The RP comprises a nucleotide sequence encoding one or more nucleotide sequences encoding a miRNA sequence that targets the mRNA of serotonin receptor 5HT1e.

Some embodiments of the present disclosure relate to a recombinant plasmid. In some embodiments of the present disclosure, the RP comprises a nucleotide sequence of SEQ ID NO. 1 and SEQ ID NO. 6. The RP comprises a nucleotide sequence encoding one or more nucleotide sequences encoding a miRNA sequence that targets the mRNA of serotonin receptor 5HT1f.

Some embodiments of the present disclosure relate to a recombinant plasmid. In some embodiments of the present disclosure, the RP comprises a nucleotide sequence of SEQ ID NO. 1 and SEQ ID NO. 7. The RP comprises a nucleotide sequence encoding one or more nucleotide sequences encoding a miRNA sequence that targets the mRNA of serotonin receptor 5HT2a.

Some embodiments of the present disclosure relate to a recombinant plasmid. In some embodiments of the present disclosure, the RP comprises a nucleotide sequence of SEQ ID NO. 1 and SEQ ID NO. 8. The RP comprises a nucleotide sequence encoding one or more nucleotide sequences encoding a miRNA sequence that targets the mRNA of serotonin receptor 5HT2b.

Some embodiments of the present disclosure relate to a recombinant plasmid. In some embodiments of the present disclosure, the RP comprises a nucleotide sequence of SEQ ID NO. 1 and SEQ ID NO. 9. The RP comprises a nucleotide sequence encoding one or more nucleotide sequences encoding a miRNA sequence that targets the mRNA of serotonin receptor 5HT2c.

Some embodiments of the present disclosure relate to a recombinant plasmid. In some embodiments of the present disclosure, the RP comprises a nucleotide sequence of SEQ ID NO. 1 and SEQ ID NO. 10. The RP comprises a nucleotide sequence encoding one or more nucleotide sequences encoding a miRNA sequence that targets the mRNA of serotonin receptor 5HT3.

Some embodiments of the present disclosure relate to a recombinant plasmid. In some embodiments of the present disclosure, the RP comprises a nucleotide sequence of SEQ ID NO. 1 and SEQ ID NO. 11. The RP comprises a nucleotide sequence encoding one or more nucleotide sequences encoding a miRNA sequence that targets the mRNA of serotonin receptor 5HT4.

Some embodiments of the present disclosure relate to a recombinant plasmid. In some embodiments of the present disclosure, the RP comprises a nucleotide sequence of SEQ ID NO. 1 and SEQ ID NO. 12. The RP comprises a nucleotide sequence encoding one or more nucleotide sequences encoding a miRNA sequence that targets the mRNA of serotonin receptor 5HT6.

Some embodiments of the present disclosure relate to a recombinant plasmid. In some embodiments of the present disclosure, the RP comprises a nucleotide sequence of SEQ ID NO. 1 and SEQ ID NO. 13 The RP comprises a nucleotide sequence encoding one or more nucleotide sequences encoding a miRNA sequence that targets the mRNA of serotonin receptor 5HT7.

Some embodiments of the present disclosure relate to a method of making a composition/target cell complex. The method comprising a step of administering a RP comprising SEQ ID NO. 1 and one of SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, or SEQ ID NO. 13 to a target cell for forming the composition/target cell complex, wherein the composition/target cell complex causes the target cell to increase production of one or more sequences of miRNA that decreases production of a target biomolecule.

Embodiments of the present disclosure relate to at least one approach for inducing endogenous production of one or more sequences of miRNA that target and silence the mRNA of a target biomolecule, for example serotonin receptor 5HT1a. A first approach utilizes gene vectors containing nucleotide sequences for increasing the endogenous production of one or more sequences of miRNA, which are complete or partial sequences and/or combinations thereof, that target and silence the mRNA of serotonin receptor 5HT1a, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT1b. A first approach utilizes gene vectors containing nucleotide sequences for increasing the endogenous production of one or more sequences of miRNA, which are complete or partial sequences and/or combinations thereof, that target and silence the mRNA of serotonin receptor 5HT1b, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT1d. A first approach utilizes gene vectors containing nucleotide sequences for increasing the endogenous production of one or more sequences of miRNA, which are complete or partial sequences and/or combinations thereof, that target and silence the mRNA of serotonin receptor 5HT1d, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT1e. A first approach utilizes gene vectors containing nucleotide sequences for increasing the endogenous production of one or more sequences of miRNA, which are complete or partial sequences and/or combinations thereof, that target and silence the mRNA of serotonin receptor 5HT1e, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT1f. A first approach utilizes gene vectors containing nucleotide sequences for increasing the endogenous production of one or more sequences of miRNA, which are complete or partial sequences and/or combinations thereof, that target and silence the mRNA of serotonin receptor 5HT1f, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT2a. A first approach utilizes gene vectors containing nucleotide sequences for increasing the endogenous production of one or more sequences of miRNA, which are complete or partial sequences and/or combinations thereof, that target and silence the mRNA of serotonin receptor 5HT2a, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT2b. A first approach utilizes gene vectors containing nucleotide sequences for increasing the endogenous production of one or more sequences of miRNA, which are complete or partial sequences and/or combinations thereof, that target and silence the mRNA of serotonin receptor 5HT2b, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT2c. A first approach utilizes gene vectors containing nucleotide sequences for increasing the endogenous production of one or more sequences of miRNA, which are complete or partial sequences and/or combinations thereof, that target and silence the mRNA of serotonin receptor 5HT2c, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT3. A first approach utilizes gene vectors containing nucleotide sequences for increasing the endogenous production of one or more sequences of miRNA, which are complete or partial sequences and/or combinations thereof, that target and silence the mRNA of serotonin receptor 5HT3 which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT4 A first approach utilizes gene vectors containing nucleotide sequences for increasing the endogenous production of one or more sequences of miRNA, which are complete or partial sequences and/or combinations thereof, that target and silence the mRNA of serotonin receptor 5HT4, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT6. A first approach utilizes gene vectors containing nucleotide sequences for increasing the endogenous production of one or more sequences of miRNA, which are complete or partial sequences and/or combinations thereof, that target and silence the mRNA of serotonin receptor 5HT6, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT7. A first approach utilizes gene vectors containing nucleotide sequences for increasing the endogenous production of one or more sequences of miRNA, which are complete or partial sequences and/or combinations thereof, that target and silence the mRNA of serotonin receptor 5HT7, which can be administered to a subject to increase the subject's production of one or more sequences of the miRNA.

DETAILED DESCRIPTION

Unless defined otherwise, all technical and scientific terms used therein have the meanings that would be commonly understood by one of skill in the art in the context of the present description. Although any methods and materials similar or equivalent to those described therein can also be used in the practice or testing of the present disclosure, the preferred methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "ameliorate" refers to improve and/or to make better and/or to make more satisfactory.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the one or more target cells' production of one or more proteins, and/or any post-translational modifications of one or more proteins.

As used therein, the term "composition" refers to a substance that, when administered to a subject, causes one or more chemical reactions and/or one or more physical reactions and/or one or more physiological reactions and/or one or more biological reactions in the subject. In some embodiments of the present disclosure, the composition is a plasmid vector.

As used therein, the term "endogenous" refers to the production and/or modification of a molecule that originates within a subject.

As used therein, the term "exogenous" refers to a molecule that is within a subject but that did not originate within the subject. As used therein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target biomolecule" refers to a serotonin receptor that is found within a subject. A biomolecule may be endogenous or exogenous to a subject and when bioavailable the biomolecule may inhibit or stimulate a biological process within the subject.

As used therein, the term "target cell" refers to one or more cells and/or cell types that are deleteriously affected, either directly or indirectly, by a dysregulated biomolecule. The term "target cell" also refers to cells that are not deleteriously affected but that are the cells in which it is desired that the composition interacts.

As used therein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used therein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used therein, the terms "unit dosage form" and "unit dose" refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, a composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered without a carrier, by a viral vector, by a protein coat, or by a lipid vesicle. In some embodiments of the present disclosure, the vector is an adeno-associated virus (AAV) vector.

In some embodiments of the present disclosure, the insert comprises one or more nucleotide sequences that encode for production of at least one sequence of miRNA that decreases the production of target biomolecules. The miRNA may, directly or indirectly, bind to and degrade the target mRNA or otherwise inactivate the target mRNA so that less or none of the target-biomolecule protein is produced.

In some embodiments of the present disclosure, the target biomolecule is serotonin receptor 5HT1a.

In some embodiments of the present disclosure, the target biomolecule is serotonin receptor 5HT1b.

In some embodiments of the present disclosure, the target biomolecule is serotonin receptor 5HT1d.

In some embodiments of the present disclosure, the target biomolecule is serotonin receptor 5HT1e.

In some embodiments of the present disclosure, the target biomolecule is serotonin receptor 5HT1f.

In some embodiments of the present disclosure, the target biomolecule is serotonin receptor 5HT2a.

In some embodiments of the present disclosure, the target biomolecule is serotonin receptor 5HT2b.

In some embodiments of the present disclosure, the target biomolecule is serotonin receptor 5HT2c.

In some embodiments of the present disclosure, the target biomolecule is serotonin receptor 5HT3.

In some embodiments of the present disclosure, the target biomolecule is serotonin receptor 5HT4.

In some embodiments of the present disclosure, the target biomolecule is serotonin receptor 5HT6.

In some embodiments of the present disclosure, the target biomolecule is serotonin receptor 5HT7.

In some embodiments of the present disclosure, the insert comprises one or more nucleotide sequences that each encode for one or more miRNA sequences that may be complementary to and degrade, or cause degradation of, mRNA of the target biomolecule.

Some embodiments of the present disclosure relate to a composition that can be administered to a subject with a condition that results, directly or indirectly, from the production of a dysregulated biomolecule. When a therapeutically effective amount of the composition is administered to the subject, the subject may change production and/or functionality of one or more biomolecules.

In some embodiments of the present disclosure, the subject may respond to receiving the therapeutic amount of the composition by changing production and/or functionality of one or more intermediary molecules by changing production of one or more DNA sequences, one or more RNA sequences, and/or one or more proteins that regulate the levels and/or functionality of the one or more intermediary molecules. The one or more intermediary molecules regulate the subject's levels and/or functionality of the one or more biomolecules.

In some embodiments of the present disclosure, administering a therapeutic amount of the composition to a subject upregulates the production, functionality or both one or more sequences of miRNA that each target the mRNA of one or more target biomolecules. In some embodiments of the present disclosure, there are one, two, three, four, five, or six miRNA sequences that each are complementary to and degrade, or cause degradation of, one biomolecule, such as the mRNA of serotonin receptor 5HT1a, serotonin receptor 5HT1b, serotonin receptor 5HT1d, serotonin receptor 5HT1e, serotonin receptor 5HT1f, serotonin receptor 5HT2a, serotonin receptor 5HT2b, serotonin receptor 5HT2c, serotonin receptor 5HT3, serotonin receptor 5HT4, serotonin receptor 5HT6, or serotonin receptor 5HT7. In some embodiments of the present disclosure, the composition may comprise multiple copies of the same nucleotide sequence of miRNA.

In some embodiments of the present disclosure, the composition is an RP that may be used for gene therapy. The gene therapy is useful for increasing the subject's endogenous production of one or more sequences of miRNA that target the mRNA of a target biomolecule. For example, the RP can contain one or more nucleotide sequences that cause increased production of one or more nucleotide sequences that cause an increased production of one or more miRNA sequences that are each complementary to and degrade, or cause degradation of, or inactivate, or cause inactivation of, one biomolecule, such as serotonin receptor 5HT1a, serotonin receptor 5HT1b, serotonin receptor 5HT1d, serotonin receptor 5HT1e, serotonin receptor 5HT1f, serotonin receptor 5HT2a, serotonin receptor 5HT2b, serotonin receptor 5HT2c, serotonin receptor 5HT3, serotonin receptor 5HT4, serotonin receptor 5HT6, or serotonin receptor 5HT7.

In some embodiments of the present disclosure, the delivery vehicle of the RP used for gene therapy may be a vector that is comprised of a virus that can be enveloped, or not (unenveloped), replication effective or not (replication ineffective), or combinations thereof. In some embodiments of the present disclosure, the vector is a virus that is not enveloped and not replication effective. In some embodiments of the present disclosure, the vector is a virus of the Parvoviridae family. In some embodiments of the present disclosure, the vector is a virus of the genus Dependoparvovirus. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

In some embodiments of the present disclosure, the delivery vehicle of the RP used for gene therapy may be a protein coat.

In some embodiments of the present disclosure, the delivery vehicle of the RP used for gene therapy may be a lipid vesicle.

The embodiments of the present disclosure also relate to administering a therapeutically effective amount of the composition. In some embodiments of the present disclosure, the therapeutically effective amount of the composition that is administered to a patient is between about 10 and about $1 \times 10^{16}$ TCID$_{50}$/kg (50% tissue culture infective dose per kilogram of the patient's body mass). In some embodiments of the present disclosure, the therapeutically effective amount of the composition that is administered to the patient is about $1 \times 10^{13}$ TCID$_{50}$/kg. In some embodiments of the present disclosure, the therapeutically effective amount of the composition that is administered to a patient is measured in TPC/kg (total particle count of the composition per kilogram of the patient's body mass). In some embodiments the therapeutically effective amount of the composition is between about 10 and about $1 \times 10^{16}$ TCP/kg.

Some embodiments of the present disclosure relate to an adeno-associated virus (AAV) genome consisting of a RP that when operable inside a target cell will cause the target cell to produce a miRNA sequence that downregulates production of a biomolecule, with examples being serotonin receptor 5HT1a, serotonin receptor 5HT1b, serotonin receptor 5HT1d, serotonin receptor 5HT1e, serotonin receptor 5HT1f, serotonin receptor 5HT2a, serotonin receptor 5HT2b, serotonin receptor 5HT2c, serotonin receptor 5HT3, serotonin receptor 5HT4, serotonin receptor 5HT6, or serotonin receptor 5HT7. The RP is comprised of AAV2 inverted terminal repeats (ITRs), a composite CASI promoter, a human growth hormone (HGH) signal peptide followed by a miRNA expression cassette containing up to six different miRNAs targeting the mRNA of serotonin receptor 5HT1a, serotonin receptor 5HT1b, serotonin receptor 5HT1d, serotonin receptor 5HT1e, serotonin receptor 5HT1f, serotonin receptor 5HT2a, serotonin receptor 5HT2b, serotonin receptor 5HT2c, serotonin receptor 5HT3, serotonin receptor 5HT4, serotonin receptor 5HT6, or serotonin receptor 5HT7, followed by a Woodchuck Hepatitis Virus post-transcriptional regulatory element (WPRE) and a Simian virus 40 (SV40) polyadenylation (polyA) signal.

```
SEQ ID NO. 1 (backbone sequence No. 1):
5' AATCAACCTCTGGATTACAAAATTTGTGAAAGATTGACTGGTATTCTT

AACTATGTTGCTCCTTTTACGCTATGTGGATACGCTGCTTTAATGCCTTT

GTATCATGCTATTGCTTCCCGTATGGCTTTCATTTTCTCCTCCTTGTATA

AATCCTGGTTGCTGTCTCTTTATGAGGAGTTGTGGCCCGTTGTCAGGCAA

CGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCC

CTATTGCCACGGCGGAACTCATCGCCGCCTGCCTTGCCCGCTGCTGGACA

GGGGCTCGGCTGTTGGGCACTGACAATTCCGTGGTGTTGTCGGGGAAATC

ATCGTCCTTTCCTTGGCTGCTCGCCTGTGTTGCCACCTGGATTCTGCGCG

GGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTAAGCTTA

TCGATACCGTCGAGATCTAACTTGTTTATTGCAGCTTATAATGGTTACAA

ATAAAGCAATAGCATCACAAATTTCACAAATAAAGCATTTTTTTCACTGC

ATTCTAGTTGTGGTTTGTCCAAACTCATCAATGTATCTTATCATGTCTGG

ATCTCGACCTCGACTAGAGCATGGCTACGTAGATAAGTAGCATGGCGGGT

TAATCATTAACTACAAGGAACCCCTAGTGATGGAGTTGGCCACTCCCTCT

CTGCGCGCTCGCTCGCTCACTGAGGCCGGGCGACCAAAGGTCGCCCGACG

CCCGGGCTTTGCCCGGGCGGCCTCAGTGAGCGAGCGAGCGCGCAGCTGGC

GTAATAGCGAAGAGGCCCGCACCGATCGCCCTTCCCAACAGTTGCGCAGC

CTGAATGGCGAATGGCGATTCCGTTGCAATGGCTGGCGGTAATATTGTTC
```

-continued

```
TGGATATTACCAGCAAGGCCGATAGTTTGAGTTCTTCTACTCAGGCAAGT

GATGTTATTACTAATCAAAGAAGTATTGCGACAACGGTTAATTTGCGTGA

TGGACAGACTCTTTTACTCGGTGGCCTCACTGATTATAAAAACACTTCTC

AGGATTCTGGCGTACCGTTCCTGTCTAAAATCCCTTTAATCGGCCTCCTG

TTTAGCTCCCGCTCTGATTCTAACGAGGAAAGCACGTTATACGTGCTCGT

CAAAGCAACCATAGTACGCGCCCTGTAGCGGCGCATTAAGCGCGGCGGGT

GTGGTGGTTACGCGCAGCGTGACCGCTACACTTGCCAGCGCCCTAGCGCC

CGCTCCTTTCGCTTTCTTCCCTTCCTTTCTCGCCACGTTCGCCGGCTTTC

CCCGTCAAGCTCTAAATCGGGGGCTCCCTTTAGGGTTCCGATTTAGTGCT

TTACGGCACCTCGACCCCAAAAAACTTGATTAGGGTGATGGTTCACGTAG

TGGGCCATCGCCCTGATAGACGGTTTTTCGCCCTTTGACGTTGGAGTCCA

CGTTCTTTAATAGTGGACTCTTGTTCCAAACTGGAACAACACTCAACCCT

ATCTCGGTCTATTCTTTTGATTTATAAGGGATTTTGCCGATTTCGGCCTA

TTGGTTAAAAAATGAGCTGATTTAACAAAAATTTAACGCGAATTTTAACA

AAATATTAACGTTTACAATTTAAATATTTGCTTATACAATCTTCCTGTTT

TTGGGGCTTTTCTGATTATCAACCGGGGTACATATGATTGACATGCTAGT

TTTACGATTACCGTTCATCGATTCTCTTGTTTGCTCCAGACTCTCAGGCA

ATGACCTGATAGCCTTTGTAGAGACCTCTCAAAAATAGCTACCCTCTCCG

GCATGAATTTATCAGCTAGAACGGTTGAATATCATATTGATGGTGATTTG

ACTGTCTCCGGCCTTTCTCACCCGTTTGAATCTTTACCTACACATTACTC

AGGCATTGCATTTAAAATATATGAGGGTTCTAAAAATTTTTATCCTTGCG

TTGAAATAAAGGCTTCTCCCGCAAAAGTATTACAGGGTCATAATGTTTTT

GGTACAACCGATTTAGCTTTATGCTCTGAGGCTTTATTGCTTAATTTTGC

TAATTCTTTGCCTTGCCTGTATGATTTATTGGATGTTGGAATTCCTGATG

CGGTATTTTCTCCTTACGCATCTGTGCGGTATTTCACACCGCATATGGTG

CACTCTCAGTACAATCTGCTCTGATGCCGCATAGTTAAGCCAGCCCCGAC

ACCCGCCAACACCCGCTGACGCGCCCTGACGGGCTTGTCTGCTCCCGGCA

TCCGCTTACAGACAAGCTGTGACCGTCTCCGGGAGCTGCATGTGTCAGAG

GTTTTCACCGTCATCACCGAAACGCGCGAGACGAAAGGGCCTCGTGATAC

GCCTATTTTTATAGGTTAATGTCATGATAATAATGGTTTCTTAGACGTCA

GGTGGCACTTTCGGGGAAATGTGCGCGGAACCCCTATTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

TTTCGCCCCGAAGAACGTTTTCCAATGATGAGCACTTTTAAAGTTCTGCT

ATGTGGCGCGGTATTATCCCGTATTGACGCCGGGCAAGAGCAACTCGGTC

GCCGCATACACTATTCTCAGAATGACTTGGTTGAGTACTCACCAGTCACA

GAAAAGCATCTTACGGATGGCATGACAGTAAGAGAATTATGCAGTGCTGC
```

-continued

```
CATAACCATGAGTGATAACACTGCGGCCAACTTACTTCTGACAACGATCG

GAGGACCGAAGGAGCTAACCGCTTTTTTGCACAACATGGGGGATCATGTA

ACTCGCCTTGATCGTTGGGAACCGGAGCTGAATGAAGCCATACCAAACGA

CGAGCGTGACACCACGATGCCTGTAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT

AAAAGGATCTAGGTGAAGATCCTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCG

CCTCTCCCCGCGCGTTGGCCGATTCATTAATGCAGCAGCTGCGCGCTCGC

TCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACT

CCATCACTAGGGGTTCCTTGTAGTTAATGATTAACCCGCCATGCTACTTA

TCTACGTAGCCATGCTCTAGGACATTGATTATTGACTAGTGGAGTTCCGC

GTTACATAACTTACGGTAAATGGCCCGCCTGGCTGACCGCCCAACGACCC

CCGCCCATTGACGTCAATAATGACGTATGTTCCCATAGTAACGCCAATAG

GGACTTTCCATTGACGTCAATGGGTGGAGTATTTACGGTAAACTGCCCAC

TTGGCAGTACATCAAGTGTATCATATGCCAAGTACGCCCCCTATTGACGT

CAATGACGGTAAATGGCCCGCCTGGCATTATGCCCAGTACATGACCTTAT

GGGACTTTCCTACTTGGCAGTACATCTACGTATTAGTCATCGCTATTACC

ATGGTCGAGGTGAGCCCCACGTTCTGCTTCACTCTCCCCATCTCCCCCCC
```

-continued

CTCCCCACCCCCAATTTTGTATTTATTTATTTTTTAATTATTTTGTGCAG

CGATGGGGGCGGGGGGGGGGGGGGGCGCGCGCCAGGCGGGGCGGGGGGGG

GCGAGGGGCGGGGCGGGGCGAGGCGGAGAGGTGCGGCGGCAGCCAATCAG

AGCGGCGCGCTCCGAAAGTTTCCTTTTATGGCGAGGCGGCGGCGGCGGCG

GCCCTATAAAAAGCGAAGCGCGCGGCGGGCGGGAGTCGCTGCGCGCTGCC

TTCGCCCCGTGCCCCGCTCCGCCGCCGCCTCGCGCCGCCCGCCCCGGCTC

TGACTGACCGCGTTACTAAAACAGGTAAGTCCGGCCTCCGCGCCGGGTTT

TGGCGCCTCCCGCGGGCGCCCCCCTCCTCACGGCGAGCGCTGCCACGTCA

GACGAAGGGCGCAGCGAGCGTCCTGATCCTTCCGCCCGGACGCTCAGGAC

AGCGGCCCGCTGCTCATAAGACTCGGCCTTAGAACCCCAGTATCAGCAGA

AGGACATTTTAGGACGGGACTTGGGTGACTCTAGGGCACTGGTTTTCTTT

CCAGAGAGCGGAACAGGCGAGGAAAAGTAGTCCCTTCTCGGCGATTCTGC

GGAGGGATCTCCGTGGGGCGGTGAACGCCGATGATGCCTCTACTAACCAT

GTTCATGTTTTCTTTTTTTTTCTACAGGTCCTGGGTGACGAACAGGGTAC

C 3'

SEQ ID NO. 2 (miRNA expression cassette No. 2-
serotonin receptor 5HT1a):
5' GCCACCATGGCCACCGGCTCTCGCACAAGCCTGCTGCTGGCTTTCGGA

CTGCTGTGCCTGCCTTGGCTCCAGGAGGGCTCCGCCGCTAGCATCGATAC

CGTCGCTATGTGCTGGAGGCTTGCTGAAGGCTGTATGCTGATCAATCGGA

TTGCGGTAATCGCGTTTTGGCCTCTGACTGACGCGATTACCGATCCGATT

GATCAGGACACAAGGCCTGTTACTAGCACTCACATGGAACAAATGGCCTC

TAGCCTGGAGGCTTGCTGAAGGCTGTATGCTGATCTTTGCTAAATTGGTG

CACGCGTTTTGGCCTCTGACTGACGCGTGCACCATTAGCAAAGATCAGGA

CACAAGGCCTGTTACTAGCACTCACATGGAACAAATGGCCTCTAGCCTGG

AGGCTTGCTGAAGGCTGTATGCTGACTTCAATCACAATTCCAGCGCCGTT

TTGGCCTCTGACTGACGGCGCTGGAAGTGATTGAAGTCAGGACACAAGGC

CTGTTACTAGCACTCACATGGAACAAATGGCCTCTCTAGAAT 3'

SEQ ID NO. 3 (miRNA expression cassette No. 3-
serotonin receptor 5HT1b):
5' GCCACCATGGCCACCGGCTCTCGCACAAGCCTGCTGCTGGCTTTCGGA

CTGCTGTGCCTGCCTTGGCTCCAGGAGGGCTCCGCCGCTAGCATCGATAC

CGTCGCTATGTGCTGGAGGCTTGCTGAAGGCTGTATGCTGTAATCTTTCG

CTGGCTGCAGTTCGTTTTGGCCTCTGACTGACGAACTGCAGCGCGAAAGA

TTACAGGACACAAGGCCTGTTACTAGCACTCACATGGAACAAATGGCCTC

TAGCCTGGAGGCTTGCTGAAGGCTGTATGCTGTGTTAATGCTGATGTCAC

GCTGCGTTTTGGCCTCTGACTGACGCAGCGTGACCAGCATTAACACAGGA

CACAAGGCCTGTTACTAGCACTCACATGGAACAAATGGCCTCTAGCCTGG

AGGCTTGCTGAAGGCTGTATGCTGTTCACCTGGTTAACACATACACCGTT

TTGGCCTCTGACTGACGGTGTATGTGAACCAGGTGAACAGGACACAAGGC

CTGTTACTAGCACTCACATGGAACAAATGGCCTCTCTAGAAT 3'

SEQ ID NO. 4 (miRNA expression cassette No. 4-
serotonin receptor 5HT1d):
5' GCCACCATGGCCACCGGCTCTCGCACAAGCCTGCTGCTGGCTTTCGGA

CTGCTGTGCCTGCCTTGGCTCCAGGAGGGCTCCGCCGCTAGCATCGATAC

CGTCGCTATGTGCTGGAGGCTTGCTGAAGGCTGTATGCTGATTTCTTCCT

GTGCGCTTTCGCCGTTTTGGCCTCTGACTGACGGCGAAAGCGCAGGAAGA

AATCAGGACACAAGGCCTGTTACTAGCACTCACATGGAACAAATGGCCTC

TAGCCTGGAGGCTTGCTGAAGGCTGTATGCTGAGAATAATCAGATCAGCA

CGCTCGTTTTGGCCTCTGACTGACGAGCGTGCTGCTGATTATTCTCAGGA

CACAAGGCCTGTTACTAGCACTCACATGGAACAAATGGCCTCTAGCCTGG

AGGCTTGCTGAAGGCTGTATGCTGTAATCAGGCTGAATTCAGATAGCGTT

TTGGCCTCTGACTGACGCTATCTGAACAGCCTGATTACAGGACACAAGGC

CTGTTACTAGCACTCACATGGAACAAATGGCCTCTCTAGAAT 3'

SEQ ID NO. 5 (miRNA expression cassette No. 5-
serotonin receptor 5HT1e):
5' GCCACCATGGCCACCGGCTCTCGCACAAGCCTGCTGCTGGCTTTCGGA

CTGCTGTGCCTGCCTTGGCTCCAGGAGGGCTCCGCCGCTAGCATCGATAC

CGTCGCTATGTGCTGGAGGCTTGCTGAAGGCTGTATGCTGATAATCACCG

CTGCAGGTTCAGCGTTTTGGCCTCTGACTGACGCTGAACCTGGCGGTGAT

TATCAGGACACAAGGCCTGTTACTAGCACTCACATGGAACAAATGGCCTC

TAGCCTGGAGGCTTGCTGAAGGCTGTATGCTGTTCAATCGCGTATTGGTA

ATCGCGTTTTGGCCTCTGACTGACGCGATTACCAACGCGATTGAACAGGA

CACAAGGCCTGTTACTAGCACTCACATGGAACAAATGGCCTCTAGCCTGG

AGGCTTGCTGAAGGCTGTATGCTGTGATCATGCTGAAAATGGTGCACGTT

TTGGCCTCTGACTGACGTGCACCATTCAGCATGATCACAGGACACAAGGC

CTGTTACTAGCACTCACATGGAACAAATGGCCTCTCTAGAAT 3'

SEQ ID NO. 6 (miRNA expression cassette No. 6-
serotonin receptor 5HT1f):
5' GCCACCATGGCCACCGGCTCTCGCACAAGCCTGCTGCTGGCTTTCGGA

CTGCTGTGCCTGCCTTGGCTCCAGGAGGGCTCCGCCGCTAGCATCGATAC

CGTCGCTATGTGCTGGAGGCTTGCTGAAGGCTGTATGCTGAGGTAATATC

CTGACGCTCAGCCGTTTTGGCCTCTGACTGACGGCTGAGCGTGGATATTA

CCTCAGGACACAAGGCCTGTTACTAGCACTCACATGGAACAAATGGCCTC

TAGCCTGGAGGCTTGCTGAAGGCTGTATGCTGTACAGAATCAGATAATCA

GCGCCGTTTTGGCCTCTGACTGACGGCGCTGATTCTGATTCTGTACAGGA

CACAAGGCCTGTTACTAGCACTCACATGGAACAAATGGCCTCTAGCCTGG

AGGCTTGCTGAAGGCTGTATGCTGTCATGTTTAAAAATTCGCTGCGCGTT

TTGGCCTCTGACTGACGCGCAGCGAATTTAAACATGACAGGACACAAGGC

CTGTTACTAGCACTCACATGGAACAAATGGCCTCTCTAGAAT 3'

SEQ ID NO. 7 (miRNA expression cassette No. 7-
serotonin receptor 5HT2a):
5' GCCACCATGGCCACCGGCTCTCGCACAAGCCTGCTGCTGGCTTTCGGA

CTGCTGTGCCTGCCTTGGCTCCAGGAGGGCTCCGCCGCTAGCATCGATAC

CGTCGCTATGTGCTGGAGGCTTGCTGAAGGCTGTATGCTGATGAATCGGG

TTGTCTGAATCGCGTTTTGGCCTCTGACTGACGCGATTCAGAACCCGATT

-continued

CATCAGGACACAAGGCCTGTTACTAGCACTCACATGGAACAAATGGCCTC

TAGCCTGGAGGCTTGCTGAAGGCTGTATGCTGAACACTTTGCTATATCAT

CCTGCGTTTTGGCCTCTGACTGACGCAGGATGATAGCAAAGTGTTCAGGA

CACAAGGCCTGTTACTAGCACTCACATGGAACAAATGGCCTCTAGCCTGG

AGGCTTGCTGAAGGCTGTATGCTGTTCTGTTCGTTAAGCTAATGCTCGTT

TTGGCCTCTGACTGACGAGCATTAGCAACGAACAGAACAGGACACAAGGC

CTGTTACTAGCACTCACATGGAACAAATGGCCTCTCTAGAAT 3'

SEQ ID NO. 8 (miRNA expression cassette No. 8-
serotonin receptor 5HT2b):
5' GCCACCATGGCCACCGGCTCTCGCACAAGCCTGCTGCTGGCTTTCGGA

CTGCTGTGCCTGCCTTGGCTCCAGGAGGGCTCCGCCGCTAGCATCGATAC

CGTCGCTATGTGCTGGAGGCTTGCTGAAGGCTGTATGCTGGAGCATTAGC

AATGCGAACAGAAGTTTTGGCCTCTGACTGACTTCTGTTCGTTGCTAATG

CTCCAGGACACAAGGCCTGTTACTAGCACTCACATGGAACAAATGGCCTC

TAGCCTGGAGGCTTGCTGAAGGCTGTATGCTGAAACATAATGGATTCAGC

AGCGCGTTTTGGCCTCTGACTGACGCGCTGCTGACCATTATGTTTCAGGA

CACAAGGCCTGTTACTAGCACTCACATGGAACAAATGGCCTCTAGCCTGG

AGGCTTGCTGAAGGCTGTATGCTGTTATCTTTGCGAAGCTGCCATCCGTT

TTGGCCTCTGACTGACGGATGGCAGCCGCAAAGATAACAGGACACAAGGC

CTGTTACTAGCACTCACATGGAACAAATGGCCTCTCTAGAAT 3'

SEQ ID NO. 9 (miRNA expression cassette No. 9-
serotonin receptor 5HT2c):
5' GCCACCATGGCCACCGGCTCTCGCACAAGCCTGCTGCTGGCTTTCGGA

CTGCTGTGCCTGCCTTGGCTCCAGGAGGGCTCCGCCGCTAGCATCGATAC

CGTCGCTATGTGCTGGAGGCTTGCTGAAGGCTGTATGCTGGCTCCTCCAC

TTGGTGGTTTGGTTTTGGCCTCTGACTGACGCGGCAACATTCTGGTGATT

ACAGGACACAAGGCCTGTTACTAGCACTCACATGGAACAAATGGCCTCTA

GCCTGGAGGCTTGCTGAAGGCTGTATGCTGTCATAATCGCTATTTGGTGC

GGCGTTTTGGCCTCTGACTGACGCCGCACCAAAGCGATTATGACAGGACA

CAAGGCCTGTTACTAGCACTCACATGGAACAAATGGCCTCTAGCCTGGAG

GCTTGCTGAAGGCTGTATGCTGTTCTGATCCTGAAGTTCGGGTTCGTTTT

GGCCTCTGACTGACGAACCCGAACCAGGATCAGAACAGGACACAAGGCCT

GTTACTAGCACTCACATGGAACAAATGGCCTCTCTAGAAT 3'

SEQ ID NO. 10 (miRNA expression cassette No. 10-
serotonin receptor 5HT3):
5' GCCACCATGGCCACCGGCTCTCGCACAAGCCTGCTGCTGGCTTTCGGA

CTGCTGTGCCTGCCTTGGCTCCAGGAGGGCTCCGCCGCTAGCATCGATAC

CGTCGCTATGTGCTGGAGGCTTGCTGAAGGCTGTATGCTGAAATCTTCCG

GTGGTTCCACTGCGTTTTGGCCTCTGACTGACGCAGTGGAACCCGGAAGA

TTTCAGGACACAAGGCCTGTTACTAGCACTCACATGGAACAAATGGCCTC

TAGCCTGGAGGCTTGCTGAAGGCTGTATGCTGATATCCTGAATATGGTAT

GCAGCGTTTTGGCCTCTGACTGACGCTGCATACCATTCAGGATATCAGGA

CACAAGGCCTGTTACTAGCACTCACATGGAACAAATGGCCTCTAGCCTGG

-continued

AGGCTTGCTGAAGGCTGTATGCTGTTTAAAGCTCAAACGCGTTCGCCGTT

TTGGCCTCTGACTGACGGCGAACGCGTGAGCTTTAAACAGGACACAAGGC

CTGTTACTAGCACTCACATGGAACAAATGGCCTCTCTAGAAT 3'

SEQ ID NO. 11 (miRNA expression cassette No. 11-
serotonin receptor 5HT4):
5' GCCACCATGGCCACCGGCTCTCGCACAAGCCTGCTGCTGGCTTTCGGA

CTGCTGTGCCTGCCTTGGCTCCAGGAGGGCTCCGCCGCTAGCATCGATAC

CGTCGCTATGTGCTGGAGGCTTGCTGAAGGCTGTATGCTGTAATAAAGGT

CTGGGAATCACCCGTTTTGGCCTCTGACTGACGGGTGATTCCGACCTTTA

TTACAGGACACAAGGCCTGTTACTAGCACTCACATGGAACAAATGGCCTC

TAGCCTGGAGGCTTGCTGAAGGCTGTATGCTGTAATACGCCAGATCACCA

TCAGCGTTTTGGCCTCTGACTGACGCTGATGGTGCTGGCGTATTACAGGA

CACAAGGCCTGTTACTAGCACTCACATGGAACAAATGGCCTCTAGCCTGG

AGGCTTGCTGAAGGCTGTATGCTGATACAGAAACGAAGGTTCAGGCCGTT

TTGGCCTCTGACTGACGGCCTGAACCCGTTTCTGTATCAGGACACAAGGC

CTGTTACTAGCACTCACATGGAACAAATGGCCTCTCTAGAAT '

SEQ ID NO. 12 (miRNA expression cassette No. 12-
serotonin receptor 5HT6):
5' GCCACCATGGCCACCGGCTCTCGCACAAGCCTGCTGCTGGCTTTCGGA

CTGCTGTGCCTGCCTTGGCTCCAGGAGGGCTCCGCCGCTAGCATCGATAC

CGTCGCTATGTGCTGGAGGCTTGCTGAAGGCTGTATGCTGTCAGATCGCT

GTGGTAAACAGGCGTTTTGGCCTCTGACTGACGCCTGTTTACCAGCGATC

TGACAGGACACAAGGCCTGTTACTAGCACTCACATGGAACAAATGGCCTC

TAGCCTGGAGGCTTGCTGAAGGCTGTATGCTGAGAATCAGATCAGATAGC

GATCCGTTTTGGCCTCTGACTGACGGATCGCTATCTGCTGATTCTCAGGA

CACAAGGCCTGTTACTAGCACTCACATGGAACAAATGGCCTCTAGCCTGG

AGGCTTGCTGAAGGCTGTATGCTGAAACATGCCAACAGCAGAATGCCGTT

TTGGCCTCTGACTGACGGCATTCTGCTGGGCATGTTTCAGGACACAAGGC

CTGTTACTAGCACTCACATGGAACAAATGGCCTCTCTAGAAT 3'

SEQ ID NO. 13 (miRNA expression cassette No. 13-
serotonin receptor 5HT7):
5' GCCACCATGGCCACCGGCTCTCGCACAAGCCTGCTGCTGGCTTTCGGA

CTGCTGTGCCTGCCTTGGCTCCAGGAGGGCTCCGCCGCTAGCATCGATAC

CGTCGCTATGTGCTGGAGGCTTGCTGAAGGCTGTATGCTGACAATCAGAT

ATGGTTGCTCGGCGTTTTGGCCTCTGACTGACGCCGAGCAACTATCTGAT

TGTCAGGACACAAGGCCTGTTACTAGCACTCACATGGAACAAATGGCCTC

TAGCCTGGAGGCTTGCTGAAGGCTGTATGCTGTTTCACAATGCATCGTTC

AGCGCGTTTTGGCCTCTGACTGACGCGCTGAACGGCATTGTGAAACAGGA

CACAAGGCCTGTTACTAGCACTCACATGGAACAAATGGCCTCTAGCCTGG

AGGCTTGCTGAAGGCTGTATGCTGACAATAATGCCAACAGGGTGGTCGTT

TTGGCCTCTGACTGACGACCACCCTGGGCATTATTGTCAGGACACAAGGC

CTGTTACTAGCACTCACATGGAACAAATGGCCTCTCTAGAAT 3'

-continued

SEQ ID NO. 14 = SEQ ID NO. 1 + SEQ ID NO. 2

5' AATCAACCTCTGGATTACAAAATTTGTGAAAGATTGACTGGTATTCTT

AACTATGTTGCTCCTTTTACGCTATGTGGATACGCTGCTTTAATGCCTTT

GTATCATGCTATTGCTTCCCGTATGGCTTTCATTTTCTCCTCCTTGTATA

AATCCTGGTTGCTGTCTCTTTATGAGGAGTTGTGGCCCGTTGTCAGGCAA

CGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCC

CTATTGCCACGGCGGAACTCATCGCCGCCTGCCTTGCCCGCTGCTGGACA

GGGGCTCGGCTGTTGGGCACTGACAATTCCGTGGTGTTGTCGGGGAAATC

ATCGTCCTTTCCTTGGCTGCTCGCCTGTGTTGCCACCTGGATTCTGCGCG

GGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTAAGCTTA

TCGATACCGTCGAGATCTAACTTGTTTATTGCAGCTTATAATGGTTACAA

ATAAAGCAATAGCATCACAAATTTCACAAATAAAGCATTTTTTTCACTGC

ATTCTAGTTGTGGTTTGTCCAAACTCATCAATGTATCTTATCATGTCTGG

ATCTCGACCTCGACTAGAGCATGGCTACGTAGATAAGTAGCATGGCGGGT

TAATCATTAACTACAAGGAACCCCTAGTGATGGAGTTGGCCACTCCCTCT

CTGCGCGCTCGCTCGCTCACTGAGGCCGGGCGACCAAAGGTCGCCCGACG

CCCGGGCTTTGCCCGGGCGGCCTCAGTGAGCGAGCGAGCGCGCAGCTGGC

GTAATAGCGAAGAGGCCCGCACCGATCGCCCTTCCCAACAGTTGCGCAGC

CTGAATGGCGAATGGCGATTCCGTTGCAATGGCTGGCGGTAATATTGTTC

TGGATATTACCAGCAAGGCCGATAGTTTGAGTTCTTCTACTCAGGCAAGT

GATGTTATTACTAATCAAAGAAGTATTGCGACAACGGTTAATTTGCGTGA

TGGACAGACTCTTTTACTCGGTGGCCTCACTGATTATAAAAACACTTCTC

AGGATTCTGGCGTACCGTTCCTGTCTAAAATCCCTTTAATCGGCCTCCTG

TTTAGCTCCCGCTCTGATTCTAACGAGGAAAGCACGTTATACGTGCTCGT

CAAAGCAACCATAGTACGCGCCCTGTAGCGGCGCATTAAGCGCGGCGGGT

GTGGTGGTTACGCGCAGCGTGACCGCTACACTTGCCAGCGCCCTAGCGCC

CGCTCCTTTCGCTTTCTTCCCTTCCTTTCTCGCCACGTTCGCCGGCTTTC

CCCGTCAAGCTCTAAATCGGGGGCTCCCTTTAGGGTTCCGATTTAGTGCT

TTACGGCACCTCGACCCCAAAAAACTTGATTAGGGTGATGGTTCACGTAG

TGGGCCATCGCCCTGATAGACGGTTTTTCGCCCTTTGACGTTGGAGTCCA

CGTTCTTTAATAGTGGACTCTTGTTCCAAACTGGAACAACACTCAACCCT

ATCTCGGTCTATTCTTTTGATTTATAAGGGATTTTGCCGATTTCGGCCTA

TTGGTTAAAAAATGAGCTGATTTAACAAAAATTTAACGCGAATTTTAACA

AAATATTAACGTTTACAATTTAAATATTTGCTTATACAATCTTCCTGTTT

TTGGGGCTTTTCTGATTATCAACCGGGGTACATATGATTGACATGCTAGT

TTTACGATTACCGTTCATCGATTCTCTTGTTTGCTCCAGACTCTCAGGCA

ATGACCTGATAGCCTTTGTAGAGACCTCTCAAAAATAGCTACCCTCTCCG

GCATGAATTTATCAGCTAGAACGGTTGAATATCATATTGATGGTGATTTG

-continued

ACTGTCTCCGGCCTTTCTCACCCGTTTGAATCTTTACCTACACATTACTC

AGGCATTGCATTTAAAATATATGAGGGTTCTAAAAATTTTTATCCTTGCG

TTGAAATAAAGGCTTCTCCCGCAAAAGTATTACAGGGTCATAATGTTTTT

GGTACAACCGATTTAGCTTTATGCTCTGAGGCTTTATTGCTTAATTTTGC

TAATTCTTTGCCTTGCCTGTATGATTTATTGGATGTTGGAATTCCTGATG

CGGTATTTTCTCCTTACGCATCTGTGCGGTATTTCACACCGCATATGGTG

CACTCTCAGTACAATCTGCTCTGATGCCGCATAGTTAAGCCAGCCCCGAC

ACCCGCCAACACCCGCTGACGCGCCCTGACGGGCTTGTCTGCTCCCGGCA

TCCGCTTACAGACAAGCTGTGACCGTCTCCGGGAGCTGCATGTGTCAGAG

GTTTTCACCGTCATCACCGAAACGCGCGAGACGAAAGGGCCTCGTGATAC

GCCTATTTTTATAGGTTAATGTCATGATAATAATGGTTTCTTAGACGTCA

GGTGGCACTTTTCGGGGAAATGTGCGCGGAACCCCTATTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

TTTCGCCCCGAAGAACGTTTTCCAATGATGAGCACTTTTAAAGTTCTGCT

ATGTGGCGCGGTATTATCCCGTATTGACGCCGGGCAAGAGCAACTCGGTC

GCCGCATACACTATTCTCAGAATGACTTGGTTGAGTACTCACCAGTCACA

GAAAAGCATCTTACGGATGGCATGACAGTAAGAGAATTATGCAGTGCTGC

CATAACCATGAGTGATAACACTGCGGCCAACTTACTTCTGACAACGATCG

GAGGACCGAAGGAGCTAACCGCTTTTTTGCACAACATGGGGGATCATGTA

ACTCGCCTTGATCGTTGGGAACCGGAGCTGAATGAAGCCATACCAAACGA

CGAGCGTGACACCACGATGCCTGTAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT

AAAAGGATCTAGGTGAAGATCCTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

-continued

CCCAGCTTGGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCG

CCTCTCCCCGCGCGTTGGCCGATTCATTAATGCAGCAGCTGCGCGCTCGC

TCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACT

CCATCACTAGGGGTTCCTTGTAGTTAATGATTAACCCGCCATGCTACTTA

TCTACGTAGCCATGCTCTAGGACATTGATTATTGACTAGTGGAGTTCCGC

GTTACATAACTTACGGTAAATGGCCCGCCTGGCTGACCGCCCAACGACCC

CCGCCCATTGACGTCAATAATGACGTATGTTCCCATAGTAACGCCAATAG

GGACTTTCCATTGACGTCAATGGGTGGAGTATTTACGGTAAACTGCCCAC

TTGGCAGTACATCAAGTGTATCATATGCCAAGTACGCCCCCTATTGACGT

CAATGACGGTAAATGGCCCGCCTGGCATTATGCCCAGTACATGACCTTAT

GGGACTTTCCTACTTGGCAGTACATCTACGTATTAGTCATCGCTATTACC

ATGGTCGAGGTGAGCCCCACGTTCTGCTTCACTCTCCCCATCTCCCCCCC

CTCCCCACCCCCAATTTTGTATTTATTTATTTTTTAATTATTTTGTGCAG

CGATGGGGGCGGGGGGGGGGGGGGCGCGCGCCAGGCGGGGCGGGGGGGG

GCGAGGGGCGGGGGGGGCGAGGCGGAGAGGTGCGGCGGCAGCCAATCAGA

GCGGCGCGCTCCGAAAGTTTCCTTTTATGGCGAGGCGGCGGCGGCGGCGG

CCCTATAAAAAGCGAAGCGCGCGGCGGGCGGGAGTCGCTGCGCGCTGCCT

TCGCCCCGTGCCCCGCTCCGCCGCCGCCTCGCGCCGCCCGCCCCGGCTCT

GACTGACCGCGTTACTAAAACAGGTAAGTCCGGCCTCCGCGCCGGGTTTT

GGCGCCTCCCGCGGGCGCCCCCCTCCTCACGGCGAGCGCTGCCACGTCAG

ACGAAGGGCGCAGCGAGCGTCCTGATCCTTCCGCCCGGACGCTCAGGACA

GCGGCCCGCTGCTCATAAGACTCGGCCTTAGAACCCCAGTATCAGCAGAA

GGACATTTTAGGACGGGACTTGGGTGACTCTAGGGCACTGGTTTTCTTTC

CAGAGAGCGGAACAGGCGAGGAAAAGTAGTCCCTTCTCGGCGATTCTGCG

GAGGGATCTCCGTGGGGCGGTGAACGCCGATGATGCCTCTACTAACCATG

TTCATGTTTTCTTTTTTTTTCTACAGGTCCTGGGTGACGAACAGGGTACC

GCCACCATGGCCACCGGCTCTCGCACAAGCCTGCTGCTGGCTTTCGGACT

GCTGTGCCTGCCTTGGCTCCAGGAGGGCTCCGCCGCTAGCATCGATACCG

TCGCTATGTGCTGGAGGCTTGCTGAAGGCTGTATGCTGATCAATCGGATT

GCGGTAATCGCGTTTTGGCCTCTGACTGACGCGATTACCGATCCGATTGA

TCAGGACACAAGGCCTGTTACTAGCACTCACATGGAACAAATGGCCTCTA

-continued

GCCTGGAGGCTTGCTGAAGGCTGTATGCTGATCTTTGCTAAATTGGTGCA

CGCGTTTTGGCCTCTGACTGACGCGTGCACCATTAGCAAAGATCAGGACA

CAAGGCCTGTTACTAGCACTCACATGGAACAAATGGCCTCTAGCCTGGAG

GCTTGCTGAAGGCTGTATGCTGACTTCAATCACAATTCCAGCGCCGTTTT

GGCCTCTGACTGACGGCGCTGGAAGTGATTGAAGTCAGGACACAAGGCCT

GTTACTAGCACTCACATGGAACAAATGGCCTCTCTAGAAT 3'

SEQ ID NO. 15 = SEQ ID NO. 1 + SEQ ID NO. 3
5' AATCAACCTCTGGATTACAAAATTTGTGAAAGATTGACTGGTATTCTT

AACTATGTTGCTCCTTTTACGCTATGTGGATACGCTGCTTTAATGCCTTT

GTATCATGCTATTGCTTCCCGTATGGCTTTCATTTTCTCCTCCTTGTATA

AATCCTGGTTGCTGTCTCTTTATGAGGAGTTGTGGCCCGTTGTCAGGCAA

CGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCC

CTATTGCCACGGCGGAACTCATCGCCGCCTGCCTTGCCCGCTGCTGGACA

GGGGCTCGGCTGTTGGGCACTGACAATTCCGTGGTGTTGTCGGGGAAATC

ATCGTCCTTTCCTTGGCTGCTCGCCTGTGTTGCCACCTGGATTCTGCGCG

GGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTAAGCTTA

TCGATACCGTCGAGATCTAACTTGTTTATTGCAGCTTATAATGGTTACAA

ATAAAGCAATAGCATCACAAATTTCACAAATAAAGCATTTTTTTCACTGC

ATTCTAGTTGTGGTTTGTCCAAACTCATCAATGTATCTTATCATGTCTGG

ATCTCGACCTCGACTAGAGCATGGCTACGTAGATAAGTAGCATGGCGGGT

TAATCATTAACTACAAGGAACCCCTAGTGATGGAGTTGGCCACTCCCTCT

CTGCGCGCTCGCTCGCTCACTGAGGCCGGGCGACCAAAGGTCGCCCGACG

CCCGGGCTTTGCCCGGGCGGCCTCAGTGAGCGAGCGAGCGCGCAGCTGGC

GTAATAGCGAAGAGGCCCGCACCGATCGCCCTTCCCAACAGTTGCGCAGC

CTGAATGGCGAATGGCGATTCCGTTGCAATGGCTGGCGGTAATATTGTTC

TGGATATTACCAGCAAGGCCGATAGTTTGAGTTCTTCTACTCAGGCAAGT

GATGTTATTACTAATCAAAGAAGTATTGCGACAACGGTTAATTTGCGTGA

TGGACAGACTCTTTTACTCGGTGGCCTCACTGATTATAAAAACACTTCTC

AGGATTCTGGCGTACCGTTCCTGTCTAAAATCCCTTTAATCGGCCTCCTG

TTTAGCTCCCGCTCTGATTCTAACGAGGAAAGCACGTTATACGTGCTCGT

CAAAGCAACCATAGTACGCGCCCTGTAGCGGCGCATTAAGCGCGGCGGGT

GTGGTGGTTACGCGCAGCGTGACCGCTACACTTGCCAGCGCCCTAGCGCC

CGCTCCTTTCGCTTTCTTCCCTTCCTTTCTCGCCACGTTCGCCGGCTTTC

CCCGTCAAGCTCTAAATCGGGGGCTCCCTTTAGGGTTCCGATTTAGTGCT

TTACGCACCTCGACCCCAAAAAACTTGATTAGGGTGATGGTTCACGTAG

TGGGCCATCGCCCTGATAGACGGTTTTTCGCCCTTTGACGTTGGAGTCCA

CGTTCTTTAATAGTGGACTCTTGTTCCAAACTGGAACAACACTCAACCCT

ATCTCGGTCTATTCTTTTGATTTATAAGGGATTTTGCCGATTTCGGCCTA

-continued

```
TTGGTTAAAAAATGAGCTGATTTAACAAAAATTTAACGCGAATTTTAACA

AAATATTAACGTTTACAATTTAAATATTTGCTTATACAATCTTCCTGTTT

TTGGGGCTTTTCTGATTATCAACCGGGGTACATATGATTGACATGCTAGT

TTTACGATTACCGTTCATCGATTCTCTTGTTTGCTCCAGACTCTCAGGCA

ATGACCTGATAGCCTTTGTAGAGACCTCTCAAAAATAGCTACCCTCTCCG

GCATGAATTTATCAGCTAGAACGGTTGAATATCATATTGATGGTGATTTG

ACTGTCTCCGGCCTTTCTCACCCGTTTGAATCTTTACCTACACATTACTC

AGGCATTGCATTTAAAATATATGAGGGTTCTAAAAATTTTTATCCTTGCG

TTGAAATAAAGGCTTCTCCCGCAAAAGTATTACAGGGTCATAATGTTTTT

GGTACAACCGATTTAGCTTTATGCTCTGAGGCTTTATTGCTTAATTTTGC

TAATTCTTTGCCTTGCCTGTATGATTTATTGGATGTTGGAATTCCTGATG

CGGTATTTTCTCCTTACGCATCTGTGCGGTATTTCACACCGCATATGGTG

CACTCTCAGTACAATCTGCTCTGATGCCGCATAGTTAAGCCAGCCCCGAC

ACCCGCCAACACCCGCTGACGCGCCCTGACGGGCTTGTCTGCTCCCGGCA

TCCGCTTACAGACAAGCTGTGACCGTCTCCGGGAGCTGCATGTGTCAGAG

GTTTTCACCGTCATCACCGAAACGCGCGAGACGAAAGGGCCTCGTGATAC

GCCTATTTTTATAGGTTAATGTCATGATAATAATGGTTTCTTAGACGTCA

GGTGGCACTTTTCGGGGAAATGTGCGCGGAACCCCTATTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

TTTCGCCCCGAAGAACGTTTTCCAATGATGAGCACTTTTAAAGTTCTGCT

ATGTGGCGCGGTATTATCCCGTATTGACGCCGGGCAAGAGCAACTCGGTC

GCCGCATACACTATTCTCAGAATGACTTGGTTGAGTACTCACCAGTCACA

GAAAAGCATCTTACGGATGGCATGACAGTAAGAGAATTATGCAGTGCTGC

CATAACCATGAGTGATAACACTGCGGCCAACTTACTTCTGACAACGATCG

GAGGACCGAAGGAGCTAACCGCTTTTTTGCACAACATGGGGGATCATGTA

ACTCGCCTTGATCGTTGGGAACCGGAGCTGAATGAAGCCATACCAAACGA

CGAGCGTGACACCACGATGCCTGTAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT

AAAAGGATCTAGGTGAAGATCCTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTCTGCGCGTAATCTGCTGCTTGCAA
```

-continued

```
ACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCG

CCTCTCCCCGCGCGTTGGCCGATTCATTAATGCAGCAGCTGCGCGCTCGC

TCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACT

CCATCACTAGGGGTTCCTTGTAGTTAATGATTAACCCGCCATGCTACTTA

TCTACGTAGCCATGCTCTAGGACATTGATTATTGACTAGTGGAGTTCCGC

GTTACATAACTTACGGTAAATGGCCCGCCTGGCTGACCGCCCAACGACCC

CCGCCCATTGACGTCAATAATGACGTATGTTCCCATAGTAACGCCAATAG

GGACTTTCCATTGACGTCAATGGGTGGAGTATTTACGGTAAACTGCCCAC

TTGGCAGTACATCAAGTGTATCATATGCCAAGTACGCCCCCTATTGACGT

CAATGACGGTAAATGGCCCGCCTGGCATTATGCCCAGTACATGACCTTAT

GGGACTTTCCTACTTGGCAGTACATCTACGTATTAGTCATCGCTATTACC

ATGGTCGAGGTGAGCCCCACGTTCTGCTTCACTCTCCCCATCTCCCCCCC

CTCCCCACCCCCAATTTTGTATTTATTTATTTTTTAATTATTTTGTGCAG

CGATGGGGCGGGGGGGGGGGGGGGCGCGCGCCAGGCGGGGCGGGGGGG

GCGAGGGGCGGGGGGGCGAGGCGGAGAGGTGCGGCGGCAGCCAATCAGA

GCGGCGCGCTCCGAAAGTTTCCTTTTATGGCGAGGCGGCGGCGGCGGCGG

CCCTATAAAAAGCGAAGCGCGCGGCGGGCGGGAGTCGCTGCGCGCTGCCT

TCGCCCCGTGCCCCGCTCCGCCGCCGCCTCGCGCCGCCCGCCCCGGCTCT

GACTGACCGCGTTACTAAAACAGGTAAGTCCGGCCTCCGCGCCGGGTTTT

GGCGCCTCCCGCGGGCGCCCCCCTCCTCACGGCGAGCGCTGCCACGTCAG

ACGAAGGGCGCAGCGAGCGTCCTGATCCTTCCGCCCGGACGCTCAGGACA

GCGGCCCGCTGCTCATAAGACTCGGCCTTAGAACCCCAGTATCAGCAGAA

GGACATTTTAGGACGGGACTTGGGTGACTCTAGGGCACTGGTTTTCTTTC

CAGAGAGCGGAACAGGCGAGGAAAAGTAGTCCCTTCTCGGCGATTCTGCG

GAGGGATCTCCGTGGGGCGGTGAACGCCGATGATGCCTCTACTAACCATG
```

-continued

TTCATGTTTTCTTTTTTTTTCTACAGGTCCTGGGTGACGAACAGGGTACC

GCCACCATGGCCACCGGCTCTCGCACAAGCCTGCTGCTGGCTTTCGGACT

GCTGTGCCTGCCTTGGCTCCAGGAGGGCTCCGCCGCTAGCATCGATACCG

TCGCTATGTGCTGGAGGCTTGCTGAAGGCTGTATGCTGTAATCTTTCGCT

GGCTGCAGTTCGTTTTGGCCTCTGACTGACGAACTGCAGCGCGAAAGATT

ACAGGACACAAGGCCTGTTACTAGCACTCACATGGAACAAATGGCCTCTA

GCCTGGAGGCTTGCTGAAGGCTGTATGCTGTGTTAATGCTGATGTCACGC

TGCGTTTTGGCCTCTGACTGACGCAGCGTGACCAGCATTAACACAGGACA

CAAGGCCTGTTACTAGCACTCACATGGAACAAATGGCCTCTAGCCTGGAG

GCTTGCTGAAGGCTGTATGCTGTTCACCTGGTTAACACATACACCGTTTT

GGCCTCTGACTGACGGTGTATGTGAACCAGGTGAACAGGACACAAGGCCT

GTTACTAGCACTCACATGGAACAAATGGCCTCTCTAGAAT 3'

SEQ ID NO. 16 = SEQ ID NO. 1 + SEQ ID NO. 4
5' AATCAACCTCTGGATTACAAAATTTGTGAAAGATTGACTGGTATTCTT

AACTATGTTGCTCCTTTTACGCTATGTGGATACGCTGCTTTAATGCCTTT

GTATCATGCTATTGCTTCCCGTATGGCTTTCATTTTCTCCTCCTTGTATA

AATCCTGGTTGCTGTCTCTTTATGAGGAGTTGTGGCCCGTTGTCAGGCAA

CGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCC

CTATTGCCACGGCGGAACTCATCGCCGCCTGCCTTGCCCGCTGCTGGACA

GGGGCTCGGCTGTTGGGCACTGACAATTCCGTGGTGTTGTCGGGGAAATC

ATCGTCCTTTCCTTGGCTGCTCGCCTGTGTTGCCACCTGGATTCTGCGCG

GGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTAAGCTTA

TCGATACCGTCGAGATCTAACTTGTTTATTGCAGCTTATAATGGTTACAA

ATAAAGCAATAGCATCACAAATTTCACAAATAAAGCATTTTTTTCACTGC

ATTCTAGTTGTGGTTTGTCCAAACTCATCAATGTATCTTATCATGTCTGG

ATCTCGACCTCGACTAGAGCATGGCTACGTAGATAAGTAGCATGGCGGGT

TAATCATTAACTACAAGGAACCCCTAGTGATGGAGTTGGCCACTCCCTCT

CTGCGCGCTCGCTCGCTCACTGAGGCCGGGCGACCAAAGGTCGCCCGACG

CCCGGGCTTTGCCCGGGCGGCCTCAGTGAGCGAGCGAGCGCGCAGCTGGC

GTAATAGCGAAGAGGCCCGCACCGATCGCCCTTCCCAACAGTTGCGCAGC

CTGAATGGCGAATGGCGATTCCGTTGCAATGGCTGGCGGTAATATTGTTC

TGGATATTACCAGCAAGGCCGATAGTTTGAGTTCTTCTACTCAGGCAAGT

GATGTTATTACTAATCAAAGAAGTATTGCGACAACGGTTAATTTGCGTGA

TGGACAGACTCTTTTACTCGGTGGCCTCACTGATTATAAAAACACTTCTC

AGGATTCTGGCGTACCGTTCCTGTCTAAAATCCCTTTAATCGGCCTCCTG

TTTAGCTCCCGCTCTGATTCTAACGAGGAAAGCACGTTATACGTGCTCGT

CAAAGCAACCATAGTACGCGCCCTGTAGCGGCGCATTAAGCGCGGCGGGT

GTGGTGGTTACGCGCAGCGTGACCGCTACACTTGCCAGCGCCCTAGCGCC

-continued

CGCTCCTTTCGCTTTCTTCCCTTCCTTTCTCGCCACGTTCGCCGGCTTTC

CCCGTCAAGCTCTAAATCGGGGGCTCCCTTTAGGGTTCCGATTTAGTGCT

TTACGGCACCTCGACCCCAAAAAACTTGATTAGGGTGATGGTTCACGTAG

TGGGCCATCGCCCTGATAGACGGTTTTTCGCCCTTTGACGTTGGAGTCCA

CGTTCTTTAATAGTGGACTCTTGTTCCAAACTGGAACAACACTCAACCCT

ATCTCGGTCTATTCTTTTGATTTATAAGGGATTTTGCCGATTTCGGCCTA

TTGGTTAAAAAATGAGCTGATTTAACAAAAATTTAACGCGAATTTTAACA

AAATATTAACGTTTACAATTTAAATATTTGCTTATACAATCTTCCTGTTT

TTGGGGCTTTTCTGATTATCAACCGGGGTACATATGATTGACATGCTAGT

TTTACGATTACCGTTCATCGATTCTCTTGTTTGCTCCAGACTCTCAGGCA

ATGACCTGATAGCCTTTGTAGAGACCTCTCAAAAATAGCTACCCTCTCCG

GCATGAATTTATCAGCTAGAACGGTTGAATATCATATTGATGGTGATTTG

ACTGTCTCCGGCCTTTCTCACCCGTTTGAATCTTTACCTACACATTACTC

AGGCATTGCATTTAAAATATATGAGGGTTCTAAAAATTTTTATCCTTGCG

TTGAAATAAAGGCTTCTCCCGCAAAAGTATTACAGGGTCATAATGTTTTT

GGTACAACCGATTTAGCTTTATGCTCTGAGGCTTTATTGCTTAATTTTGC

TAATTCTTTGCCTTGCCTGTATGATTTATTGGATGTTGGAATTCCTGATG

CGGTATTTTCTCCTTACGCATCTGTGCGGTATTTCACACCGCATATGGTG

CACTCTCAGTACAATCTGCTCTGATGCCGCATAGTTAAGCCAGCCCCGAC

ACCCGCCAACACCCGCTGACGCGCCCTGACGGGCTTGTCTGCTCCCGGCA

TCCGCTTACAGACAAGCTGTGACCGTCTCCGGGAGCTGCATGTGTCAGAG

GTTTTCACCGTCATCACCGAAACGCGCGAGACGAAAGGGCCTCGTGATAC

GCCTATTTTTATAGGTTAATGTCATGATAATAATGGTTTCTTAGACGTCA

GGTGGCACTTTTCGGGGAAATGTGCGCGGAACCCCTATTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

TTTCGCCCCGAAGAACGTTTTCCAATGATGAGCACTTTTAAAGTTCTGCT

ATGTGGCGCGGTATTATCCCGTATTGACGCCGGGCAAGAGCAACTCGGTC

GCCGCATACACTATTCTCAGAATGACTTGGTTGAGTACTCACCAGTCACA

GAAAAGCATCTTACGGATGGCATGACAGTAAGAGAATTATGCAGTGCTGC

CATAACCATGAGTGATAACACTGCGGCCAACTTACTTCTGACAACGATCG

GAGGACCGAAGGAGCTAACCGCTTTTTTGCACAACATGGGGGATCATGTA

ACTCGCCTTGATCGTTGGGAACCGGAGCTGAATGAAGCCATACCAAACGA

CGAGCGTGACACCACGATGCCTGTAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

Page numbers in left and right margins: 5, 10, 15, 20, 25, 30, 35, 40, 45, 50, 55, 60, 65

-continued

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT

AAAAGGATCTAGGTGAAGATCCTTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCG

CCTCTCCCCGCGCGTTGGCCGATTCATTAATGCAGCAGCTGCGCGCTCGC

TCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACT

CCATCACTAGGGGTTCCTTGTAGTTAATGATTAACCCGCCATGCTACTTA

TCTACGTAGCCATGCTCTAGGACATTGATTATTGACTAGTGGAGTTCCGC

GTTACATAACTTACGGTAAATGGCCCGCCTGGCTGACCGCCCAACGACCC

CCGCCCATTGACGTCAATAATGACGTATGTTCCCATAGTAACGCCAATAG

GGACTTTCCATTGACGTCAATGGGTGGAGTATTTACGGTAAACTGCCCAC

TTGGCAGTACATCAAGTGTATCATATGCCAAGTACGCCCCCTATTGACGT

CAATGACGGTAAATGGCCCGCCTGGCATTATGCCCAGTACATGACCTTAT

GGGACTTTCCTACTTGGCAGTACATCTACGTATTAGTCATCGCTATTACC

ATGGTCGAGGTGAGCCCCACGTTCTGCTTCACTCTCCCCATCTCCCCCCC

CTCCCCACCCCCAATTTTGTATTTATTTATTTTTTAATTATTTTGTGCAG

CGATGGGGGCGGGGGGGGGGGGGGCGCGCGCCAGGCGGGGCGGGGGGGG

GCGAGGGGCGGGGCGGGGCGAGGCGGAGAGGTGCGGCGGCAGCCAATCAG

AGCGGCGCGCTCCGAAAGTTTCCTTTTATGGCGAGGCGGCGGCGGCGGCG

GCCCTATAAAAAGCGAAGCGCGCGGCGGGCGGGAGTCGCTGCGCGCTGCC

TTCGCCCCGTGCCCCGCTCCGCCGCCGCCTCGCGCCGCCCGCCCCGGCTC

TGACTGACCGCGTTACTAAAACAGGTAAGTCCGGCCTCCGCGCCGGGTTT

-continued

TGGCGCCTCCCGCGGGCGCCCCCCTCCTCACGGCGAGCGCTGCCACGTCA

GACGAAGGGCGCAGCGAGCGTCCTGATCCTTCCGCCCGGACGCTCAGGAC

AGCGGCCCGCTGCTCATAAGACTCGGCCTTAGAACCCCAGTATCAGCAGA

AGGACATTTTAGGACGGGACTTGGGTGACTCTAGGGCACTGGTTTTCTTT

CCAGAGAGCGGAACAGGCGAGGAAAAGTAGTCCCTTCTCGGCGATTCTGC

GGAGGGATCTCCGTGGGGCGGTGAACGCCGATGATGCCTCTACTAACCAT

GTTCATGTTTTCTTTTTTTTTTCTACAGGTCCTGGGTGACGAACAGGGTAC

CGCCACCATGGCCACCGGCTCTCGCACAAGCCTGCTGCTGGCTTTCGGAC

TGCTGTGCCTGCCTTGGCTCCAGGAGGGCTCCGCCGCTAGCATCGATACC

GTCGCTATGTGCTGGAGGCTTGCTGAAGGCTGTATGCTGATTTCTTCCTG

TGCGCTTTCGCCGTTTTGGCCTCTGACTGACGGCGAAAGCGCAGGAAGAA

ATCAGGACACAAGGCCTGTTACTAGCACTCACATGGAACAAATGGCCTCT

AGCCTGGAGGCTTGCTGAAGGCTGTATGCTGAGAATAATCAGATCAGCAC

GCTCGTTTTGGCCTCTGACTGACGAGCGTGCTGCTGATTATTCTCAGGAC

ACAAGGCCTGTTACTAGCACTCACATGGAACAAATGGCCTCTAGCCTGGA

GGCTTGCTGAAGGCTGTATGCTGTAATCAGGCTGAATTCAGATAGCGTTT

TGGCCTCTGACTGACGCTATCTGAACAGCCTGATTACAGGACACAAGGCC

TGTTACTAGCACTCACATGGAACAAATGGCCTCTCTAGAAT 3'

SEQ ID NO. 17 = SEQ ID NO. 1 + SEQ ID NO. 5
5' AATCAACCTCTGGATTACAAAATTTGTGAAAGATTGACTGGTATTCTT

AACTATGTTGCTCCTTTTACGCTATGTGGATACGCTGCTTTAATGCCTTT

GTATCATGCTATTGCTTCCCGTATGGCTTTCATTTTCTCCTCCTTGTATA

AATCCTGGTTGCTGTCTCTTTATGAGGAGTTGTGGCCCGTTGTCAGGCAA

CGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCC

CTATTGCCACGGCGGAACTCATCGCCGCCTGCCTTGCCCGCTGCTGGACA

GGGGCTCGGCTGTTGGGCACTGACAATTCCGTGGTGTTGTCGGGGAAATC

ATCGTCCTTTCCTTGGCTGCTCGCCTGTGTTGCCACCTGGATTCTGCGCG

GGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTAAGCTTA

TCGATACCGTCGAGATCTAACTTGTTTATTGCAGCTTATAATGGTTACAA

ATAAAGCAATAGCATCACAAATTTCACAAATAAAGCATTTTTTTCACTGC

ATTCTAGTTGTGGTTTGTCCAAACTCATCAATGTATCTTATCATGTCTGG

ATCTCGACCTCGACTAGAGCATGGCTACGTAGATAAGTAGCATGGCGGGT

TAATCATTAACTACAAGGAACCCCTAGTGATGGAGTTGGCCACTCCCTCT

CTGCGCGCTCGCTCGCTCACTGAGGCCGGGCGACCAAAGGTCGCCCGACG

CCCGGGCTTTGCCCGGGCGGCCTCAGTGAGCGAGCGAGCGCGCAGCTGGC

GTAATAGCGAAGAGGCCCGCACCGATCGCCCTTCCCAACAGTTGCGCAGC

CTGAATGGCGAATGGCGATTCCGTTGCAATGGCTGGCGGTAATATTGTTC

TGGATATTACCAGCAAGGCCGATAGTTTGAGTTCTTCTACTCAGGCAAGT

-continued

```
GATGTTATTACTAATCAAAGAAGTATTGCGACAACGGTTAATTTGCGTGA

TGGACAGACTCTTTTACTCGGTGGCCTCACTGATTATAAAAACACTTCTC

AGGATTCTGGCGTACCGTTCCTGTCTAAAATCCCTTTAATCGGCCTCCTG

TTTAGCTCCCGCTCTGATTCTAACGAGGAAAGCACGTTATACGTGCTCGT

CAAAGCAACCATAGTACGCGCCCTGTAGCGGCGCATTAAGCGCGGCGGGT

GTGGTGGTTACGCGCAGCGTGACCGCTACACTTGCCAGCGCCCTAGCGCC

CGCTCCTTTCGCTTTCTTCCCTTCCTTTCTCGCCACGTTCGCCGGCTTTC

CCCGTCAAGCTCTAAATCGGGGGCTCCCTTTAGGGTTCCGATTTAGTGCT

TTACGGCACCTCGACCCCAAAAAACTTGATTAGGGTGATGGTTCACGTAG

TGGGCCATCGCCCTGATAGACGGTTTTTCGCCCTTTGACGTTGGAGTCCA

CGTTCTTTAATAGTGGACTCTTGTTCCAAACTGGAACAACACTCAACCCT

ATCTCGGTCTATTCTTTTGATTTATAAGGGATTTTGCCGATTTCGGCCTA

TTGGTTAAAAAATGAGCTGATTTAACAAAAATTTAACGCGAATTTTAACA

AAATATTAACGTTTACAATTTAAATATTTGCTTATACAATCTTCCTGTTT

TTGGGGCTTTTCTGATTATCAACCGGGGTACATATGATTGACATGCTAGT

TTTACGATTACCGTTCATCGATTCTCTTGTTTGCTCCAGACTCTCAGGCA

ATGACCTGATAGCCTTTGTAGAGACCTCTCAAAAATAGCTACCCTCTCCG

GCATGAATTTATCAGCTAGAACGGTTGAATATCATATTGATGGTGATTTG

ACTGTCTCCGGCCTTTCTCACCCGTTTGAATCTTTACCTACACATTACTC

AGGCATTGCATTTAAAATATATGAGGGTTCTAAAAATTTTTATCCTTGCG

TTGAAATAAAGGCTTCTCCCGCAAAAGTATTACAGGGTCATAATGTTTTT

GGTACAACCGATTTAGCTTTATGCTCTGAGGCTTTATTGCTTAATTTTGC

TAATTCTTTGCCTTGCCTGTATGATTTATTGGATGTTGGAATTCCTGATG

CGGTATTTTCTCCTTACGCATCTGTGCGGTATTTCACACCGCATATGGTG

CACTCTCAGTACAATCTGCTCTGATGCCGCATAGTTAAGCCAGCCCCGAC

ACCCGCCAACACCCGCTGACGCGCCCTGACGGGCTTGTCTGCTCCCGGCA

TCCGCTTACAGACAAGCTGTGACCGTCTCCGGGAGCTGCATGTGTCAGAG

GTTTTCACCGTCATCACCGAAACGCGCGAGACGAAAGGGCCTCGTGATAC

GCCTATTTTTATAGGTTAATGTCATGATAATAATGGTTTCTTAGACGTCA

GGTGGCACTTTTCGGGGAAATGTGCGCGGAACCCCTATTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

TTTCGCCCCGAAGAACGTTTTCCAATGATGAGCACTTTTAAAGTTCTGCT

ATGTGGCGCGGTATTATCCCGTATTGACGCCGGGCAAGAGCAACTCGGTC

GCCGCATACACTATTCTCAGAATGACTTGGTTGAGTACTCACCAGTCACA

GAAAAGCATCTTACGGATGGCATGACAGTAAGAGAATTATGCAGTGCTGC

CATAACCATGAGTGATAACACTGCGGCCAACTTACTTCTGACAACGATCG

GAGGACCGAAGGAGCTAACCGCTTTTTTGCACAACATGGGGGATCATGTA
```

-continued

```
ACTCGCCTTGATCGTTGGGAACCGGAGCTGAATGAAGCCATACCAAACGA

CGAGCGTGACACCACGATGCCTGTAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT

AAAAGGATCTAGGTGAAGATCCTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCG

CCTCTCCCCGCGCGTTGGCCGATTCATTAATGCAGCAGCTGCGCGCTCGC

TCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACT

CCATCACTAGGGGTTCCTTGTAGTTAATGATTAACCCGCCATGCTACTTA

TCTACGTAGCCATGCTCTAGGACATTGATTATTGACTAGTGGAGTTCCGC

GTTACATAACTTACGGTAAATGGCCCGCCTGGCTGACCGCCCAACGACCC

CCGCCCATTGACGTCAATAATGACGTATGTTCCCATAGTAACGCCAATAG

GGACTTTCCATTGACGTCAATGGGTGGAGTATTTACGGTAAACTGCCCAC

TTGGCAGTACATCAAGTGTATCATATGCCAAGTACGCCCCCTATTGACGT

CAATGACGGTAAATGGCCCGCCTGGCATTATGCCCAGTACATGACCTTAT

GGGACTTTCCTACTTGGCAGTACATCTACGTATTAGTCATCGCTATTACC

ATGGTCGAGGTGAGCCCCACGTTCTGCTTCACTCTCCCCATCTCCCCCCC

CTCCCCACCCCCAATTTTGTATTTATTTATTTTTTAATTATTTTGTGCAG
```

CGATGGGGGCGGGGGGGGGGGGGGGGCGCGCGCCAGGCGGGGCGGGGGGGG

GCGAGGGGCGGGGCGGGGCGAGGCGGAGAGGTGCGGCGGCAGCCAATCAG

AGCGGCGCGCTCCGAAAGTTTCCTTTTATGGCGAGGCGGCGGCGGCGGCG

GCCCTATAAAAAGCGAAGCGCGCGGCGGGCGGGAGTCGCTGCGCGCTGCC

TTCGCCCCGTGCCCCGCTCCGCCGCCGCCTCGCGCCGCCCGCCCCGGCTC

TGACTGACCGCGTTACTAAAACAGGTAAGTCCGGCCTCCGCGCCGGGTTT

TGGCGCCTCCCGCGGGCGCCCCCCTCCTCACGGCGAGCGCTGCCACGTCA

GACGAAGGGCGCAGCGAGCGTCCTGATCCTTCCGCCCGGACGCTCAGGAC

AGCGGCCCGCTGCTCATAAGACTCGGCCTTAGAACCCCAGTATCAGCAGA

AGGACATTTTAGGACGGGACTTGGGTGACTCTAGGGCACTGGTTTTCTTT

CCAGAGAGCGGAACAGGCGAGGAAAAGTAGTCCCTTCTCGGCGATTCTGC

GGAGGGATCTCCGTGGGGCGGTGAACGCCGATGATGCCTCTACTAACCAT

GTTCATGTTTTCTTTTTTTTTCTACAGGTCCTGGGTGACGAACAGGGTAC

CGCCACCATGGCCACCGGCTCTCGCACAAGCCTGCTGCTGGCTTTCGGAC

TGCTGTGCCTGCCTTGGCTCCAGGAGGGCTCCGCCGCTAGCATCGATACC

GTCGCTATGTGCTGGAGGCTTGCTGAAGGCTGTATGCTGATAATCACCGC

TGCAGGTTCAGCGTTTTGGCCTCTGACTGACGCTGAACCTGGCGGTGATT

ATCAGGACACAAGGCCTGTTACTAGCACTCACATGGAACAAATGGCCTCT

AGCCTGGAGGCTTGCTGAAGGCTGTATGCTGTTCAATCGCGTATTGGTAA

TCGCGTTTTGGCCTCTGACTGACGCGATTACCAACGCGATTGAACAGGAC

ACAAGGCCTGTTACTAGCACTCACATGGAACAAATGGCCTCTAGCCTGGA

GGCTTGCTGAAGGCTGTATGCTGTGATCATGCTGAAAATGGTGCACGTTT

TGGCCTCTGACTGACGTGCACCATTCAGCATGATCACAGGACACAAGGCC

TGTTACTAGCACTCACATGGAACAAATGGCCTCTCTAGAAT 3'

SEQ ID NO. 18 = SEQ ID NO. 1 + SEQ ID NO. 6
5' AATCAACCTCTGGATTACAAAATTTGTGAAAGATTGACTGGTATTCTT

AACTATGTTGCTCCTTTTACGCTATGTGGATACGCTGCTTTAATGCCTTT

GTATCATGCTATTGCTTCCCGTATGGCTTTCATTTTCTCCTCCTTGTATA

AATCCTGGTTGCTGTCTCTTTATGAGGAGTTGTGGCCCGTTGTCAGGCAA

CGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCC

CTATTGCCACGGCGGAACTCATCGCCGCCTGCCTTGCCCGCTGCTGGACA

GGGGCTCGGCTGTTGGGCACTGACAATTCCGTGGTGTTGTCGGGGAAATC

ATCGTCCTTTCCTTGGCTGCTCGCCTGTGTTGCCACCTGGATTCTGCGCG

GGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTAAGCTTA

TCGATACCGTCGAGATCTAACTTGTTTATTGCAGCTTATAATGGTTACAA

ATAAAGCAATAGCATCACAAATTTCACAAATAAAGCATTTTTTTCACTGC

ATTCTAGTTGTGGTTTGTCCAAACTCATCAATGTATCTTATCATGTCTGG

ATCTCGACCTCGACTAGAGCATGGCTACGTAGATAAGTAGCATGGCGGGT

TAATCATTAACTACAAGGAACCCCTAGTGATGGAGTTGGCCACTCCCTCT

CTGCGCGCTCGCTCGCTCACTGAGGCCGGGCGACCAAAGGTCGCCCGACG

CCCGGGCTTTGCCCGGGCGGCCTCAGTGAGCGAGCGAGCGCGCAGCTGGC

GTAATAGCGAAGAGGCCCGCACCGATCGCCCTTCCCAACAGTTGCGCAGC

CTGAATGGCGAATGGCGATTCCGTTGCAATGGCTGGCGGTAATATTGTTC

TGGATATTACCAGCAAGGCCGATAGTTTGAGTTCTTCTACTCAGGCAAGT

GATGTTATTACTAATCAAAGAAGTATTGCGACAACGGTTAATTTGCGTGA

TGGACAGACTCTTTTACTCGGTGGCCTCACTGATTATAAAAACACTTCTC

AGGATTCTGGCGTACCGTTCCTGTCTAAAATCCCTTTAATCGGCCTCCTG

TTTAGCTCCCGCTCTGATTCTAACGAGGAAAGCACGTTATACGTGCTCGT

CAAAGCAACCATAGTACGCGCCCTGTAGCGGCGCATTAAGCGCGGCGGGT

GTGGTGGTTACGCGCAGCGTGACCGCTACACTTGCCAGCGCCCTAGCGCC

CGCTCCTTTCGCTTTCTTCCCTTCCTTTCTCGCCACGTTCGCCGGCTTTC

CCCGTCAAGCTCTAAATCGGGGGCTCCCTTTAGGGTTCCGATTTAGTGCT

TTACGGCACCTCGACCCCAAAAAACTTGATTAGGGTGATGGTTCACGTAG

TGGGCCATCGCCCTGATAGACGGTTTTTCGCCCTTTGACGTTGGAGTCCA

CGTTCTTTAATAGTGGACTCTTGTTCCAAACTGGAACAACACTCAACCCT

ATCTCGGTCTATTCTTTTGATTTATAAGGGATTTTGCCGATTTCGGCCTA

TTGGTTAAAAAATGAGCTGATTTAACAAAAATTTAACGCGAATTTTAACA

AAATATTAACGTTTACAATTTAAATATTTGCTTATACAATCTTCCTGTTT

TTGGGGCTTTTCTGATTATCAACCGGGGTACATATGATTGACATGCTAGT

TTTACGATTACCGTTCATCGATTCTCTTGTTTGCTCCAGACTCTCAGGCA

ATGACCTGATAGCCTTTGTAGAGACCTCTCAAAAATAGCTACCCTCTCCG

GCATGAATTTATCAGCTAGAACGGTTGAATATCATATTGATGGTGATTTG

ACTGTCTCCGGCCTTTCTCACCCGTTTGAATCTTTACCTACACATTACTC

AGGCATTGCATTTAAAATATATGAGGGTTCTAAAAATTTTTATCCTTGCG

TTGAAATAAAGGCTTCTCCCGCAAAGTATTACAGGGTCATAATGTTTTTT

GGTACAACCGATTTAGCTTTATGCTCTGAGGCTTTATTGCTTAATTTTGC

TAATTCTTTGCCTTGCCTGTATGATTTATTGGATGTTGGAATTCCTGATG

CGGTATTTTCTCCTTACGCATCTGTGCGGTATTTCACACCGCATATGGTG

CACTCTCAGTACAATCTGCTCTGATGCCGCATAGTTAAGCCAGCCCCGAC

ACCCGCCAACACCCGCTGACGCGCCCTGACGGGCTTGTCTGCTCCCGGCA

TCCGCTTACAGACAAGCTGTGACCGTCTCCGGGAGCTGCATGTGTCAGAG

GTTTTCACCGTCATCACCGAAACGCGCGAGACGAAAGGGCCTCGTGATAC

GCCTATTTTTATAGGTTAATGTCATGATAATAATGGTTTCTTAGACGTCA

GGTGGCACTTTCGGGGAAATGTGCGCGGAACCCCTATTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

-continued

TTTCGCCCCGAAGAACGTTTTCCAATGATGAGCACTTTTAAAGTTCTGCT

ATGTGGCGCGGTATTATCCCGTATTGACGCCGGGCAAGAGCAACTCGGTC

GCCGCATACACTATTCTCAGAATGACTTGGTTGAGTACTCACCAGTCACA

GAAAAGCATCTTACGGATGGCATGACAGTAAGAGAATTATGCAGTGCTGC

CATAACCATGAGTGATAACACTGCGGCCAACTTACTTCTGACAACGATCG

GAGGACCGAAGGAGCTAACCGCTTTTTTGCACAACATGGGGGATCATGTA

ACTCGCCTTGATCGTTGGGAACCGGAGCTGAATGAAGCCATACCAAACGA

CGAGCGTGACACCACGATGCCTGTAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT

AAAAGGATCTAGGTGAAGATCCTTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCG

CCTCTCCCCGCGCGTTGGCCGATTCATTAATGCAGCAGCTGCGCGCTCGC

TCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACT

CCATCACTAGGGGTTCCTTGTAGTTAATGATTAACCCGCCATGCTACTTA

TCTACGTAGCCATGCTCTAGGACATTGATTATTGACTAGTGGAGTTCCGC

GTTACATAACTTACGGTAAATGGCCCGCCTGGCTGACCGCCCAACGACCC

CCGCCCATTGACGTCAATAATGACGTATGTTCCCATAGTAACGCCAATAG

GGACTTTCCATTGACGTCAATGGGTGGAGTATTTACGGTAAACTGCCCAC

TTGGCAGTACATCAAGTGTATCATATGCCAAGTACGCCCCCTATTGACGT

CAATGACGGTAAATGGCCCGCCTGGCATTATGCCCAGTACATGACCTTAT

GGGACTTTCCTACTTGGCAGTACATCTACGTATTAGTCATCGCTATTACC

ATGGTCGAGGTGAGCCCCACGTTCTGCTTCACTCTCCCCATCTCCCCCCC

CTCCCCACCCCCAATTTTGTATTTATTTATTTTTTAATTATTTTGTGCAG

CGATGGGGGCGGGGGGGGGGGGGGGCGCGCGCCAGGCGGGGGGGGCGGGG

CGAGGGGCGGGGCGGGGCGAGGCGGAGAGGTGCGGCGGCAGCCAATCAGA

GCGGCGCGCTCCGAAAGTTTCCTTTTATGGCGAGGCGGCGGCGGCGGCGG

CCCTATAAAAAGCGAAGCGCGCGGGGGGGGAGTCGCTGCGCGCTGCCTTC

GCCCCGTGCCCCGCTCCGCCGCCGCCTCGCGCCGCCCGCCCCGGCTCTGA

CTGACCGCGTTACTAAAACAGGTAAGTCCGGCCTCCGCGCCGGGTTTTGG

CGCCTCCCGCGGGCGCCCCCCTCCTCACGGCGAGCGCTGCCACGTCAGAC

GAAGGGCGCAGCGAGCGTCCTGATCCTTCCGCCCGGACGCTCAGGACAGC

GGCCCGCTGCTCATAAGACTCGGCCTTAGAACCCCAGTATCAGCAGAAGG

ACATTTTAGGACGGGACTTGGGTGACTCTAGGGCACTGGTTTTCTTTCCA

GAGAGCGGAACAGGCGAGGAAAAGTAGTCCCTTCTCGGCGATTCTGCGGA

GGGATCTCCGTGGGGCGGTGAACGCCGATGATGCCTCTACTAACCATGTT

CATGTTTTCTTTTTTTTTCTACAGGTCCTGGGTGACGAACAGGGTACCGC

CACCATGGCCACCGGCTCTCGCACAAGCCTGCTGCTGGCTTTCGGACTGC

TGTGCCTGCCTTGGCTCCAGGAGGGCTCCGCCGCTAGCATCGATACCGTC

GCTATGTGCTGGAGGCTTGCTGAAGGCTGTATGCTGAGGTAATATCCTGA

CGCTCAGCCGTTTTGGCCTCTGACTGACGGCTGAGCGTGGATATTACCTC

AGGACACAAGGCCTGTTACTAGCACTCACATGGAACAAATGGCCTCTAGC

CTGGAGGCTTGCTGAAGGCTGTATGCTGTACAGAATCAGATAATCAGCGC

CGTTTTGGCCTCTGACTGACGGCGCTGATTCTGATTCTGTACAGGACACA

AGGCCTGTTACTAGCACTCACATGGAACAAATGGCCTCTAGCCTGGAGGC

TTGCTGAAGGCTGTATGCTGTCATGTTTAAAAATTCGCTGCGCGTTTTGG

CCTCTGACTGACGCGCAGCGAATTTAAACATGACAGGACACAAGGCCTGT

TACTAGCACTCACATGGAACAAATGGCCTCTCTAGAAT 3'

SEQ ID NO. 19 = SEQ ID NO. 1 + SEQ ID NO. 7
5' AATCAACCTCTGGATTACAAAATTTGTGAAAGATTGACTGGTATTCTT

AACTATGTTGCTCCTTTTACGCTATGTGGATACGCTGCTTTAATGCCTTT

GTATCATGCTATTGCTTCCCGTATGGCTTTCATTTTCTCCTCCTTGTATA

AATCCTGGTTGCTGTCTCTTTATGAGGAGTTGTGGCCCGTTGTCAGGCAA

CGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCC

CTATTGCCACGGCGGAACTCATCGCCGCCTGCCTTGCCCGCTGCTGGACA

GGGGCTCGGCTGTTGGGCACTGACAATTCCGTGGTGTTGTCGGGGAAATC

ATCGTCCTTTCCTTGGCTGCTCGCCTGTGTTGCCACCTGGATTCTGCGCG

GGACGTCCTTCTGCTACGTCCCTTCGGCCCTCAATCCAGCGGACCTTCCT

-continued

```
TCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTAAGCTTA

TCGATACCGTCGAGATCTAACTTGTTTATTGCAGCTTATAATGGTTACAA

ATAAAGCAATAGCATCACAAATTTCACAAATAAAGCATTTTTTTCACTGC

ATTCTAGTTGTGGTTTGTCCAAACTCATCAATGTATCTTATCATGTCTGG

ATCTCGACCTCGACTAGAGCATGGCTACGTAGATAAGTAGCATGGCGGGT

TAATCATTAACTACAAGGAACCCCTAGTGATGGAGTTGGCCACTCCCTCT

CTGCGCGCTCGCTCGCTCACTGAGGCCGGGCGACCAAAGGTCGCCCGACG

CCCGGGCTTTGCCCGGGCGGCCTCAGTGAGCGAGCGAGCGCGCAGCTGGC

GTAATAGCGAAGAGGCCCGCACCGATCGCCCTTCCCAACAGTTGCGCAGC

CTGAATGGCGAATGGCGATTCCGTTGCAATGGCTGGCGGTAATATTGTTC

TGGATATTACCAGCAAGGCCGATAGTTTGAGTTCTTCTACTCAGGCAAGT

GATGTTATTACTAATCAAAGAAGTATTGCGACAACGGTTAATTTGCGTGA

TGGACAGACTCTTTTACTCGGTGGCCTCACTGATTATAAAAACACTTCTC

AGGATTCTGGCGTACCGTTCCTGTCTAAAATCCCTTTAATCGGCCTCCTG

TTTAGCTCCCGCTCTGATTCTAACGAGGAAAGCACGTTATACGTGCTCGT

CAAAGCAACCATAGTACGCGCCCTGTAGCGGCGCATTAAGCGCGGCGGGT

GTGGTGGTTACGCGCAGCGTGACCGCTACACTTGCCAGCGCCCTAGCGCC

CGCTCCTTTCGCTTTCTTCCCTTCCTTTCTCGCCACGTTCGCCGGCTTTC

CCCGTCAAGCTCTAAATCGGGGGCTCCCTTTAGGGTTCCGATTTAGTGCT

TTACGGCACCTCGACCCCAAAAAACTTGATTAGGGTGATGGTTCACGTAG

TGGGCCATCGCCCTGATAGACGGTTTTTCGCCCTTTGACGTTGGAGTCCA

CGTTCTTTAATAGTGGACTCTTGTTCCAAACTGGAACAACACTCAACCCT

ATCTCGGTCTATTCTTTTGATTTATAAGGGATTTTGCCGATTTCGGCCTA

TTGGTTAAAAAATGAGCTGATTTAACAAAAATTTAACGCGAATTTTAACA

AAATATTAACGTTTACAATTTAAATATTTGCTTATACAATCTTCCTGTTT

TTGGGGCTTTTCTGATTATCAACCGGGGTACATATGATTGACATGCTAGT

TTTACGATTACCGTTCATCGATTCTCTTGTTTGCTCCAGACTCTCAGGCA

ATGACCTGATAGCCTTTGTAGAGACCTCTCAAAAATAGCTACCCTCTCCG

GCATGAATTTATCAGCTAGAACGGTTGAATATCATATTGATGGTGATTTG

ACTGTCTCCGGCCTTTCTCACCCGTTTGAATCTTTACCTACACATTACTC

AGGCATTGCATTTAAAATATATGAGGGTTCTAAAAATTTTTATCCTTGCG

TTGAAATAAAGGCTTCTCCCGCAAAAGTATTACAGGGTCATAATGTTTTT

GGTACAACCGATTTAGCTTTATGCTCTGAGGCTTTATTGCTTAATTTTGC

TAATTCTTTGCCTTGCCTGTATGATTTATTGGATGTTGGAATTCCTGATG

CGGTATTTTCTCCTTACGCATCTGTGCGGTATTTCACACCGCATATGGTG

CACTCTCAGTACAATCTGCTCTGATGCCGCATAGTTAAGCCAGCCCCGAC

ACCCGCCAACACCCGCTGACGCGCCCTGACGGGCTTGTCTGCTCCCGGCA

TCCGCTTACAGACAAGCTGTGACCGTCTCCGGGAGCTGCATGTGTCAGAG

GTTTTCACCGTCATCACCGAAACGCGCGAGACGAAAGGGCCTCGTGATAC

GCCTATTTTTATAGGTTAATGTCATGATAATAATGGTTTCTTAGACGTCA
```

-continued

```
GGTGGCACTTTTCGGGGAAATGTGCGCGGAACCCCTATTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

TTTCGCCCCGAAGAACGTTTTCCAATGATGAGCACTTTTAAAGTTCTGCT

ATGTGGCGCGGTATTATCCCGTATTGACGCCGGGCAAGAGCAACTCGGTC

GCCGCATACACTATTCTCAGAATGACTTGGTTGAGTACTCACCAGTCACA

GAAAAGCATCTTACGGATGGCATGACAGTAAGAGAATTATGCAGTGCTGC

CATAACCATGAGTGATAACACTGCGGCCAACTTACTTCTGACAACGATCG

GAGGACCGAAGGAGCTAACCGCTTTTTTGCACAACATGGGGGATCATGTA

ACTCGCCTTGATCGTTGGGAACCGGAGCTGAATGAAGCCATACCAAACGA

CGAGCGTGACACCACGATGCCTGTAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT

AAAAGGATCTAGGTGAAGATCCTTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCG

CCTCTCCCCGCGCGTTGGCCGATTCATTAATGCAGCAGCTGCGCGCTCGC
```

-continued

```
TCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACT

CCATCACTAGGGGTTCCTTGTAGTTAATGATTAACCCGCCATGCTACTTA

TCTACGTAGCCATGCTCTAGGACATTGATTATTGACTAGTGGAGTTCCGC

GTTACATAACTTACGGTAAATGGCCCGCCTGGCTGACCGCCCAACGACCC

CCGCCCATTGACGTCAATAATGACGTATGTTCCCATAGTAACGCCAATAG

GGACTTTCCATTGACGTCAATGGGTGGAGTATTTACGGTAAACTGCCCAC

TTGGCAGTACATCAAGTGTATCATATGCCAAGTACGCCCCCTATTGACGT

CAATGACGGTAAATGGCCCGCCTGGCATTATGCCCAGTACATGACCTTAT

GGGACTTTCCTACTTGGCAGTACATCTACGTATTAGTCATCGCTATTACC

ATGGTCGAGGTGAGCCCCACGTTCTGCTTCACTCTCCCCATCTCCCCCCC

CTCCCCACCCCCAATTTTGTATTTATTTATTTTTTAATTATTTTGTGCAG

CGATGGGGGCGGGGGGGGGGGGGGCGCGCGCCAGGCGGGGCGGGGGGGG

GCGAGGGGCGGGGCGGGGCGAGGCGGAGAGGTGCGGCGGCAGCCAATCAG

AGCGGCGCGCTCCGAAAGTTTCCTTTTATGGCGAGGCGGCGGCGGCGGCG

GCCCTATAAAAAGCGAAGCGCGCGGCGGGCGGGAGTCGCTGCGCGCTGCC

TTCGCCCCGTGCCCCGCTCCGCCGCCGCCTCGCGCCGCCCGCCCCGGCTC

TGACTGACCGCGTTACTAAAACAGGTAAGTCCGGCCTCCGCGCCGGGTTT

TGGCGCCTCCCGCGGGCGCCCCCCTCCTCACGGCGAGCGCTGCCACGTCA

GACGAAGGGCGCAGCGAGCGTCCTGATCCTTCCGCCCGGACGCTCAGGAC

AGCGGCCCGCTGCTCATAAGACTCGGCCTTAGAACCCCAGTATCAGCAGA

AGGACATTTTAGGACGGGACTTGGGTGACTCTAGGGCACTGGTTTTCTTT

CCAGAGAGCGGAACAGGCGAGGAAAAGTAGTCCCTTCTCGGCGATTCTGC

GGAGGGATCTCCGTGGGGCGGTGAACGCCGATGATGCCTCTACTAACCAT

GTTCATGTTTTCTTTTTTTTTCTACAGGTCCTGGGTGACGAACAGGGTAC

CGCCACCATGGCCACCGGCTCTCGCACAAGCCTGCTGCTGGCTTTCGGAC

TGCTGTGCCTGCCTTGGCTCCAGGAGGGCTCCGCCGCTAGCATCGATACC

GTCGCTATGTGCTGGAGGCTTGCTGAAGGCTGTATGCTGATGAATCGGGT

TGTCTGAATCGCGTTTTGGCCTCTGACTGACGCGATTCAGAACCCGATTC

ATCAGGACACAAGGCCTGTTACTAGCACTCACATGGAACAAATGGCCTCT

AGCCTGGAGGCTTGCTGAAGGCTGTATGCTGAACACTTTGCTATATCATC

CTGCGTTTTGGCCTCTGACTGACGCAGGATGATAGCAAAGTGTTCAGGAC

ACAAGGCCTGTTACTAGCACTCACATGGAACAAATGGCCTCTAGCCTGGA

GGCTTGCTGAAGGCTGTATGCTGTTCTGTTCGTTAAGCTAATGCTCGTTT

TGGCCTCTGACTGACGAGCATTAGCAACGAACAGAACAGGACACAAGGCC

TGTTACTAGCACTCACATGGAACAAATGGCCTCTCTAGAAT 3'
```

SEQ ID NO. 20 = SEQ ID NO. 1 + SEQ ID NO. 8

```
5' AATCAACCTCTGGATTACAAAATTTGTGAAAGATTGACTGGTATTCTT

AACTATGTTGCTCCTTTTACGCTATGTGGATACGCTGCTTTAATGCCTTT

GTATCATGCTATTGCTTCCCGTATGGCTTTCATTTTCTCCTCCTTGTATA

AATCCTGGTTGCTGTCTCTTTATGAGGAGTTGTGGCCCGTTGTCAGGCAA
```

-continued

```
CGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCC

CTATTGCCACGGCGGAACTCATCGCCGCCTGCCTTGCCCGCTGCTGGACA

GGGGCTCGGCTGTTGGGCACTGACAATTCCGTGGTGTTGTCGGGGAAATC

ATCGTCCTTTCCTTGGCTGCTCGCCTGTGTTGCCACCTGGATTCTGCGCG

GGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTAAGCTTA

TCGATACCGTCGAGATCTAACTTGTTTATTGCAGCTTATAATGGTTACAA

ATAAAGCAATAGCATCACAAATTTCACAAATAAAGCATTTTTTTCACTGC

ATTCTAGTTGTGGTTTGTCCAAACTCATCAATGTATCTTATCATGTCTGG

ATCTCGACCTCGACTAGAGCATGGCTACGTAGATAAGTAGCATGGCGGGT

TAATCATTAACTACAAGGAACCCCTAGTGATGGAGTTGGCCACTCCCTCT

CTGCGCGCTCGCTCGCTCACTGAGGCCGGGCGACCAAAGGTCGCCCGACG

CCCGGGCTTTGCCCGGGCGGCCTCAGTGAGCGAGCGAGCGCGCAGCTGGC

GTAATAGCGAAGAGGCCCGCACCGATCGCCCTTCCCAACAGTTGCGCAGC

CTGAATGGCGAATGGCGATTCCGTTGCAATGGCTGGCGGTAATATTGTTC

TGGATATTACCAGCAAGGCCGATAGTTTGAGTTCTTCTACTCAGGCAAGT

GATGTTATTACTAATCAAAGAAGTATTGCGACAACGGTTAATTTGCGTGA

TGGACAGACTCTTTTACTCGGTGGCCTCACTGATTATAAAAACACTTCTC

AGGATTCTGGCGTACCGTTCCTGTCTAAAATCCCTTTAATCGGCCTCCTG

TTTAGCTCCCGCTCTGATTCTAACGAGGAAAGCACGTTATACGTGCTCGT

CAAAGCAACCATAGTACGCGCCCTGTAGCGGCGCATTAAGCGCGGCGGGT

GTGGTGGTTACGCGCAGCGTGACCGCTACACTTGCCAGCGCCCTAGCGCC

CGCTCCTTTCGCTTTCTTCCCTTCCTTTCTCGCCACGTTCGCCGGCTTTC

CCCGTCAAGCTCTAAATCGGGGGCTCCCTTTAGGGTTCCGATTTAGTGCT

TTACGGCACCTCGACCCCAAAAAACTTGATTAGGGTGATGGTTCACGTAG

TGGGCCATCGCCCTGATAGACGGTTTTTCGCCCTTTGACGTTGGAGTCCA

CGTTCTTTAATAGTGGACTCTTGTTCCAAACTGGAACAACACTCAACCCT

ATCTCGGTCTATTCTTTTGATTTATAAGGGATTTTGCCGATTTCGGCCTA

TTGGTTAAAAAATGAGCTGATTTAACAAAAATTTAACGCGAATTTTAACA

AAATATTAACGTTTACAATTTAAATATTTGCTTATACAATCTTCCTGTTT

TTGGGGCTTTTCTGATTATCAACCGGGGTACATATGATTGACATGCTAGT

TTTACGATTACCGTTCATCGATTCTCTTGTTTGCTCCAGACTCTCAGGCA

ATGACCTGATAGCCTTTGTAGAGACCTCTCAAAAATAGCTACCCTCTCCG

GCATGAATTTATCAGCTAGAACGGTTGAATATCATATTGATGGTGATTTG

ACTGTCTCCGGCCTTTCTCACCCGTTTGAATCTTTACCTACACATTACTC

AGGCATTGCATTTAAAATATATGAGGGTTCTAAAAATTTTTATCCTTGCG

TTGAAATAAAGGCTTCTCCCGCAAAAGTATTACAGGGTCATAATGTTTTT

GGTACAACCGATTTAGCTTTATGCTCTGAGGCTTTATTGCTTAATTTTGC

TAATTCTTTGCCTTGCCTGTATGATTTATTGGATGTTGGAATTCCTGATG
```

CGGTATTTTCTCCTTACGCATCTGTGCGGTATTTCACACCGCATATGGTG

CACTCTCAGTACAATCTGCTCTGATGCCGCATAGTTAAGCCAGCCCCGAC

ACCCGCCAACACCCGCTGACGCGCCCTGACGGGCTTGTCTGCTCCCGGCA

TCCGCTTACAGACAAGCTGTGACCGTCTCCGGGAGCTGCATGTGTCAGAG

GTTTTCACCGTCATCACCGAAACGCGCGAGACGAAAGGGCCTCGTGATAC

GCCTATTTTTATAGGTTAATGTCATGATAATAATGGTTTCTTAGACGTCA

GGTGGCACTTTTCGGGGAAATGTGCGCGGAACCCCTATTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

TTTCGCCCCGAAGAACGTTTTCCAATGATGAGCACTTTTAAAGTTCTGCT

ATGTGGCGCGGTATTATCCCGTATTGACGCCGGGCAAGAGCAACTCGGTC

GCCGCATACACTATTCTCAGAATGACTTGGTTGAGTACTCACCAGTCACA

GAAAAGCATCTTACGGATGGCATGACAGTAAGAGAATTATGCAGTGCTGC

CATAACCATGAGTGATAACACTGCGGCCAACTTACTTCTGACAACGATCG

GAGGACCGAAGGAGCTAACCGCTTTTTTGCACAACATGGGGGATCATGTA

ACTCGCCTTGATCGTTGGGAACCGGAGCTGAATGAAGCCATACCAAACGA

CGAGCGTGACACCACGATGCCTGTAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT

AAAAGGATCTAGGTGAAGATCCTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCG

CCTCTCCCCGCGCGTTGGCCGATTCATTAATGCAGCAGCTGCGCGCTCGC

TCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACT

CCATCACTAGGGGTTCCTTGTAGTTAATGATTAACCCGCCATGCTACTTA

TCTACGTAGCCATGCTCTAGGACATTGATTATTGACTAGTGGAGTTCCGC

GTTACATAACTTACGGTAAATGGCCCGCCTGGCTGACCGCCCAACGACCC

CCGCCCATTGACGTCAATAATGACGTATGTTCCCATAGTAACGCCAATAG

GGACTTTCCATTGACGTCAATGGGTGGAGTATTTACGGTAAACTGCCCAC

TTGGCAGTACATCAAGTGTATCATATGCCAAGTACGCCCCCTATTGACGT

CAATGACGGTAAATGGCCCGCCTGGCATTATGCCCAGTACATGACCTTAT

GGGACTTTCCTACTTGGCAGTACATCTACGTATTAGTCATCGCTATTACC

ATGGTCGAGGTGAGCCCCACGTTCTGCTTCACTCTCCCCATCTCCCCCCC

CTCCCCACCCCCAATTTTGTATTTATTTATTTTTTAATTATTTTGTGCAG

CGATGGGGGCGGGGGGGGGGGGGGGCGCGCGCCAGGCGGGGCGGGGGGGG

GCGAGGGGCGGGGGGGGCGAGGCGGAGAGGTGCGGCGGCAGCCAATCAGA

GCGGCGCGCTCCGAAAGTTTCCTTTTATGGCGAGGCGGCGGCGGCGGCGG

CCCTATAAAAAGCGAAGCGCGCGGCGGGCGGGAGTCGCTGCGCGCTGCCT

TCGCCCCGTGCCCCGCTCCGCCGCCGCCTCGCGCCGCCCGCCCCGGCTCT

GACTGACCGCGTTACTAAAACAGGTAAGTCCGGCCTCCGCGCCGGGTTTT

GGCGCCTCCCGCGGGCGCCCCCCTCCTCACGGCGAGCGCTGCCACGTCAG

ACGAAGGGCGCAGCGAGCGTCCTGATCCTTCCGCCCGGACGCTCAGGACA

GCGGCCCGCTGCTCATAAGACTCGGCCTTAGAACCCCAGTATCAGCAGAA

GGACATTTTAGGACGGGACTTGGGTGACTCTAGGGCACTGGTTTTCTTTC

CAGAGAGCGGAACAGGCGAGGAAAGTAGTCCCTTCTCGGCGATTCTGCG

GAGGGATCTCCGTGGGGCGGTGAACGCCGATGATGCCTCTACTAACCATG

TTCATGTTTTCTTTTTTTTTCTACAGGTCCTGGGTGACGAACAGGGTACC

GCCACCATGGCCACCGGCTCTCGCACAAGCCTGCTGCTGGCTTTCGGACT

GCTGTGCCTGCCTTGGCTCCAGGAGGGCTCCGCCGCTAGCATCGATACCG

TCGCTATGTGCTGGAGGCTTGCTGAAGGCTGTATGCTGGAGCATTAGCAA

TGCGAACAGAAGTTTTGGCCTCTGACTGACTTCTGTTCGTTGCTAATGCT

CCAGGACACAAGGCCTGTTACTAGCACTCACATGGAACAAATGGCCTCTA

GCCTGGAGGCTTGCTGAAGGCTGTATGCTGAAACATAATGGATTCAGCAG

CGCGTTTTGGCCTCTGACTGACGCGCTGCTGACCATTATGTTTCAGGACA

CAAGGCCTGTTACTAGCACTCACATGGAACAAATGGCCTCTAGCCTGGAG

-continued

GCTTGCTGAAGGCTGTATGCTGTTATCTTTGCGAAGCTGCCATCCGTTTT

GGCCTCTGACTGACGGATGGCAGCCGCAAAGATAACAGGACACAAGGCCT

GTTACTAGCACTCACATGGAACAAATGGCCTCTCTAGAAT 3'

SEQ ID NO. 21 = SEQ ID NO. 1 + SEQ ID NO. 9
5' AATCAACCTCTGGATTACAAAATTTGTGAAAGATTGACTGGTATTCTT

AACTATGTTGCTCCTTTTACGCTATGTGGATACGCTGCTTTAATGCCTTT

GTATCATGCTATTGCTTCCCGTATGGCTTTCATTTTCTCCTCCTTGTATA

AATCCTGGTTGCTGTCTCTTTATGAGGAGTTGTGGCCCGTTGTCAGGCAA

CGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCC

CTATTGCCACGGCGGAACTCATCGCCGCCTGCCTTGCCCGCTGCTGGACA

GGGGCTCGGCTGTTGGGCACTGACAATTCCGTGGTGTTGTCGGGGAAATC

ATCGTCCTTTCCTTGGCTGCTCGCCTGTGTTGCCACCTGGATTCTGCGCG

GGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTAAGCTTA

TCGATACCGTCGAGATCTAACTTGTTTATTGCAGCTTATAATGGTTACAA

ATAAAGCAATAGCATCACAAATTTCACAAATAAAGCATTTTTTTCACTGC

ATTCTAGTTGTGGTTTGTCCAAACTCATCAATGTATCTTATCATGTCTGG

ATCTCGACCTCGACTAGAGCATGGCTACGTAGATAAGTAGCATGGCGGGT

TAATCATTAACTACAAGGAACCCCTAGTGATGGAGTTGGCCACTCCCTCT

CTGCGCGCTCGCTCGCTCACTGAGGCCGGGCGACCAAAGGTCGCCCGACG

CCCGGGCTTTGCCCGGGCGGCCTCAGTGAGCGAGCGAGCGCGCAGCTGGC

GTAATAGCGAAGAGGCCCGCACCGATCGCCCTTCCCAACAGTTGCGCAGC

CTGAATGGCGAATGGCGATTCCGTTGCAATGGCTGGCGGTAATATTGTTC

TGGATATTACCAGCAAGGCCGATAGTTTGAGTTCTTCTACTCAGGCAAGT

GATGTTATTACTAATCAAAGAAGTATTGCGACAACGGTTAATTTGCGTGA

TGGACAGACTCTTTTACTCGGTGGCCTCACTGATTATAAAAACACTTCTC

AGGATTCTGGCGTACCGTTCCTGTCTAAAATCCCTTTAATCGGCCTCCTG

TTTAGCTCCCGCTCTGATTCTAACGAGGAAAGCACGTTATACGTGCTCGT

CAAAGCAACCATAGTACGCGCCCTGTAGCGGCGCATTAAGCGCGGCGGGT

GTGGTGGTTACGCGCAGCGTGACCGCTACACTTGCCAGCGCCCTAGCGCC

CGCTCCTTTCGCTTTCTTCCCTTCCTTTCTCGCCACGTTCGCCGGCTTTC

CCCGTCAAGCTCTAAATCGGGGGCTCCCTTTAGGGTTCCGATTTAGTGCT

TTACGGCACCTCGACCCCAAAAAACTTGATTAGGGTGATGGTTCACGTAG

TGGGCCATCGCCCTGATAGACGGTTTTTCGCCCTTTGACGTTGGAGTCCA

CGTTCTTTAATAGTGGACTCTTGTTCCAAACTGGAACAACACTCAACCCT

ATCTCGGTCTATTCTTTTGATTTATAAGGGATTTTGCCGATTTCGGCCTA

TTGGTTAAAAAATGAGCTGATTTAACAAAAATTTAACGCGAATTTTAACA

AAATATTAACGTTTACAATTTAAATATTTGCTTATACAATCTTCCTGTTT

TTGGGGCTTTTCTGATTATCAACCGGGGTACATATGATTGACATGCTAGT

-continued

TTTACGATTACCGTTCATCGATTCTCTTGTTTGCTCCAGACTCTCAGGCA

ATGACCTGATAGCCTTTGTAGAGACCTCTCAAAAATAGCTACCCTCTCCG

GCATGAATTTATCAGCTAGAACGGTTGAATATCATATTGATGGTGATTTG

ACTGTCTCCGGCCTTTCTCACCCGTTTGAATCTTTACCTACACATTACTC

AGGCATTGCATTTAAAATATATGAGGGTTCTAAAAATTTTTATCCTTGCG

TTGAAATAAAGGCTTCTCCCGCAAAAGTATTACAGGGTCATAATGTTTTT

GGTACAACCGATTTAGCTTTATGCTCTGAGGCTTTATTGCTTAATTTTGC

TAATTCTTTGCCTTGCCTGTATGATTTATTGGATGTTGGAATTCCTGATG

CGGTATTTTCTCCTTACGCATCTGTGCGGTATTTCACACCGCATATGGTG

CACTCTCAGTACAATCTGCTCTGATGCCGCATAGTTAAGCCAGCCCCGAC

ACCCGCCAACACCCGCTGACGCGCCCTGACGGGCTTGTCTGCTCCCGGCA

TCCGCTTACGACAAGCTGTGACCGTCTCCGGGAGCTGCATGTGTCAGAG

GTTTTCACCGTCATCACCGAAACGCGCGAGACGAAAGGGCCTCGTGATAC

GCCTATTTTTATAGGTTAATGTCATGATAATAATGGTTTCTTAGACGTCA

GGTGGCACTTTTCGGGGAAATGTGCGCGGAACCCCTATTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

TTTCGCCCCGAAGAACGTTTTCCAATGATGAGCACTTTTAAAGTTCTGCT

ATGTGGCGCGGTATTATCCCGTATTGACGCCGGGCAAGAGCAACTCGGTC

GCCGCATACACTATTCTCAGAATGACTTGGTTGAGTACTCACCAGTCACA

GAAAAGCATCTTACGGATGGCATGACAGTAAGAGAATTATGCAGTGCTGC

CATAACCATGAGTGATAACACTGCGGCCAACTTACTTCTGACAACGATCG

GAGGACCGAAGGAGCTAACCGCTTTTTTGCACAACATGGGGGATCATGTA

ACTCGCCTTGATCGTTGGGAACCGGAGCTGAATGAAGCCATACCAAACGA

CGAGCGTGACACCACGATGCCTGTAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT

AAAAGGATCTAGGTGAAGATCCTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCG

CCTCTCCCCGCGCGTTGGCCGATTCATTAATGCAGCAGCTGCGCGCTCGC

TCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACT

CCATCACTAGGGGTTCCTTGTAGTTAATGATTAACCCGCCATGCTACTTA

TCTACGTAGCCATGCTCTAGGACATTGATTATTGACTAGTGGAGTTCCGC

GTTACATAACTTACGGTAAATGGCCCGCCTGGCTGACCGCCCAACGACCC

CCGCCCATTGACGTCAATAATGACGTATGTTCCCATAGTAACGCCAATAG

GGACTTTCCATTGACGTCAATGGGTGGAGTATTTACGGTAAACTGCCCAC

TTGGCAGTACATCAAGTGTATCATATGCCAAGTACGCCCCCTATTGACGT

CAATGACGGTAAATGGCCCGCCTGGCATTATGCCCAGTACATGACCTTAT

GGGACTTTCCTACTTGGCAGTACATCTACGTATTAGTCATCGCTATTACC

ATGGTCGAGGTGAGCCCCACGTTCTGCTTCACTCTCCCCATCTCCCCCCC

CTCCCCACCCCCAATTTTGTATTTATTTATTTTTTAATTATTTTGTGCAG

CGATGGGGGCGGGGGGGGGGGGGGCGCGCGCCAGGCGGGGCGGGGGGGG

GCGAGGGGCGGGGCGGGGCGAGGCGGAGAGGTGCGGCGGCAGCCAATCAG

AGCGGCGCGCTCCGAAAGTTTCCTTTTATGGCGAGGCGGCGGCGGCGGCG

GCCCTATAAAAAGCGAAGCGCGCGGCGGGCGGGAGTCGCTGCGCGCTGCC

TTCGCCCCGTGCCCCGCTCCGCCGCCGCCTCGCGCCGCCCGCCCCGGCTC

TGACTGACCGCGTTACTAAAACAGGTAAGTCCGGCCTCCGCGCCGGGTTT

TGGCGCCTCCCGCGGGCGCCCCCCTCCTCACGGCGAGCGCTGCCACGTCA

GACGAAGGGCGCAGCGAGCGTCCTGATCCTTCCGCCCGGACGCTCAGGAC

AGCGGCCCGCTGCTCATAAGACTCGGCCTTAGAACCCCAGTATCAGCAGA

AGGACATTTTAGGACGGGACTTGGGTGACTCTAGGGCACTGGTTTTCTTT

CCAGAGAGCGGAACAGGCGAGGAAAAGTAGTCCCTTCTCGGCGATTCTGC

GGAGGGATCTCCGTGGGGCGGTGAACGCCGATGATGCCTCTACTAACCAT

GTTCATGTTTTCTTTTTTTTTCTACAGGTCCTGGGTGACGAACAGGGTAC

CGCCACCATGGCCACCGGCTCTCGCACAAGCCTGCTGCTGGCTTTCGGAC

TGCTGTGCCTGCCTTGGCTCCAGGAGGGCTCCGCCGCTAGCATCGATACC

GTCGCTATGTGCTGGAGGCTTGCTGAAGGCTGTATGCTGGCTCCTCCACT

TGGTGGTTTGGTTTTGGCCTCTGACTGACGCGGCAACATTCTGGTGATTA

CAGGACACAAGGCCTGTTACTAGCACTCACATGGAACAAATGGCCTCTAG

CCTGGAGGCTTGCTGAAGGCTGTATGCTGTCATAATCGCTATTTGGTGCG

GCGTTTTGGCCTCTGACTGACGCCGCACCAAAGCGATTATGACAGGACAC

AAGGCCTGTTACTAGCACTCACATGGAACAAATGGCCTCTAGCCTGGAGG

CTTGCTGAAGGCTGTATGCTGTTCTGATCCTGAAGTTCGGGTTCGTTTTG

GCCTCTGACTGACGAACCCGAACCAGGATCAGAACAGGACACAAGGCCTG

TTACTAGCACTCACATGGAACAAATGGCCTCTCTAGAAT 3'

SEQ ID NO. 22 = SEQ ID NO. 1 + SEQ ID NO. 10
5' AATCAACCTCTGGATTACAAAATTTGTGAAAGATTGACTGGTATTCTT

AACTATGTTGCTCCTTTTACGCTATGTGGATACGCTGCTTTAATGCCTTT

GTATCATGCTATTGCTTCCCGTATGGCTTTCATTTTCTCCTCCTTGTATA

AATCCTGGTTGCTGTCTCTTTATGAGGAGTTGTGGCCCGTTGTCAGGCAA

CGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCC

CTATTGCCACGGCGGAACTCATCGCCGCCTGCCTTGCCCGCTGCTGGACA

GGGGCTCGGCTGTTGGGCACTGACAATTCCGTGGTGTTGTCGGGGAAATC

ATCGTCCTTTCCTTGGCTGCTCGCCTGTGTTGCCACCTGGATTCTGCGCG

GGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTAAGCTTA

TCGATACCGTCGAGATCTAACTTGTTTATTGCAGCTTATAATGGTTACAA

ATAAAGCAATAGCATCACAAATTTCACAAATAAAGCATTTTTTTCACTGC

ATTCTAGTTGTGGTTTGTCCAAACTCATCAATGTATCTTATCATGTCTGG

ATCTCGACCTCGACTAGAGCATGGCTACGTAGATAAGTAGCATGGCGGGT

TAATCATTAACTACAAGGAACCCCTAGTGATGGAGTTGGCCACTCCCTCT

CTGCGCGCTCGCTCGCTCACTGAGGCCGGGCGACCAAAGGTCGCCCGACG

CCCGGGCTTTGCCCGGGCGGCCTCAGTGAGCGAGCGAGCGCGCAGCTGGC

GTAATAGCGAAGAGGCCCGCACCGATCGCCCTTCCCAACAGTTGCGCAGC

CTGAATGGCGAATGGCGATTCCGTTGCAATGGCTGGCGGTAATATTGTTC

TGGATATTACCAGCAAGGCCGATAGTTTGAGTTCTTCTACTCAGGCAAGT

GATGTTATTACTAATCAAAGAAGTATTGCGACAACGGTTAATTTGCGTGA

TGGACAGACTCTTTTACTCGGTGGCCTCACTGATTATAAAAACACTTCTC

AGGATTCTGGCGTACCGTTCCTGTCTAAAATCCCTTTAATCGGCCTCCTG

TTTAGCTCCCGCTCTGATTCTAACGAGGAAAGCACGTTATACGTGCTCGT

CAAAGCAACCATAGTACGCGCCCTGTAGCGGCGCATTAAGCGCGGCGGGT

GTGGTGGTTACGCGCAGCGTGACCGCTACACTTGCCAGCGCCCTAGCGCC

CGCTCCTTTCGCTTTCTTCCCTTCCTTTCTCGCCACGTTCGCCGGCTTTC

CCCGTCAAGCTCTAAATCGGGGGCTCCCTTTAGGGTTCCGATTTAGTGCT

TTACGGCACCTCGACCCCAAAAAACTTGATTAGGGTGATGGTTCACGTAG

-continued

```
TGGGCCATCGCCCTGATAGACGGTTTTTCGCCCTTTGACGTTGGAGTCCA

CGTTCTTTAATAGTGGACTCTTGTTCCAAACTGGAACAACACTCAACCCT

ATCTCGGTCTATTCTTTTGATTTATAAGGGATTTTGCCGATTTCGGCCTA

TTGGTTAAAAAATGAGCTGATTTAACAAAAATTTAACGCGAATTTTAACA

AAATATTAACGTTTACAATTTAAATATTTGCTTATACAATCTTCCTGTTT

TTGGGGCTTTTCTGATTATCAACCGGGGTACATATGATTGACATGCTAGT

TTTACGATTACCGTTCATCGATTCTCTTGTTTGCTCCAGACTCTCAGGCA

ATGACCTGATAGCCTTTGTAGAGACCTCTCAAAAATAGCTACCCTCTCCG

GCATGAATTTATCAGCTAGAACGGTTGAATATCATATTGATGGTGATTTG

ACTGTCTCCGGCCTTTCTCACCCGTTTGAATCTTTACCTACACATTACTC

AGGCATTGCATTTAAAATATATGAGGGTTCTAAAAATTTTTATCCTTGCG

TTGAAATAAAGGCTTCTCCCGCAAAAGTATTACAGGGTCATAATGTTTTT

GGTACAACCGATTTAGCTTTATGCTCTGAGGCTTTATTGCTTAATTTTGC

TAATTCTTTGCCTTGCCTGTATGATTTATTGGATGTTGGAATTCCTGATG

CGGTATTTTCTCCTTACGCATCTGTGCGGTATTTCACACCGCATATGGTG

CACTCTCAGTACAATCTGCTCTGATGCCGCATAGTTAAGCCAGCCCCGAC

ACCCGCCAACACCCGCTGACGCGCCCTGACGGGCTTGTCTGCTCCCGGCA

TCCGCTTACAGACAAGCTGTGACCGTCTCCGGGAGCTGCATGTGTCAGAG

GTTTTCACCGTCATCACCGAAACGCGCGAGACGAAAGGGCCTCGTGATAC

GCCTATTTTTATAGGTTAATGTCATGATAATAATGGTTTCTTAGACGTCA

GGTGGCACTTTTCGGGGAAATGTGCGCGGAACCCCTATTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

TTTCGCCCCGAAGAACGTTTTCCAATGATGAGCACTTTTAAAGTTCTGCT

ATGTGGCGCGGTATTATCCCGTATTGACGCCGGGCAAGAGCAACTCGGTC

GCCGCATACACTATTCTCAGAATGACTTGGTTGAGTACTCACCAGTCACA

GAAAAGCATCTTACGGATGGCATGACAGTAAGAGAATTATGCAGTGCTGC

CATAACCATGAGTGATAACACTGCGGCCAACTTACTTCTGACAACGATCG

GAGGACCGAAGGAGCTAACCGCTTTTTTGCACAACATGGGGGATCATGTA

ACTCGCCTTGATCGTTGGGAACCGGAGCTGAATGAAGCCATACCAAACGA

CGAGCGTGACACCACGATGCCTGTAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT
```

-continued

```
AAAAGGATCTAGGTGAAGATCCTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCG

CCTCTCCCCGCGCGTTGGCCGATTCATTAATGCAGCAGCTGCGCGCTCGC

TCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACT

CCATCACTAGGGGTTCCTTGTAGTTAATGATTAACCCGCCATGCTACTTA

TCTACGTAGCCATGCTCTAGGACATTGATTATTGACTAGTGGAGTTCCGC

GTTACATAACTTACGGTAAATGGCCCGCCTGGCTGACCGCCCAACGACCC

CCGCCCATTGACGTCAATAATGACGTATGTTCCCATAGTAACGCCAATAG

GGACTTTCCATTGACGTCAATGGGTGGAGTATTTACGGTAAACTGCCCAC

TTGGCAGTACATCAAGTGTATCATATGCCAAGTACGCCCCCTATTGACGT

CAATGACGGTAAATGGCCCGCCTGGCATTATGCCCAGTACATGACCTTAT

GGGACTTTCCTACTTGGCAGTACATCTACGTATTAGTCATCGCTATTACC

ATGGTCGAGGTGAGCCCCACGTTCTGCTTCACTCTCCCCATCTCCCCCCC

CTCCCCACCCCCAATTTTGTATTTATTTATTTTTTAATTATTTTGTGCAG

CGATGGGGGCGGGGGGGGGGGGGGCGCGCGCCAGGCGGGGCGGGGGGGG

GCGAGGGGCGGGGCGGGGCGAGGCGGAGAGGTGCGGCGGCAGCCAATCAG

AGCGGCGCGCTCCGAAAGTTTCCTTTTATGGCGAGGCGGCGGCGGCGGCG

GCCCTATAAAAAGCGAAGCGCGCGGCGGGCGGGAGTCGCTGCGCGCTGCC

TTCGCCCCGTGCCCCGCTCCGCCGCCGCCTCGCGCCGCCCGCCCCGGCTC

TGACTGACCGCGTTACTAAAACAGGTAAGTCCGGCCTCCGCGCCGGGTTT

TGGCGCCTCCCGCGGGCGCCCCCCTCCTCACGGCGAGCGCTGCCACGTCA

GACGAAGGGCGCAGCGAGCGTCCTGATCCTTCCGCCCGGACGCTCAGGAC

AGCGGCCCGCTGCTCATAAGACTCGGCCTTAGAACCCCAGTATCAGCAGA
```

-continued

AGGACATTTTAGGACGGGACTTGGGTGACTCTAGGGCACTGGTTTTCTTT

CCAGAGAGCGGAACAGGCGAGGAAAAGTAGTCCCTTCTCGGCGATTCTGC

GGAGGGATCTCCGTGGGGCGGTGAACGCCGATGATGCCTCTACTAACCAT

GTTCATGTTTTCTTTTTTTTTCTACAGGTCCTGGGTGACGAACAGGGTAC

CGCCACCATGGCCACCGGCTCTCGCACAAGCCTGCTGCTGGCTTTCGGAC

TGCTGTGCCTGCCTTGGCTCCAGGAGGGCTCCGCCGCTAGCATCGATACC

GTCGCTATGTGCTGGAGGCTTGCTGAAGGCTGTATGCTGAAATCTTCCGG

TGGTTCCACTGCGTTTTGGCCTCTGACTGACGCAGTGGAACCCGGAAGAT

TTCAGGACACAAGGCCTGTTACTAGCACTCACATGGAACAAATGGCCTCT

AGCCTGGAGGCTTGCTGAAGGCTGTATGCTGATATCCTGAATATGGTATG

CAGCGTTTTGGCCTCTGACTGACGCTGCATACCATTCAGGATATCAGGAC

ACAAGGCCTGTTACTAGCACTCACATGGAACAAATGGCCTCTAGCCTGGA

GGCTTGCTGAAGGCTGTATGCTGTTTAAAGCTCAAACGCGTTCGCCGTTT

TGGCCTCTGACTGACGGCGAACGCGTGAGCTTTAAACAGGACACAAGGCC

TGTTACTAGCACTCACATGGAACAAATGGCCTCTCTAGAAT 3'

SEQ ID NO. 23 = SEQ ID NO:. 1 + SEQ ID NO. 11
5' AATCAACCTCTGGATTACAAAATTTGTGAAAGATTGACTGGTATTCTT

AACTATGTTGCTCCTTTTACGCTATGTGGATACGCTGCTTTAATGCCTTT

GTATCATGCTATTGCTTCCCGTATGGCTTTCATTTTCTCCTCCTTGTATA

AATCCTGGTTGCTGTCTCTTTATGAGGAGTTGTGTGCCCGTTGTCAGGCAA

CGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCC

CTATTGCCACGGCGGAACTCATCGCCGCCTGCCTTGCCCGCTGCTGGACA

GGGGCTCGGCTGTTGGGCACTGACAATTCCGTGGTGTTGTCGGGGAAATC

ATCGTCCTTTCCTTGGCTGCTCGCCTGTGTTGCCACCTGGATTCTGCGCG

GGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTAAGCTTA

TCGATACCGTCGAGATCTAACTTGTTTATTGCAGCTTATAATGGTTACAA

ATAAAGCAATAGCATCACAAATTTCACAAATAAAGCATTTTTTTCACTGC

ATTCTAGTTGTGGTTTGTCCAAACTCATCAATGTATCTTATCATGTCTGG

ATCTCGACCTCGACTAGAGCATGGCTACGTAGATAAGTAGCATGGCGGGT

TAATCATTAACTACAAGGAACCCCTAGTGATGGAGTTGGCCACTCCCTCT

CTGCGCGCTCGCTCGCTCACTGAGGCCGGGCGACCAAAGGTCGCCCGACG

CCCGGGCTTTGCCCGGGCGGCCTCAGTGAGCGAGCGAGCGCGCAGCTGGC

GTAATAGCGAAGAGGCCCGCACCGATCGCCCTTCCCAACAGTTGCGCAGC

CTGAATGGCGAATGGCGATTCCGTTGCAATGGCTGGCGGTAATATTGTTC

TGGATATTACCAGCAAGGCCGATAGTTTGAGTTCTTCTACTCAGGCAAGT

GATGTTATTACTAATCAAAGAAGTATTGCGACAACGGTTAATTTGCGTGA

TGGACAGACTCTTTTACTCGGTGGCCTCACTGATTATAAAAACACTTCTC

AGGATTCTGGCGTACCGTTCCTGTCTAAAATCCCTTTAATCGGCCTCCTG

-continued

TTTAGCTCCCGCTCTGATTCTAACGAGGAAAGCACGTTATACGTGCTCGT

CAAAGCAACCATAGTACGCGCCCTGTAGCGGCGCATTAAGCGCGGCGGGT

GTGGTGGTTACGCGCAGCGTGACCGCTACACTTGCCAGCGCCCTAGCGCC

CGCTCCTTTCGCTTTCTTCCCTTCCTTTCTCGCCACGTTCGCCGGCTTTC

CCCGTCAAGCTCTAAATCGGGGGCTCCCTTTAGGGTTCCGATTTAGTGCT

TTACGGCACCTCGACCCCAAAAAACTTGATTAGGGTGATGGTTCACGTAG

TGGGCCATCGCCCTGATAGACGGTTTTTCGCCCTTTGACGTTGGAGTCCA

CGTTCTTTAATAGTGGACTCTTGTTCCAAACTGGAACAACACTCAACCCT

ATCTCCGGTCTATTCTTTTGATTTATAAGGGATTTTGCCGATTTCGGCCTA

TTGGTTAAAAAATGAGCTGATTTAACAAAAATTTAACGCGAATTTTAACA

AAATATTAACGTTTACAATTTAAATATTTGCTTATACAATCTTCCTGTTT

TTGGGGCTTTTCTGATTATCAACCGGGGTACATATGATTGACATGCTAGT

TTTACGATTACCGTTCATCGATTCTCTTGTTTGCTCCAGACTCTCAGGCA

ATGACCTGATAGCCTTTGTAGAGACCTCTCAAAAATAGCTACCCTCTCCG

GCATGAATTTATCAGCTAGAACGGTTGAATATCATATTGATGGTGATTTG

ACTGTCTCCGGCCTTTCTCACCCGTTTGAATCTTTACCTACACATTACTC

AGGCATTGCATTTAAAATATATGAGGGTTCTAAAAATTTTTATCCTTGCG

TTGAAATAAAGGCTTCTCCCGCAAAAGTATTACAGGGTCATAATGTTTTT

GGTACAACCGATTTAGCTTTATGCTCTGAGGCTTTATTGCTTAATTTTGC

TAATTCTTTGCCTTGCCTGTATGATTTATTGGATGTTGGAATTCCTGATG

CGGTATTTTCTCCTTACGCATCTGTGCGGTATTTCACACCGCATATGGTG

CACTCTCAGTACAATCTGCTCTGATGCCGCATAGTTAAGCCAGCCCCGAC

ACCCGCCAACACCCGCTGACGCGCCCTGACGGGCTTGTCTGCTCCCGGCA

TCCGCTTACAGACAAGCTGTGACCGTCTCCGGGAGCTGCATGTGTCAGAG

GTTTTCACCGTCATCACCGAAACGCGCGAGACGAAAGGGCCTCGTGATAC

GCCTATTTTTATAGGTTAATGTCATGATAATAATGGTTTCTTAGACGTCA

GGTGGCACTTTTCGGGGAAATGTGCGCGGAACCCCTATTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

TTTCGCCCCGAAGAACGTTTTCCAATGATGAGCACTTTTAAAGTTCTGCT

ATGTGGCGCGGTATTATCCCGTATTGACGCCGGGCAAGAGCAACTCGGTC

GCCGCATACACTATTCTCAGAATGACTTGGTTGAGTACTCACCAGTCACA

GAAAAGCATCTTACGGATGGCATGACAGTAAGAGAATTATGCAGTGCTGC

CATAACCATGAGTGATAACACTGCGGCCAACTTACTTCTGACAACGATCG

GAGGACCGAAGGAGCTAACCGCTTTTTTGCACAACATGGGGGATCATGTA

ACTCGCCTTGATCGTTGGGAACCGGAGCTGAATGAAGCCATACCAAACGA

CGAGCGTGACACCACGATGCCTGTAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT

AAAAGGATCTAGGTGAAGATCCTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCG

CCTCTCCCCGCGCGTTGGCCGATTCATTAATGCAGCAGCTGCGCGCTCGC

TCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACT

CCATCACTAGGGGTTCCTTGTAGTTAATGATTAACCCGCCATGCTACTTA

TCTACGTAGCCATGCTCTAGGACATTGATTATTGACTAGTGGAGTTCCGC

GTTACATAACTTACGGTAAATGGCCCGCCTGGCTGACCGCCCAACGACCC

CCGCCCATTGACGTCAATAATGACGTATGTTCCCATAGTAACGCCAATAG

GGACTTTCCATTGACGTCAATGGGTGGAGTATTTACGGTAAACTGCCCAC

TTGGCAGTACATCAAGTGTATCATATGCCAAGTACGCCCCCTATTGACGT

CAATGACGGTAAATGGCCCGCCTGGCATTATGCCCAGTACATGACCTTAT

GGGACTTTCCTACTTGGCAGTACATCTACGTATTAGTCATCGCTATTACC

ATGGTCGAGGTGAGCCCCACGTTCTGCTTCACTCTCCCCATCTCCCCCCC

CTCCCCACCCCCAATTTTGTATTTATTTATTTTTTAATTATTTTGTGCAG

CGATGGGGGCGGGGGGGGGGGGGGGCGCGCGCCAGGCGGGGGGGGCGGGG

CGAGGGGGGGGCGGGGCGAGGCGGAGAGGTGCGGCGGCAGCCAATCAGAG

CGGCGCGCTCCGAAAGTTTCCTTTTATGGCGAGGCGGCGGCGGCGGCGGC

CCTATAAAAAGCGAAGCGCGCGGCGGGCGGGAGTCGCTGCGCGCTGCCTT

CGCCCCGTGCCCCGCTCCGCCGCCGCCTCGCGCCGCCCGCCCCGGCTCTG

ACTGACCGCGTTACTAAAACAGGTAAGTCCGGCCTCCGCGCCGGGTTTTG

GCGCCTCCCGCGGGCGCCCCCCTCCTCACGGCGAGCGCTGCCACGTCAGA

CGAAGGGCGCAGCGAGCGTCCTGATCCTTCCGCCCGGACGCTCAGGACAG

CGGCCCGCTGCTCATAAGACTCGGCCTTAGAACCCCAGTATCAGCAGAAG

GACATTTTAGGACGGGACTTGGGTGACTCTAGGGCACTGGTTTTCTTTCC

AGAGAGCGGAACAGGCGAGGAAAAGTAGTCCCTTCTCGGCGATTCTGCGG

AGGGATCTCCGTGGGGCGGTGAACGCCGATGATGCCTCTACTAACCATGT

TCATGTTTTCTTTTTTTTTTCTACAGGTCCTGGGTGACGAACAGGGTACCG

CCACCATGGCCACCGGCTCTCGCACAAGCCTGCTGCTGGCTTTCGGACTG

CTGTGCCTGCCTTGGCTCCAGGAGGGCTCCGCCGCTAGCATCGATACCGT

CGCTATGTGCTGGAGGCTTGCTGAAGGCTGTATGCTGTAATAAAGGTCTG

GGAATCACCCGTTTTGGCCTCTGACTGACGGGTGATTCCGACCTTTATTA

CAGGACACAAGGCCTGTTACTAGCACTCACATGGAACAAATGGCCTCTAG

CCTGGAGGCTTGCTGAAGGCTGTATGCTGTAATACGCCAGATCACCATCA

GCGTTTTGGCCTCTGACTGACGCTGATGGTGCTGGCGTATTACAGGACAC

AAGGCCTGTTACTAGCACTCACATGGAACAAATGGCCTCTAGCCTGGAGG

CTTGCTGAAGGCTGTATGCTGATACAGAAACGAAGGTTCAGGCCGTTTTG

GCCTCTGACTGACGGCCTGAACCCGTTTCTGTATCAGGACACAAGGCCTG

TTACTAGCACTCACATGGAACAAATGGCCTCTCTAGAAT 3'

SEQ ID NO. 24 = SEQ ID NO. 1 + SEQ ID NO. 12
5' AATCAACCTCTGGATTACAAAATTTGTGAAAGATTGACTGGTATTCTT

AACTATGTTGCTCCTTTTACGCTATGTGGATACGCTGCTTTAATGCCTTT

GTATCATGCTATTGCTTCCCGTATGGCTTTCATTTTCTCCTCCTTGTATA

AATCCTGGTTGCTGTCTCTTTATGAGGAGTTGTGGCCCGTTGTCAGGCAA

CGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCC

CTATTGCCACGGCGGAACTCATCGCCGCCTGCCTTGCCCGCTGCTGGACA

GGGGCTCGGCTGTTGGGCACTGACAATTCCGTGGTGTTGTCGGGGAAATC

ATCGTCCTTTCCTTGGCTGCTCGCCTGTGTTGCCACCTGGATTCTGCGCG

GGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTAAGCTTA

TCGATACCGTCGAGATCTAACTTGTTTATTGCAGCTTATAATGGTTACAA

ATAAAGCAATAGCATCACAAATTTCACAAATAAAGCATTTTTTTCACTGC

ATTCTAGTTGTGGTTTGTCCAAACTCATCAATGTATCTTATCATGTCTGG

ATCTCGACCTGACTAGAGCATGGCTACGTAGATAAGTAGCATGGCGGGT

TAATCATTAACTACAAGGAACCCCTAGTGATGGAGTTGGCCACTCCCTCT

CTGCGCGCTCGCTCGCTCACTGAGGCCGGGCGACCAAAGGTCGCCCGACG

CCCGGGCTTTGCCCGGGCGGCCTCAGTGAGCGAGCGAGCGCGCAGCTGGC

-continued

GTAATAGCGAAGAGGCCCGCACCGATCGCCCTTCCCAACAGTTGCGCAGC

CTGAATGGCGAATGGCGATTCCGTTGCAATGGCTGGCGGTAATATTGTTC

TGGATATTACCAGCAAGGCCGATAGTTTGAGTTCTTCTACTCAGGCAAGT

GATGTTATTACTAATCAAAGAAGTATTGCGACAACGGTTAATTTGCGTGA

TGGACAGACTCTTTTACTCGGTGGCCTCACTGATTATAAAAACACTTCTC

AGGATTCTGGCGTACCGTTCCTGTCTAAAATCCCTTTAATCGGCCTCCTG

TTTAGCTCCCGCTCTGATTCTAACGAGGAAAGCACGTTATACGTGCTCGT

CAAAGCAACCATAGTACGCGCCCTGTAGCGGCGCATTAAGCGCGGCGGGT

GTGGTGGTTACGCGCAGCGTGACCGCTACACTTGCCAGCGCCCTAGCGCC

CGCTCCTTTCGCTTTCTTCCCTTCCTTTCTCGCCACGTTCGCCGGCTTTC

CCCGTCAAGCTCTAAATCGGGGGCTCCCTTTAGGGTTCCGATTTAGTGCT

TTACGGCACCTCGACCCCAAAAAACTTGATTAGGGTGATGGTTCACGTAG

TGGGCCATCGCCCTGATAGACGGTTTTTCGCCCTTTGACGTTGGAGTCCA

CGTTCTTTAATAGTGGACTCTTGTTCCAAACTGGAACAACACTCAACCCT

ATCTCGGTCTATTCTTTTGATTTATAAGGGATTTTGCCGATTTCGGCCTA

TTGGTTAAAAAATGAGCTGATTTAACAAAAATTTAACGCGAATTTTAACA

AAATATTAACGTTTACAATTTAAATATTTGCTTATACAATCTTCCTGTTT

TTGGGGCTTTTCTGATTATCAACCGGGGTACATATGATTGACATGCTAGT

TTTACGATTACCGTTCATCGATTCTCTTGTTTGCTCCAGACTCTCAGGCA

ATGACCTGATAGCCTTTGTAGAGACCTCTCAAAAATAGCTACCCTCTCCG

GCATGAATTTATCAGCTAGAACGGTTGAATATCATATTGATGGTGATTTG

ACTGTCTCCGGCCTTTCTCACCCGTTTGAATCTTTACCTACACATTACTC

AGGCATTGCATTTAAAATATATGAGGGTTCTAAAAATTTTTATCCTTGCG

TTGAAATAAAGGCTTCTCCCGCAAAAGTATTACAGGGTCATAATGTTTTT

GGTACAACCGATTTAGCTTTATGCTCTGAGGCTTTATTGCTTAATTTTGC

TAATTCTTTGCCTTGCCTGTATGATTTATTGGATGTTGGAATTCCTGATG

CGGTATTTTCTCCTTACGCATCTGTGCGGTATTTCACACCGCATATGGTG

CACTCTCAGTACAATCTGCTCTGATGCCGCATAGTTAAGCCAGCCCCGAC

ACCCGCCAACACCCGCTGACGCGCCCTGACGGGCTTGTCTGCTCCCGGCA

TCCGCTTACAGACAAGCTGTGACCGTCTCCGGGAGCTGCATGTGTCAGAG

GTTTTCACCGTCATCACCGAAACGCGCGAGACGAAAGGGCCTCGTGATAC

GCCTATTTTTATAGGTTAATGTCATGATAATAATGGTTTCTTAGACGTCA

GGTGGCACTTTCGGGGAAATGTGCGCGGAACCCCTATTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

TTTCGCCCCGAAGAACGTTTTCCAATGATGAGCACTTTTAAAGTTCTGCT

ATGTGGCGCGGTATTATCCCGTATTGACGCCGGGCAAGAGCAACTCGGTC

GCCGCATACACTATTCTCAGAATGACTTGGTTGAGTACTCACCAGTCACA

-continued

GAAAAGCATCTTACGGATGGCATGACAGTAAGAGAATTATGCAGTGCTGC

CATAACCATGAGTGATAACACTGCGGCCAACTTACTTCTGACAACGATCG

GAGGACCGAAGGAGCTAACCGCTTTTTTGCACAACATGGGGGATCATGTA

ACTCGCCTTGATCGTTGGGAACCGGAGCTGAATGAAGCCATACCAAACGA

CGAGCGTGACACCACGATGCCTGTAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT

AAAAGGATCTAGGTGAAGATCCTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCG

CCTCTCCCCGCGCGTTGGCCGATTCATTAATGCAGCAGCTGCGCGCTCGC

TCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACT

CCATCACTAGGGGTTCCTTGTAGTTAATGATTAACCCGCCATGCTACTTA

TCTACGTAGCCATGCTCTAGGACATTGATTATTGACTAGTGGAGTTCCGC

GTTACATAACTTACGGTAAATGGCCCGCCTGGCTGACCGCCCAACGACCC

CCGCCCATTGACGTCAATAATGACGTATGTTCCCATAGTAACGCCAATAG

GGACTTTCCATTGACGTCAATGGGTGGAGTATTTACGGTAAACTGCCCAC

TTGGCAGTACATCAAGTGTATCATATGCCAAGTACGCCCCCTATTGACGT

CAATGACGGTAAATGGCCCGCCTGGCATTATGCCCAGTACATGACCTTAT

-continued

GGGACTTTCCTACTTGGCAGTACATCTACGTATTAGTCATCGCTATTACC

ATGGTCGAGGTGAGCCCCACGTTCTGCTTCACTCTCCCCATCTCCCCCCC

CTCCCCACCCCCAATTTTGTATTTATTTATTTTTTAATTATTTTGTGCAG

CGATGGGGCGGGGGGGGGGGGGGGCGCGCGCCAGGCGGGGGGGGGGGGG

CGAGGGGCGGGGGGGGCGAGGCGGAGAGGTGCGGCGGCAGCCAATCAGAG

CGGCGCGCTCCGAAAGTTTCCTTTTATGGCGAGGCGGCGGCGGCGGCGGC

CCTATAAAAAGCGAAGCGCGCGGCGGGCGGGAGTCGCTGCGCGCTGCCTT

CGCCCCGTGCCCCGCTCCGCCGCCGCCTCGCGCCGCCCGCCCCGGCTCTG

ACTGACCGCGTTACTAAAACAGGTAAGTCCGGCCTCCGCGCCGGGTTTTG

GCGCCTCCCGCGGGCGCCCCCCTCCTCACGGCGAGCGCTGCCACGTCAGA

CGAAGGGCGCAGCGAGCGTCCTGATCCTTCCGCCCGGACGCTCAGGACAG

CGGCCCGCTGCTCATAAGACTCGGCCTTAGAACCCCAGTATCAGCAGAAG

GACATTTTAGGACGGGACTTGGGTGACTCTAGGGCACTGGTTTTCTTTCC

AGAGAGCGGAACAGGCGAGGAAAAGTAGTCCCTTCTCGGCGATTCTGCGG

AGGGATCTCCGTGGGGCGGTGAACGCCGATGATGCCTCTACTAACCATGT

TCATGTTTTCTTTTTTTTTCTACAGGTCCTGGGTGACGAACAGGGTACCG

CCACCATGGCCACCGGCTCTCGCACAAGCCTGCTGCTGGCTTTCGGACTG

CTGTGCCTGCCTTGGCTCCAGGAGGGCTCCGCCGCTAGCATCGATACCGT

CGCTATGTGCTGGAGGCTTGCTGAAGGCTGTATGCTGTCAGATCGCTGTG

GTAAACAGGCGTTTTGGCCTCTGACTGACGCCTGTTTACCAGCGATCTGA

CAGGACACAAGGCCTGTTACTAGCACTCACATGGAACAAATGGCCTCTAG

CCTGGAGGCTTGCTGAAGGCTGTATGCTGAGAATCAGATCAGATAGCGAT

CCGTTTTGGCCTCTGACTGACGGATCGCTATCTGCTGATTCTCAGGACAC

AAGGCCTGTTACTAGCACTCACATGGAACAAATGGCCTCTAGCCTGGAGG

CTTGCTGAAGGCTGTATGCTGAAACATGCCAACAGCAGAATGCCGTTTTG

GCCTCTGACTGACGGCATTCTGCTGGGCATGTTTCAGGACACAAGGCCTG

TTACTAGCACTCACATGGAACAAATGGCCTCTCTAGAAT 3'

SEQ ID NO. 25 = SEQ ID NO. 1 + SEQ ID NO. 13
5' AATCAACCTCTGGATTACAAAATTTGTGAAAGATTGACTGGTATTCTT

AACTATGTTGCTCCTTTTACGCTATGTGGATACGCTGCTTTAATGCCTTT

GTATCATGCTATTGCTTCCCGTATGGCTTTCATTTTCTCCTCCTTGTATA

AATCCTGGTTGCTGTCTCTTTATGAGGAGTTGTGGCCCGTTGTCAGGCAA

CGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCC

CTATTGCCACGGCGGAACTCATCGCCGCCTGCCTTGCCCGCTGCTGGACA

GGGGCTCGGCTGTTGGGCACTGACAATTCCGTGGTGTTGTCGGGGAAATC

ATCGTCCTTTCCTTGGCTGCTCGCCTGTGTTGCCACCTGGATTCTGCGCG

GGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTAAGCTTA

TCGATACCGTCGAGATCTAACTTGTTTATTGCAGCTTATAATGGTTACAA

-continued

ATAAAGCAATAGCATCACAAATTTCACAAATAAAGCATTTTTTTCACTGC

ATTCTAGTTGTGGTTTGTCCAAACTCATCAATGTATCTTATCATGTCTGG

ATCTCGACCTCGACTAGAGCATGGCTACGTAGATAAGTAGCATGGCGGGT

TAATCATTAACTACAAGGAACCCCTAGTGATGGAGTTGGCCACTCCCTCT

CTGCGCGCTCGCTCGCTCACTGAGGCCGGGCGACCAAAGGTCGCCCGACG

CCCGGGCTTTGCCCGGGCGGCCTCAGTGAGCGAGCGAGCGCGCAGCTGGC

GTAATAGCGAAGAGGCCCGCACCGATCGCCCTTCCCAACAGTTGCGCAGC

CTGAATGGCGAATGGCGATTCCGTTGCAATGGCTGGCGGTAATATTGTTC

TGGATATTACCAGCAAGGCCGATAGTTTGAGTTCTTCTACTCAGGCAAGT

GATGTTATTACTAATCAAAGAAGTATTGCGACAACGGTTAATTTGCGTGA

TGGACAGACTCTTTTACTCGGTGGCCTCACTGATTATAAAAACACTTCTC

AGGATTCTGGCGTACCGTTCCTGTCTAAAATCCCTTTAATCGGCCTCCTG

TTTAGCTCCCGCTCTGATTCTAACGAGGAAAGCACGTTATACGTGCTCGT

CAAAGCAACCATAGTACGCGCCCTGTAGCGGCGCATTAAGCGCGGCGGGT

GTGGTGGTTACGCGCAGCGTGACCGCTACACTTGCCAGCGCCCTAGCGCC

CGCTCCTTTCGCTTTCTTCCCTTCCTTTCTCGCCACGTTCGCCGGCTTTC

CCCGTCAAGCTCTAAATCGGGGGCTCCCTTTAGGGTTCCGATTTAGTGCT

TTACGGCACCTCGACCCCAAAAAACTTGATTAGGGTGATGGTTCACGTAG

TGGGCCATCGCCCTGATAGACGGTTTTTCGCCCTTTGACGTTGGAGTCCA

CGTTCTTTAATAGTGGACTCTTGTTCCAAACTGGAACAACACTCAACCCT

ATCTCGGTCTATTCTTTTGATTTATAAGGGATTTTGCCGATTTCGGCCTA

TTGGTTAAAAAATGAGCTGATTTAACAAAAATTTAACGCGAATTTTAACA

AAATATTAACGTTTACAATTTAAATATTTGCTTATACAATCTTCCTGTTT

TTGGGGCTTTTCTGATTATCAACCGGGGTACATATGATTGACATGCTAGT

TTTACGATTACCGTTCATCGATTCTCTTGTTTGCTCCAGACTCTCAGGCA

ATGACCTGATAGCCTTTGTAGAGACCTCTCAAAAATAGCTACCCTCTCCG

GCATGAATTTATCAGCTAGAACGGTTGAATATCATATTGATGGTGATTTG

ACTGTCTCCGGCCTTTCTCACCCGTTTGAATCTTTACCTACACATTACTC

AGGCATTGCATTTAAAATATATGAGGGTTCTAAAAATTTTTATCCTTGCG

TTGAAATAAAGGCTTCTCCCGCAAAAGTATTACAGGGTCATAATGTTTTT

GGTACAACCGATTTAGCTTTATGCTCTGAGGCTTTATTGCTTAATTTTGC

TAATTCTTTGCCTTGCCTGTATGATTTATTGGATGTTGGAATTCCTGATG

CGGTATTTTCTCCTTACGCATCTGTGCGGTATTTCACACCGCATATGGTG

CACTCTCAGTACAATCTGCTCTGATGCCGCATAGTTAAGCCAGCCCCGAC

ACCCGCCAACACCCGCTGACGCGCCCTGACGGGCTTGTCTGCTCCCGGCA

TCCGCTTACAGACAAGCTGTGACCGTCTCCGGGAGCTGCATGTGTCAGAG

GTTTTCACCGTCATCACCGAAACGCGCGAGACGAAAGGGCCTCGTGATAC

GCCTATTTTTATAGGTTAATGTCATGATAATAATGGTTTCTTAGACGTCA

GGTGGCACTTTTCGGGGAAATGTGCGCGGAACCCCTATTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

-continued

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

TTTCGCCCCGAAGAACGTTTTCCAATGATGAGCACTTTTAAAGTTCTGCT

ATGTGGCGCGGTATTATCCCGTATTGACGCCGGGCAAGAGCAACTCGGTC

GCCGCATACACTATTCTCAGAATGACTTGGTTGAGTACTCACCAGTCACA

GAAAAGCATCTTACGGATGGCATGACAGTAAGAGAATTATGCAGTGCTGC

CATAACCATGAGTGATAACACTGCGGCCAACTTACTTCTGACAACGATCG

GAGGACCGAAGGAGCTAACCGCTTTTTTGCACAACATGGGGGATCATGTA

ACTCGCCTTGATCGTTGGGAACCGGAGCTGAATGAAGCCATACCAAACGA

CGAGCGTGACACCACGATGCCTGTAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT

AAAAGGATCTAGGTGAAGATCCTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCG

CCTCTCCCCGCGCGTTGGCCGATTCATTAATGCAGCAGCTGCGCGCTCGC

TCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACT

CCATCACTAGGGGTTCCTTGTAGTTAATGATTAACCCGCCATGCTACTTA

-continued

TCTACGTAGCCATGCTCTAGGACATTGATTATTGACTAGTGGAGTTCCGC

GTTACATAACTTACGGTAAATGGCCCGCCTGGCTGACCGCCCAACGACCC

CCGCCCATTGACGTCAATAATGACGTATGTTCCCATAGTAACGCCAATAG

GGACTTTCCATTGACGTCAATGGGTGGAGTATTTACGGTAAACTGCCCAC

TTGGCAGTACATCAAGTGTATCATATGCCAAGTACGCCCCCTATTGACGT

CAATGACGGTAAATGGCCCGCCTGGCATTATGCCCAGTACATGACCTTAT

GGGACTTTCCTACTTGGCAGTACATCTACGTATTAGTCATCGCTATTACC

ATGGTCGAGGTGAGCCCCACGTTCTGCTTCACTCTCCCCATCTCCCCCCC

CTCCCCACCCCCAATTTTGTATTTATTTATTTTTTAATTATTTTGTGCAG

CGATGGGGGCGGGGGGGGGGGGGGGCGCGCGCCAGGCGGGGGGGGGGGGG

CGAGGGGCGGGGGGGGCGAGGCGGAGAGGTGCGGCGGCAGCCAATCAGAG

CGGCGCGCTCCGAAAGTTTCCTTTTATGGCGAGGCGGCGGCGGCGGCGGC

CCTATAAAAAGCGAAGCGCGCGGCGGGGGGAGTCGCTGCGCGCTGCCTTC

GCCCCGTGCCCCGCTCCGCCGCCGCCTCGCGCCGCCCGCCCCGGCTCTGA

CTGACCGCGTTACTAAAACAGGTAAGTCCGGCCTCCGCGCCGGGTTTTGG

CGCCTCCCGCGGGCGCCCCCCTCCTCACGGCGAGCGCTGCCACGTCAGAC

GAAGGGCGCAGCGAGCGTCCTGATCCTTCCGCCCGGACGCTCAGGACAGC

GGCCCGCTGCTCATAAGACTCGGCCTTAGAACCCCAGTATCAGCAGAAGG

ACATTTTAGGACGGGACTTGGGTGACTCTAGGGCACTGGTTTTCTTTCCA

GAGAGCGGAACAGGCGAGGAAAAGTAGTCCCTTCTCGGCGATTCTGCGGA

GGGATCTCCGTGGGGCGGTGAACGCCGATGATGCCTCTACTAACCATGTT

CATGTTTTCTTTTTTTTTCTACAGGTCCTGGGTGACGAACAGGGTACCGC

CACCATGGCCACCGGCTCTCGCACAAGCCTGCTGCTGGCTTTCGGACTGC

TGTGCCTGCCTTGGCTCCAGGAGGGCTCCGCCGCTAGCATCGATACCGTC

GCTATGTGCTGGAGGCTTGCTGAAGGCTGTATGCTGACAATCAGATATGG

TTGCTCGGCGTTTTGGCCTCTGACTGACGCCGAGCAACTATCTGATTGTC

AGGACACAAGGCCTGTTACTAGCACTCACATGGAACAAATGGCCTCTAGC

CTGGAGGCTTGCTGAAGGCTGTATGCTGTTTCACAATGCATCGTTCAGCG

CGTTTTGGCCTCTGACTGACGCGCTGAACGGCATTGTGAAACAGGACACA

AGGCCTGTTACTAGCACTCACATGGAACAAATGGCCTCTAGCCTGGAGGC

TTGCTGAAGGCTGTATGCTGACAATAATGCCAACAGGGTGGTCGTTTTGG

CCTCTGACTGACGACCACCCTGGGCATTATTGTCAGGACACAAGGCCTGT

TACTAGCACTCACATGGAACAAATGGCCTCTCTAGAAT 3'

As will be appreciated by those skilled in the art, because the recombinant plasmid is a circular vector, the one or more sequences of the miRNA expression cassettes may be connected at the 3' end of SEQ ID NO. 1, as shown in SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24 and SEQ ID NO. 25, or at the 5' end of SEQ ID NO. 1.

As will be appreciated by those skilled in the art, a perfect match of nucleotides with each of the miRNA expression cassette sequences is not necessary in order to have the desired result of decreased bioavailability of the target biomolecule as a result of the target cell producing the miRNA sequence that will bind to and degrade the mRNA of the target biomolecule. In some embodiments of the present disclosure, about 80% to about 100% nucleotide sequence matching with each of the miRNA expression cassettes causes the desired result. In some embodiments of the present disclosure, about 85% to about 100% nucleotide sequence matching with each of the miRNA expression cassettes causes the desired result. In some embodiments of the present disclosure, about 90% to about 100% nucleotide sequence matching with each of the miRNA expression cassettes causes the desired result. In some embodiments of the present disclosure, about 95% to about 100% nucleotide sequence matching with each of the miRNA expression cassettes causes the desired result.

Example 1—Expression Cassette

Expression cassettes for expressing miRNA were synthesized. The synthesized miRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each miRNA expression cassette was amplified by polymerase chain reaction (PCR) using Taq polymerase and the PCR products were gel purified and the bands on interest were also excised and purified using a gel extraction kit. These PCR products contained the miRNA expression cassettes in addition to 15 base pair 5' and 3' overhangs that aligned with the ends of the linearized pAVA-00200 backbone. Using in-fusion cloning, the amplified miRNA expression cassettes were integrated with the pAVA-00200 backbone via homologous recombination. The resulting RP contained the following: 5' ITR, CASI promoter, miRNA expression cassette, WPRE, SV40 polyA and ITR 3'.

The invention claimed is:

1. A composition that comprises a recombinant plasmid (RP) that comprises a sequence of nucleotides that is SEQ ID NO. 15.

2. The composition of claim 1, wherein the RP is encapsulated in a protein coat, a lipid vesicle, or any combination thereof.

* * * * *

```
                             SEQUENCE LISTING

Sequence total quantity: 25
SEQ ID NO: 1             moltype = DNA   length = 5799
FEATURE                  Location/Qualifiers
source                   1..5799
                         mol_type = other DNA
                         organism = synthetic construct
SEQUENCE: 1
aatcaacctc tggattacaa aatttgtgaa agattgactg gtattcttaa ctatgttgct   60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccact    240
ggttggggca ttgccaccac ctgtcagctc ctttccggga ctttcgcttt ccccctccct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcattttt ttcactgcat tctagttgtg gtttgtccaa   720
actcatcaat gtatcttatc atgtctggat ctcgacctcg actagagcat ggctacgtag   780
ataagtagca tggcgggtta atcattaact acaaggaacc cctagtgatg gagttggcca   840
ctccctctct gcgcgctcgc tcgctcactg aggccgggcg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggc taccgttcct gtctaaaatc cctttaatcg gcctctgtt tagctcccgc    1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg ctccctttta gggttccgat ttagtgcttt   1500
acggcacctc gaccccaaaa aacttgatta gggtgatggt tcacgtagtg ggccatcgcc   1560
ctgatagacg gtttttcgcc ctttgacgtt ggagtccacg ttctttaata gtggactctt   1620
gttccaaact ggaacaacac tcaaccctat ctcggtctat tctttgatt tataagggat    1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaattat cagctagaac ggttgaatat    1980
catattgatg gtgatttgac tgtctccggc ctttctcacc cgtttgaatc tttacctaca   2040
cattactcag gcattgcatt taaaatatat gagggttcta aaaatttttta tccttgcgtt   2100
gaaataaagg cttctcccgc aaaagtatta cagggtcata atgtttttgg tacaaccgat   2160
ttagctttat gctctgaggc tttattgctt aattttgcta attctttgcc ttgcctgtat   2220
gatttattgg atgttggaat cctgatgcg gtattttctc cttacgcatc tgtgcggtat    2280
ttcacaccgc atatggtgca ctctcagtac aatctgctct gatgccgcat agttaagcca   2340
gccccgacac cgccaacac cgctgacgg ccctgacgg gcttgtctgc tcccggcatc     2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcactttt cggggaaatg tgcgcggaac   2580
ccctatttgt ttatttttct aaatacattc aaatatgtat ccgctcatga acaataaccc   2640
ctgataaatg cttcaataat attgaaaaag gaagagtatg agtattcaac atttccgtgt   2700
```

-continued

```
cgcccttatt ccctttttttg cggcattttg ccttcctgtt tttgctcacc cagaaacgct  2760
ggtgaaagta aaagatgctg aagatcagtt gggtgcacga gtgggttaca tcgaactgga  2820
tctcaacagc ggtaagatcc ttgagagttt tcgccccgaa gaacgttttc caatgatgag  2880
cacttttaaa gttctgctat gtggcgcggt attatcccgt attgacgccg ggcaagagca  2940
actcggtcgc cgcatacact attctcagaa tgacttggtt gagtactcac cagtcacaga  3000
aaagcatctt acggatggca tgacagtaag agaattatgc agtgctgcca taaccatgag  3060
tgataacact gcggccaact tacttctgac aacgatcgga ggaccgaagg agctaaccgc  3120
ttttttgcac aacatggggg atcatgtaac tcgccttgat cgttgggaac cggagctgaa  3180
tgaagccata ccaaacgacg agcgtgacac cacgatgcct gtagcaatgg caacaacgtt  3240
gcgcaaacta ttaactggcg aactacttac tctagcttcc cggcaacaat taatagactg  3300
gatggaggcg gataaagttg caggaccact tctgcgctcg gcccttccgg ctggctggtt  3360
tattgctgat aaatctggag ccggtgagcg tgggtctcgc ggtatcattg cagcactggg  3420
gccagatggt aagccctccc gtatcgtagt tatctacacg acggggagtc aggcaactat  3480
ggatgaacga aatagacaga tcgctgagat aggtgcctca ctgattaagc attggtaact  3540
gtcagaccaa gtttactcat atatacttta gattgattta aaacttcatt tttaatttaa  3600
aaggatctag gtgaagatcc tttttgataa tctcatgacc aaaatccctt aacgtgagtt  3660
ttcgttccac tgagcgtcag accccgtaga aaagatcaaa ggatcttctt gagatccttt  3720
ttttctgcgc gtaatctgct gcttgcaaac aaaaaaacca ccgctaccag cggtggtttg  3780
tttgccggat caagagctac caactctttt tccgaaggta actggcttca gcagagcgca  3840
gataccaaat actgtccttc tagtgtagcc gtagttaggc caccacttca agaactctgt  3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg gggggttcgt gcacacagcc cagcttggag cgaacgacct acaccgaact  4080
gagataccta cagcgtgagc tatgagaaag cgccacgctt cccgaaggga gaaaggcgga  4140
caggtatccg gtaagcggca gggtcggaac aggagagcgc acgagggagc ttccaggggg  4200
aaacgcctgg tatctttata gtcctgtcgg gtttcgccac ctctgacttg agcgtcgatt  4260
tttgtgatgc tcgtcagggg ggcggagcct atggaaaaac gccagcaacg cggccttttt  4320
acggttcctg gccttttgct ggccttttgc tcacatgttc tttcctgcgt tatcccctga  4380
ttctgtggat aaccgtatta ccgcctttga gtgagctgat accgctcgcc gcagccgaac  4440
gaccgagcgc agcgagtcag tgagcgagga agcggaagag cgcccaatac gcaaaccgcc  4500
tctccccgcg cgttggccga ttcattaatg cagcagctgg cgcgctcgctc gctcactgag  4560
gccgcccggg caaagcccgg gcgtcgggcg acctttggtc gcccggcctc agtgagcgag  4620
cgagcgcgca gagagggagt ggccaactcc atcactaggg gttccttgta gttaatgatt  4680
aacccgccat gctacttatc tacgtagcca tgctctagga cattgattat tgactagtgg  4740
agttccgcgt tacataactt acggtaaatg ccccgcctgg ctgaccgccc aacgacccc  4800
gcccattgac gtcaataatg acgtatgttc ccatagtaac gccaataggg actttccatt  4860
gacgtcaatg ggtggagtat ttacggtaaa ctgcccactt ggcagtacat caagtgtatc  4920
atatgccaag tacgcccccct attgacgtca atgacggtaa atggcccgcc tggcattatg  4980
cccagtacat gaccttatgg gactttccta cttggcagta catctacgta ttagtcatcg  5040
ctattaccat ggtcgaggtg agccccacgt tctgcttcac tctccccatc tcccccccct  5100
ccccacccccc aattttgtat ttatttattt tttaattatt ttgtgcagcg atggggggcgg  5160
ggggggggg gggcgcgcgc caggcggggc ggggcggggc gaggggcggg gcggggcgag  5220
gcggagaggt gcggcgggcag ccaatcagag cggcgcgctc cgaaagtttc cttttatggc  5280
gaggcggcgg cggcggcggc cctataaaaa gcgaagcgcg cggcgggcgg gagtcgctgc  5340
gcgctgcctt cgccccgtgc cccgctccgc cgccgcctcg cgccgcccgc cccggctctg  5400
actgaccgcg ttactaaaac aggtaagtcc ggcctccgcg ccgggttttg gcgcctcccg  5460
cgggcgcccc cctcctcacg gcgagcgctg ccacgtcaga caaagggcgc agcgagcgtc  5520
ctgatccttc cgcccggacg ctcaggacag cggcccgctg ctcataagac tcggccttag  5580
aacccagta tcagcagaag gacattttag gacgggactt gggtgactct agggcactgg  5640
ttttctttcc agagagcgga acaggcgagg aaaagtagtc ccttctcggc gattctgcgg  5700
agggatctcc gtggggcggt gaacgccgat gatgcctcta ctaaccatgt tcatgttttc  5760
tttttttttc tacaggtcct gggtgacgaa cagggtacc            5799
```

SEQ ID NO: 2          moltype = DNA  length = 540
FEATURE                 Location/Qualifiers
source                  1..540
                        mol_type = other DNA
                        organism = synthetic construct
SEQUENCE: 2

```
gccaccatgg ccaccggctc tcgcacaagc ctgctgctgg ctttcggact gctgtgcctg  60
ccttggctcc aggagggctc cgccgctagc atcgataccg tcgctatgtg ctggaggctt  120
gctgaaggct gtatgctgat caatcggatt gcggtaatcg cgttttggcc tctgactgac  180
gcgattaccg atccgattga tcaggacaca aggcctgtta ctagcactca catggaacaa  240
atggcctcta gcctggaggc ttgctgaagg ctgtatgctg atctttgcta aattggtgca  300
cgcgtttttgg cctctgactg acgcgtgcac cattagcaaa gatcaggaca caaggcctgt  360
tactagcact cacatggaac aaatggcctc tagcctggag gcttgctgaa ggctgtatgc  420
tgacttcaat cacaattcca gcgccgtttt ggcctctgac tgacgcgct ggaagtgatt  480
gaagtcagga cacaaggcct gttactagca ctcacatgga acaaatggcc tctctagaat  540
```

SEQ ID NO: 3          moltype = DNA  length = 540
FEATURE                 Location/Qualifiers
source                  1..540
                        mol_type = other DNA
                        organism = synthetic construct
SEQUENCE: 3

```
gccaccatgg ccaccggctc tcgcacaagc ctgctgctgg ctttcggact gctgtgcctg  60
ccttggctcc aggagggctc cgccgctagc atcgataccg tcgctatgtg ctggaggctt  120
gctgaaggct gtatgctgta atctttcgct ggctgcagtc gtttttggcc tctgactgac  180
gaactgcagc gcgaaagatt acaggacaca aggcctgtta ctagcactca catggaacaa  240
```

-continued

```
atggcctcta gcctggaggc ttgctgaagg ctgtatgctg tgttaatgct gatgtcacgc  300
tgcgttttgg cctctgactg acgcagcgtg accagcatta acacaggaca caaggcctgt  360
tactagcact cacatggaac aaatggcctc tagcctggag gcttgctgaa ggctgtatgc  420
tgttcacctg gttaacacat acaccgtttt ggcctctgac tgacggtgta tgtgaaccag  480
gtgaacagga cacaaggcct gttactagca ctcacatgga acaaatggcc tctctagaat  540

SEQ ID NO: 4               moltype = DNA   length = 540
FEATURE                    Location/Qualifiers
source                     1..540
                           mol_type = other DNA
                           organism = synthetic construct
SEQUENCE: 4
gccaccatgg ccaccggctc tcgcacaagc ctgctgctgg ctttcggact gctgtgcctg  60
ccttggctcc aggagggctc cgccgctagc atcgataccg tcgctatgtg ctggaggctt  120
gctgaaggct gtatgctgat ttcttcctgt gcgctttcgc cgtttttggcc tctgactgac  180
ggcgaaagcg caggaagaaa tcaggacaca aggcctgtta ctagcactca catgaacaa  240
atggcctcta gcctggaggc ttgctgaagg ctgtatgctg agaataatca gatcagcacg  300
ctcgtttttgg cctctgactg acgagcgtgc tgctgattat tctcaggaca caaggcctgt  360
tactagcact cacatggaac aaatggcctc tagcctggag gcttgctgaa ggctgtatgc  420
tgtaatcagg ctgaattcag atagcgtttt ggcctctgac tgacgctatc tgaacagcct  480
gattacagga cacaaggcct gttactagca ctcacatgga acaaatggcc tctctagaat  540

SEQ ID NO: 5               moltype = DNA   length = 540
FEATURE                    Location/Qualifiers
source                     1..540
                           mol_type = other DNA
                           organism = synthetic construct
SEQUENCE: 5
gccaccatgg ccaccggctc tcgcacaagc ctgctgctgg ctttcggact gctgtgcctg  60
ccttggctcc aggagggctc cgccgctagc atcgataccg tcgctatgtg ctggaggctt  120
gctgaaggct gtatgctgat aatcaccgct gcaggttcag cgtttttggcc tctgactgac  180
gctgaacctg gcggtgatta tcaggacaca aggcctgtta ctagcactca catgaacaa  240
atggcctcta gcctggaggc ttgctgaagg ctgtatgctg ttcaatcgcg tattggtaat  300
cgcgtttttgg cctctgacttg acgcgattac caacgcgatt gaacaggaca caaggcctgt  360
tactagcact cacatggaac aaatggcctc tagcctggag gcttgctgaa ggctgtatgc  420
tgtgatcatg ctgaaaatgg tgcacgtttt ggcctctgac tgacgtgcac cattcagcat  480
gatcacagga cacaaggcct gttactagca ctcacatgga acaaatggcc tctctagaat  540

SEQ ID NO: 6               moltype = DNA   length = 540
FEATURE                    Location/Qualifiers
source                     1..540
                           mol_type = other DNA
                           organism = synthetic construct
SEQUENCE: 6
gccaccatgg ccaccggctc tcgcacaagc ctgctgctgg ctttcggact gctgtgcctg  60
ccttggctcc aggagggctc cgccgctagc atcgataccg tcgctatgtg ctggaggctt  120
gctgaaggct gtatgctgag gtaatatcct gacgctcagc cgtttttggcc tctgactgac  180
ggctgagcgt ggatattacc tcaggacaca aggcctgtta ctagcactca catgaacaa  240
atggcctcta gcctggaggc ttgctgaagg ctgtatgctg tacagaatca gataatcagc  300
gccgtttttgg cctctgactg acggcgctga ttctgattct gtacaggaca caaggcctgt  360
tactagcact cacatggaac aaatggcctc tagcctggag gcttgctgaa ggctgtatgc  420
tgtcatgttt aaaaattcgc tgcgcgtttt ggcctctgac tgacgcgcag cgaatttaaa  480
catgacagga cacaaggcct gttactagca ctcacatgga acaaatggcc tctctagaat  540

SEQ ID NO: 7               moltype = DNA   length = 540
FEATURE                    Location/Qualifiers
source                     1..540
                           mol_type = other DNA
                           organism = synthetic construct
SEQUENCE: 7
gccaccatgg ccaccggctc tcgcacaagc ctgctgctgg ctttcggact gctgtgcctg  60
ccttggctcc aggagggctc cgccgctagc atcgataccg tcgctatgtg ctggaggctt  120
gctgaaggct gtatgctgat gaatcgggtt gtctgaatcg cgtttttggcc tctgactgac  180
gcgattcaga acccgattca tcaggacaca aggcctgtta ctagcactca catgaacaa  240
atggcctcta gcctggaggc ttgctgaagg ctgtatgctg aacactttgc tatatcatcc  300
tgcgttttgg cctctgactg acgcaggatg atagcaaagt gttcaggaca caaggcctgt  360
tactagcact cacatggaac aaatggcctc tagcctggag gcttgctgaa ggctgtatgc  420
tgttctgttc gttaagctaa tgctcgtttt ggcctctgac tgacgagcat tagcaacgaa  480
cagaacagga cacaaggcct gttactagca ctcacatgga acaaatggcc tctctagaat  540

SEQ ID NO: 8               moltype = DNA   length = 540
FEATURE                    Location/Qualifiers
source                     1..540
                           mol_type = other DNA
                           organism = synthetic construct
SEQUENCE: 8
gccaccatgg ccaccggctc tcgcacaagc ctgctgctgg ctttcggact gctgtgcctg  60
ccttggctcc aggagggctc cgccgctagc atcgataccg tcgctatgtg ctggaggctt  120
gctgaaggct gtatgctgga gcattagcaa tgcgaacaga agtttttggcc tctgactgac  180
```

-continued

```
ttctgttcgt tgctaatgct ccaggacaca aggcctgtta ctagcactca catggaacaa  240
atggcctcta gcctggaggc ttgctgaagg ctgtatgctg aaacataatg gattcagcag  300
cgcgttttgg cctctgactg acgcgctgct gaccattatg tttcaggaca caaggcctgt  360
tactagcact cacatggaac aaatggcctc tagcctggag gcttgctgaa ggctgtatgc  420
tgttatcttt gcgaagctgc catccgtttt ggcctctgac tgacggatgg cagccgcaaa  480
gataacagga cacaaggcct gttactagca ctcacatgga acaaatggcc tctctagaat  540
```

```
SEQ ID NO: 9          moltype = DNA  length = 538
FEATURE               Location/Qualifiers
source                1..538
                      mol_type = other DNA
                      organism = synthetic construct
SEQUENCE: 9
gccaccatgg ccaccggctc tcgcacaagc ctgctgctgg cttttcggact gctgtgcctg  60
ccttggctcc aggagggctc cgccgctagc atcgataccg tcgctatgtg ctggaggctt  120
gctgaaggct gtatgctggc tcctccactt ggtggtttgg ttttggcctc tgactgacgc  180
ggcaacattc tggtgattac aggacacaag gcctgttact agcactcaca tggaacaaat  240
ggcctctagc ctggaggctt gctgaaggct gtatgctgta ataatcgcta tttggtgcgg  300
cgttttggcc tctgactgac gccgcaccaa agcgattatg acaggacaca aggcctgtta  360
ctagcactca catggaacaa atggcctcta gcctggaggc ttgctgaagg ctgtatgctg  420
ttctgatcct gaagttcggg ttcgtttttgg cctctgactg acgaacccga accaggatca  480
gaacaggaca caaggcctgt tactagcact cacatggaac aaatggcctc tctagaat    538
```

```
SEQ ID NO: 10         moltype = DNA  length = 540
FEATURE               Location/Qualifiers
source                1..540
                      mol_type = other DNA
                      organism = synthetic construct
SEQUENCE: 10
gccaccatgg ccaccggctc tcgcacaagc ctgctgctgg cttttcggact gctgtgcctg  60
ccttggctcc aggagggctc cgccgctagc atcgataccg tcgctatgtg ctggaggctt  120
gctgaaggct gtatgctgaa atcttccggt ggttccactg cgtttttggcc tctgactgac  180
gcagtggaac ccgaagatt tcaggacaca aggcctgtta ctagcactca catggaacaa  240
atggcctcta gcctggaggc ttgctgaagg ctgtatgctg atatcctgaa tatggtatgc  300
agcgttttgg cctctgactg acgctgcata ccattcagaa tatcaggaca caaggcctgt  360
tactagcact cacatggaac aaatggcctc tagcctggag gcttgctgaa ggctgtatgc  420
tgtttaaagc tcaaacgcgt tcgccgtttt ggcctctgac tgacggcgaa cgcgtgagct  480
ttaaacagga cacaaggcct gttactagca ctcacatgga acaaatggcc tctctagaat  540
```

```
SEQ ID NO: 11         moltype = DNA  length = 540
FEATURE               Location/Qualifiers
source                1..540
                      mol_type = other DNA
                      organism = synthetic construct
SEQUENCE: 11
gccaccatgg ccaccggctc tcgcacaagc ctgctgctgg ctttcggact gctgtgcctg  60
ccttggctcc aggagggctc cgccgctagc atcgataccg tcgctatgtg ctggaggctt  120
gctgaaggct gtatgctgta ataaaggtct gggaatcacc cgtttttggcc tctgactgac  180
gggtgattcc gacctttatt acaggacaca aggcctgtta ctagcactca catggaacaa  240
atggcctcta gcctggaggc ttgctgaagg ctgtatgctg taatacgcca gatcaccatc  300
agcgttttgg cctctgactg acgctgatgg tgctggcgta ttacaggaca caaggcctgt  360
tactagcact cacatggaac aaatggcctc tagcctggag gcttgctgaa ggctgtatgc  420
tgatacagaa acgaaggttc aggccgtttt ggcctctgac tgacggcctg aacccgtttc  480
tgtatcagga cacaaggcct gttactagca ctcacatgga acaaatggcc tctctagaat  540
```

```
SEQ ID NO: 12         moltype = DNA  length = 540
FEATURE               Location/Qualifiers
source                1..540
                      mol_type = other DNA
                      organism = synthetic construct
SEQUENCE: 12
gccaccatgg ccaccggctc tcgcacaagc ctgctgctgg ctttcggact gctgtgcctg  60
ccttggctcc aggagggctc cgccgctagc atcgataccg tcgctatgtg ctggaggctt  120
gctgaaggct gtatgctgtc agatcgctgt ggtaaacagg cgtttttggcc tctgactgac  180
gcctgtttac cagcgatctg acaggacaca aggcctgtta ctagcactca catggaacaa  240
atggcctcta gcctggaggc ttgctgaagg ctgtatgctg agaatcagat cagatagcga  300
tccgtttttgg cctctgactg acggatcgct atctgctgat tctcaggaca caaggcctgt  360
tactagcact cacatggaac aaatggcctc tagcctggag gcttgctgaa ggctgtatgc  420
tgaaacatgc caacagcaga atgccgtttt ggcctctgac tgacggcatt ctgctgggca  480
tgtttcagga cacaaggcct gttactagca ctcacatgga acaaatggcc tctctagaat  540
```

```
SEQ ID NO: 13         moltype = DNA  length = 540
FEATURE               Location/Qualifiers
source                1..540
                      mol_type = other DNA
                      organism = synthetic construct
SEQUENCE: 13
gccaccatgg ccaccggctc tcgcacaagc ctgctgctgg ctttcggact gctgtgcctg  60
ccttggctcc aggagggctc cgccgctagc atcgataccg tcgctatgtg ctggaggctt  120
```

```
gctgaaggct gtatgctgac aatcagatat ggttgctcgg cgttttggcc tctgactgac    180
gccgagcaac tatctgattg tcaggacaca aggcctgtta ctagcactca catggaacaa    240
atggcctcta gcctggaggc ttgctgaagg ctgtatgctg tttcacaatg catcgttcag    300
cgcgttttgg cctctgactg acgcgctgaa cggcattgtg aaacaggaca caaggcctgt    360
tactgcact cacatggaac aaatggcctc tagcctggag gcttgctgaa ggctgtatgc    420
tgacaataat gccaacaggg tggtcgtttt ggcctctgac tgacgaccac cctgggcatt    480
attgtcagga cacaaggcct gttactagca ctcacatgga acaaatggcc tctctagaat    540

SEQ ID NO: 14          moltype = DNA  length = 6339
FEATURE                Location/Qualifiers
source                 1..6339
                       mol_type = other DNA
                       organism = synthetic construct
SEQUENCE: 14
aatcaacctc tggattacaa aatttgtgaa agattgactg gtattcttaa ctatgttgct     60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aacccccact    240
ggttgggggca ttgccaccac ctgtcagctc ctttccggga ctttcgcttt cccctcct    300
attgccacgg cggaactcat cgccgcctgc cttcccgct gctggacagg ggctcggctg    360
ttgggcactg acaattccgt ggtgttgtcg gggaaatcat cgtcctttcc ttggctgctc    420
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc taagcttatc    600
gataccgtcg agatctaact tgtttattgc agcttataat ggttacaaat aaagcaatag    660
catcacaaat ttcacaaata aagcatttt tccactgcat tctagttgtg gtttgtccaa    720
actcatcaat gtatcttatc atgtctggat ctcgacctcg actagagcat ggctacgtag    780
ataagtagca tggcgggtta tcattaact acaaggaacc cctagtgatg gagttggcca    840
ctccctctct gcgcgctcgc tcgctcactg aggccgggcg accaaaggtc gcccgacgcc    900
cgggctttgc ccgggcggcc tcagtgagcg agcgagcgcg cagctggcgt aatagcgaag    960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggcg taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg gctccctta gggttccgat ttagtgcttt   1500
acggcacctc gaccccaaaa aacttgatta gggtgatggt tcacgtagtg gccatcgcc   1560
ctgatagacg gttttcgcc ctttgacgtt ggagtccacg ttctttaata gtggactctt   1620
gttccaaact ggaacaacac tcaacccat ctcggtctat tctttgatt tataagggat   1680
tttgccgatt tcggcctatt ggttaaaaaa tgagctgatt taacaaaaat ttaacgcgaa   1740
ttttaacaaa atattaacgt ttacaatta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt aaaaatatat gagggttcta aaaattttta tccttgcgtt   2100
gaaataaagg cttctcccgc aaaagtatta cagggtcata atgtttttgg tacaaccgat   2160
ttagctttat gctctgaggc tttattgctt aattttgcc ttgcctgtat attctttggc   2220
gatttattgg atgttggaat tcctgatgcg gtatttttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcactttt cggggaaatg tgcgcggaac   2580
ccctatttgt ttatttttct aaatacattc aaatatgtat ccgctcatga cacaataacc   2640
ctgataaatg cttcaataat attgaaaaag gaagagtatg agtattcaac atttccgtgt   2700
cgcccttatt ccctttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
tttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagacaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
```

```
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga gaaaggcgga   4140
caggtatccg gtaagcggca gggtcggaac aggagagcgc acgagggagc ttccagggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggccttttt   4320
acggttcctg gccttttgct ggccttttgc tcacatgttc tttcctgcgt tatccctga    4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg ccccgcctgg ctgaccgccc aacgacccc    4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgccccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tcccccccct   5100
ccccacccc aattttgtat ttatttattt tttaattatt ttgtgcagcg atggggggcg   5160
ggggggggg gggcgcgcgc caggcggggc ggggcggggc gaggggcggg gcggggcggg   5220
gcggagaggt gcggcggcag ccaatcagag cggcgcgctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccggttttg gcgcctccgc   5460
cgggcgcccc cctcctcacg gcgagcgctg ccacgtcaga cgaagggcgc agcgagcgtc   5520
ctgatccttc cgcccggacg ctcaggacag cggcccgctg ctcataagac tcggccttag   5580
aacccccagta tcagcagaag gacattttag gacgggactt gggtgactct agggcactgg   5640
ttttcttcc agagagcgga acaggcgagg aaaagtagtc ccttctcggc gattctgcg     5700
agggatctcc gtggggcggt gaacgccgat gatgcctcta ctaaccatgt tcatgttttc   5760
tttttttttc tacaggtcct gggtgacgaa cagggtaccg ccaccatggc caccggctct   5820
cgcacaagcc tgctgctggc tttcggactg ctgtgcctgc cttggctcca ggagggctcc   5880
gccgctagca tcgataccgt cgctatgtgc tggaggcttg ctgaaggctg tatgctgatc   5940
aatcggattg cggtaatcgc gttttggcct ctgactgacg cgattaccga tccgattgat   6000
caggacacaa ggcctgttac tagcactcac atggaacaaa tggcctctag cctggaggct   6060
tgctgaaggc tgtatgctga tctttgctaa attggtgcac gcgtttggc ctctgactga    6120
cgcgtgcacc attagcaaag atcaggacac aaggcctgtt actagcactc acatggaaca   6180
aatggcctct agcctggagg cttgctgaag gctgtatgct gacttcaatc acaattccag   6240
cgccgttttg gcctctgact gacgcgctg gaagtgattg aagtcaggac acaaggcctg    6300
ttactagcac tcacatggaa caaatggcct ctctagaat                          6339
```

SEQ ID NO: 15          moltype = DNA   length = 6339
FEATURE                Location/Qualifiers
source                 1..6339
                       mol_type = other DNA
                       organism = synthetic construct
SEQUENCE: 15

```
aatcaacctc tggattacaa aatttgtgaa agattgactg gtattcttaa ctatgttgct   60
cctttacgc tatgtggata cgctgcttta atgcctttgt atcatgctat tgcttcccgt     120
atggctttca ttttctcctc cttgtataaa tcctggttcg tgtctcttta tgaggagttg    180
tggcccgttg tcaggcaacg tggcgtggtg tgcactgtgt ttgctgacgc aaccccccat    240
ggttggggca ttgccaccac ctgtcagctc ctttccggga ctttcgcttt ccccctccct    300
attgccacgc cggaactcat cgccgcctgc cttgcccgct gctggacagg ggctcggctg    360
ttgggcactg acaattccgt ggtgttgtcg gggaaatcat cgtcctttcc ttggctgctc    420
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc taagcttatc    600
gataccgtca agatctaact tgtttattgc agcttataat ggttacaaat aaagcaatag    660
catcacaaat ttcacaaata aagcattttt ttcactgcat tctagttgtg gtttgtccaa    720
actcatcaat gtatcttatc atgtctggat ctcgacctcg actagagcat ggctacgtag    780
ataagtagca tggcgggtta atcattaact acaaggaacc cctagtgatg gagttggcca    840
ctccctctct gcgcgctcgc tcgctcactg aggccgggcg accaaaggtc gcccgacgcc    900
cgggctttgc ccgggcggcc tcagtgagcg agcgagcgcg cagctggcgt aatagcgaag    960
aggcccgcac cgatcgccct tcccaacagt tgcgcagcct gaatggcgaa tggcgattcc    1020
gttgcaatgg ctggcggtaa tattgttctg gatattacca gcaaggccga tagtttgagt    1080
tcttctactc aggcaagtga tgttattact aatcaaagaa gtattgcgac aacgttaat    1140
ttgcgtgatg acagactct ttactcggt ggcctcactg attataaaaa cacttctcag      1200
gattctggcg taccgttcct gtctaaaatc cctttaatgc gcctcctgtt tagctcccgc    1260
tctgattcta acgaggaaag cacgttatac gtgctcgtca aagcaaccat agtacgcgcc    1320
ctgtagcggc gcattaagcg cggcgggtgt ggtggttacg cgcagcgtga ccgctacact    1380
tgccagcgcc ctagcgcccg ctcctttcgc tttcttccct tccttctcg ccacgttcgc     1440
cggctttccc cgtcaagctc taaatcgggg ctccctttag ggttccgat ttagtgcttt      1500
acggcaccc gaccccaaaa aacttgatta gggtgatggt tcacgtagtg ggccatcgcc     1560
ctgatagacg gtttttcgcc ctttgacgtt ggagtccacg ttctttaata gtggactctt    1620
gttccaaact ggaacaacac tcaaccctat ctcggtctat tcttttgatt tataagggat    1680
tttgccgatt tcggcctatt ggttaaaaaa tgagctgatt taacaaaaat ttaacgcgaa    1740
ttttaacaaa atattaacgt ttacaattta aatatttgct tatacaatct tcctgttttt    1800
ggggcttttc tgattatcaa ccggggtaca tatgattgac atgctagttt tacgattacc    1860
```

-continued

```
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt taaaatatat gagggttcta aaaattttta tccttgcgtt   2100
gaaataaagg cttctcccgc aaaagtatta cagggtcata atgttttttg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctattttat aggttaatgt   2520
catgataata atggtttctt agacgtcagg tggcactttt cggggaaatg tgcgcggaac   2580
ccctatttgt ttatttttct aaatacattc aaatatgtat ccgctcatga gacaataacc   2640
ctgataaatg cttcaataat attgaaaaag gaagagtatg agtattcaac atttccgtgt   2700
cgcccttatt cccttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
tttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acgggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg ggggttcgt gcacacagcc cagcttggag cgaacgacct acaccgaact   4080
gagatacccta cagcgtgagc tatgagaaag cgccacgctt cccgaaggga gaaaggcgga   4140
caggtatccg gtaagcggca gggtcggaac aggagagcgc acgagggagc ttccagggga   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggcctttt   4320
acggttcctg gccttttgct ggccttttgc tcacatgttc tttcctgcgt tatccccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgacccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgcccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tccccccct   5100
ccccaccccc aattttgtat ttatttattt tttaattatt ttgtgcagcg atgggggcgg   5160
gggggggggg gggcgcgcgc caggcggggc ggggcggggc gaggggcggg gcggggcgag   5220
gcggagaggt gcggcggcag ccaatcagag cggcgcgctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg cggggttttg cgcctcccg   5460
cgggcgcccc cctcctcacg cgagcgctg ccacgtcaga cgaagggcgc agcgagcgtc   5520
ctgatccttc cgcccggacg ctcaggacag cggcccgctg ctcataagac tcggccttag   5580
aaccccagta tcagcagaag gacattttag gacgggactt gggtgactct agggcactgg   5640
ttttccttcc agagagtgga acaggcgagg aaaagtagtc cttctcggc gattctgacg   5700
agggatctcc gtggggcggt gaacgccgat gatgcctcta ctaaccatgt tcatgttttc   5760
tttttttttc tacaggtcct gggtgacgaa cagggtaccg ccaccatggc caccggctct   5820
cgcacaagcc tgctgctggc tttcggactg ctgtgcctgc cttggctcca ggagggctcc   5880
gccgctagca tcgataccgt cgctatgtgc tggaggcttg ctgaaggctg tatgctgtaa   5940
tctttcgcgtg gctgcagttc gttttggcct ctgactgacg aactgcagcg cgaaagatta   6000
caggacacaa ggcctgttac tagcactcac atggaacaaa tggcctctag cctgtgaggct   6060
tgctgaaggc tgtatgctgt gttaatgcta atgtcacgct gcgttttggc ctctgactga   6120
cgcagcgtga ccagcattaa cacaggacac aaggcctgtt actagcactc acatggaaca   6180
aatggcctct agcctggagg cttgctgaag gctgtatgct gttcacctgg ttaacacata   6240
caccgttttg gctctgact gacggtgtat gtgaaccagg tgaacaggac acaaggcctg   6300
ttactagcac tcacatggaa caaatggcct ctctagaat                         6339
```

```
SEQ ID NO: 16        moltype = DNA   length = 6339
FEATURE              Location/Qualifiers
source               1..6339
```

-continued

```
                    mol_type = other DNA
                    organism = synthetic construct
SEQUENCE: 16
aatcaacctc tggattacaa aatttgtgaa agattgactg gtattcttaa ctatgttgct   60
ccttttacgc tatgtggata cgctgcttta atgcctttgt atcatgctat tgcttcccgt  120
atggctttca ttttctcctc cttgtataaa tcctggttgc tgtctctttta tgaggagttg  180
tggcccgttg tcaggcaacg tggcgtggtg tgcactgtgt ttgctgacgc aacccccact  240
ggttggggca ttgccaccac ctgtcagctc cttttccggga ctttcgcttt cccctccct   300
attgccacgg cggaactcat cgccgcctgc cttgcccgct gctggacagg ggtcggctg   360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctcccccgcc taagcttatc  600
gataccgtcg agatctaact tgtttattgc agcttataat ggttacaaat aaagcaatag  660
catcacaaat ttcacaaata aagcatttt ttcactgcat tctagttgtg gtttgtccaa  720
actcatcaat gtatccttatc atgtctggat ctcgacctcg actagagcat ggctacgtag  780
ataagtagca tggcgggtta atcattaact acaaggaacc cctagtgatg gagttggcca  840
ctccctctct gcgcgctcgc tcgctcactg aggccggcgg accaaaggtc gcccgacgcc  900
cgggctttgc ccgggcggcc tcagtgagcg agcgagcgcg cagctggcgt aatagcgaag  960
aggcccgcac cgatcgccct tcccaacagt tgcgcagcct gaatggcgaa tggcgattcc 1020
gttgcaatgg ctggcggtaa tattgttctg gatattacca gcaaggccga tagtttgagt 1080
tcttctactc aggcaagtga tgttattact aatcaaagaa gcttgcgac aacggttaat 1140
ttgcgtgatg gacagactct tttactcggt ggcctcactg attataaaaa cacttctcag 1200
gattctggcg taccgttcct gtctaaaatc cctttaatcg gcctcctgtt tagctcccgc 1260
tctgattcta acgaggaaag cacgttatac gtgctcgtca aagcaaccat agtacgcgcc 1320
ctgtagcggc gcattaagcg cggcgggtgt ggtggttacg cgcagcgtga ccgctacact 1380
tgccagcgcc ctagcgcccg ctcctttcgc tttcttccct tccttttctcg ccacgttcgc 1440
cggctttccc cgtcaagctc taaatcgggg gctccctta gggttccgat ttagtgcttt 1500
acggcacctc gaccccaaaa aacttgatta gggtgatggt tcacgtagtg ggccatcgcc 1560
ctgatagacg gttttcgcc ctttgacgtt ggagtccacg ttctttaata gtggactctt 1620
gttccaaact ggaacaacac tcaaccctat ctcggtctat tcttttgatt tataagggat 1680
tttgccgatt tcggcctatt ggttaaaaaa tgagctgatt taacaaaaat ttaacgcgaa 1740
ttttaacaaa atattaacgt ttacaattta aatatttgct tatacaatct tcctgttttt 1800
ggggcttttc tgattatcaa ccggggtaca tatgattgac atgctagttt tacgattacc 1860
gttcatcgat tctcttgttt gctccagact ctcaggcaat gacctgatag cctttgtaga 1920
gacctctcaa aaatagctac cctctccggc atgaatttat cagctagaac ggttgaatat 1980
catattgatg gtgatttgac tgtctccggc ctttctcacc cgtttgaatc tttacctaca 2040
cattactcag gcattgcatt taaaatatat gagggttcta aaaattttta tccttgcgtt 2100
gaaataaagg cttctcccgc aaaagtatta cagggtcata atgtttttgg tacaaccgat 2160
ttagctttat gctctgaggc tttattgctt aattttgcta attctttgcc ttgcctgtat 2220
gatttattgg atgttggaat tcctgatgcg gtattttctc cttacgcatc tgtgcggtat 2280
ttcacaccgc atatggtgca ctctcagtac aatctgctct gatgccgcat agttaagcca 2340
gccccgacac ccgccaacac ccgctgacgc gccctgacgg gcttgtctgc tcccggcatc 2400
cgcttacaga caagctgtga ccgtctccgg gagctgcatg tgtcagaggt tttcaccgtc 2460
atcaccgaaa cgcgcgagac gaaagggcct cgtgatacgc ctattttttat aggttaatgt 2520
catgataata atggtttctt agacgtcagg tggcactttt cggggaaatg tgcgcggaac 2580
ccctatttgt ttatttttct aaatacattc aaatatgtat ccgctcatga gacaataacc 2640
ctgataaatg cttcaataat attgaaaaag gaagagtatg agtattcaac atttccgtgt 2700
cgcccttatt cccttttttg cggcatttttg ccttcctgtt tttgctcacc cagaaacgct 2760
ggtgaaagta aaagatgctg aagatcagtt gggtgcacga gtgggttaca tcgaactgga 2820
tctcaacagc ggtaagatcc ttgagagttt tcgccccgaa gaacgtttttc caatgatgag 2880
cacttttaaa gttctgctat gtggcgcggt attatcccgt attgacgccg ggcaagagca 2940
actcggtcgc cgcatacact attctcagaa tgacttggtt gagtactcac cagtcacaga 3000
aaagcatctt acggatggca tgacagtaag agaattatgc agtgctgcca taaccatgag 3060
tgataacact gcggccaact tacttctgac aacgatcgga ggaccgaagg agctaaccgc 3120
ttttttgcac aacatggggg atcatgtaac tcgccttgat cgttgggaac cggagctgaa 3180
tgaagccata ccaaacgacg agcgtgacac cacgatgcct gtagcaatgg caacaacgtt 3240
gcgcaaacta ttaactggcg aactacttac tctagcttcc cggcaacaat taatagactg 3300
gatggaggcg gataaagttg caggaccact tctgcgctcg gcccttccgg ctggctggtt 3360
tattgctgat aaatctggag ccggtgagcg tgggtctcgc ggtatcattg cagcactggg 3420
gccagatggt aagccctccc gtatcgtagt tatctacacg acggggagtc aggcaactat 3480
ggatgaacga aatagacaga tcgctgagat aggtgcctca ctgattaagc attggtaact 3540
gtcagaccaa gtttactcat atatacttta gattgattta aaacttcatt tttaatttaa 3600
aaggatctag gtgaagatcc tttttgataa tctcatgacc aaaatccctt aacgtgagtt 3660
ttcgttccac tgagcgtcag accccgtaga aagatcaaa ggatcttctt gagatccttt 3720
ttttctgcgc gtaatctgct gcttgcaaac aaaaaaacca ccgctaccag cggtggtttg 3780
tttgccggat caagagctac caactctttt tccgaaggta actggcttca gcagagcgca 3840
gataccaaat actgtccttc tagtgtagcc gtagttaggc caccacttca agaactctgt 3900
agcaccgcct acatacctcg ctctgctaat cctgttacca gtggctgctg ccagtggcga 3960
taagtcgtgt cttaccgggt tggactcaag acgatagtta ccggataagg cgcagcggtc 4020
gggctgaacg gggggttcgt gcacacagcc cagcttggag cgaacgacct acaccgaact 4080
gagatacctta cagcgtgagc tatgagaaag cgccacgctt cccgaaggga aaaggcgga 4140
caggtatccg gtaagcggca gggtcggaac aggagagcgc acgagggagc ttccaggggg 4200
aaacgcctgg tatctttata gtcctgtcgg gtttcgccac ctctgacttg agcgtcgatt 4260
tttgtgatgc tcgtcagggg ggcggagcct atgggaaaaac gccagcaacg cggcctttttt 4320
acggttcctg gccttttgct ggccttttgc tcacatgttc tttcctgcgt tatccctga 4380
ttctgtggat aaccgtatta ccgcctttga gtgagctgat accgctcgcc gcagccgaac 4440
gaccgagcgc agcgagtcag tgagcgagga agcggaagag cgcccaatac gcaaaccgcc 4500
tctccccgcg cgttggccga ttcattaatg cagcagctgc gcgctcgctc gctcactgag 4560
```

```
gccgcccggg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgacccc    4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgcccct attgacgtca atgacggtaa atggcccgcc tggcattatg    4980
cccagtacat gaccttatgg gactttccta cttggcagta catctacgta ttagtcatcg   5040
ctattaccat ggtcgaggtg agccccacgt tctgcttcac tctcccccatc tcccccccct   5100
ccccaccccc aattttgtat ttatttattt tttaattatt ttgtgcagcg atggggcgg    5160
ggggggggggg gggcgcgcgc caggcggggc ggggcggggc gaggggcggg gcggggcgag   5220
gcggagaggt gcggcggcag ccaatcagag cggcgcgctc cgaaagtttc cttttatggc   5280
gaggcggcgg cggcggcggc cctataaaaa gcgaagcgcg cggcgggcgg gagtcgctgc   5340
gcgctgcctt cgcccgtgc cccgctccgc cgccgcctg cgccgcccgc cccggctctg    5400
actgaccgcg ttactaaaac aggtaagtcc ggcctccgcg ccgggttttg gcgcctcccg   5460
cgggcgcccc cctcctcacg gcgagcgctg ccacgtcaga cgaagggcgc agcgagcgtc   5520
ctgatccttc cgcccggacg ctcaggacag cggcccgctg ctcataagac tcggccttag   5580
aaccccagta tcagcagaag gacattttag gacgggactt gggtgactct agggcactgg   5640
ttttctttcc agagagcgga acaggcgagg aaaagtagtc ccttctcggc gattctgcgg   5700
agggatctcc gtggggcggt gaacgccgat gatgcctcta ctaaccatgt tcatgttttc   5760
tttttttttc tacaggtcct gggtgacgaa cagggtaccg ccaccatggc caccggctct   5820
cgcacaagcc tgctgctggc tttcgactg ctgtgcctgc cttggctcca ggagggctcc   5880
gccgctagca tcgataccgt cgctatgtgc tggaggcttg ctgaaggctg tatgctgatt   5940
tcttcctgtg cgctttcgcc gttttggcct ctgactgacg gcgaaagcgc aggaagaaat   6000
caggacacaa ggcctgttac tagcactcac atggaacaaa tggcctctag cctggaggct   6060
tgctgaaggc tgtatgctga gaataatcag atcagcacgt tcgttttgcc ctctgactga   6120
cgagcgtgct gctgattatt ctcaggacac aaggcctgtt actagcactc acatggaaca   6180
aatgccctct agcctggagg cttgctgaag gctgtatgct gtaatcaggc tgaattcaga   6240
tagcgttttg gcctctgact gacgctatct gaacagcctg attacaggac acaaggcctg   6300
ttactagcac tcacatggaa caaatggcct ctctagaat                          6339
```

SEQ ID NO: 17           moltype = DNA   length = 6339
FEATURE                 Location/Qualifiers
source                  1..6339
                        mol_type = other DNA
                        organism = synthetic construct
SEQUENCE: 17

```
aatcaacctc tggattacaa aatttgtgaa agattgactg gtattcttaa ctatgttgct     60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aacccccact    240
ggttggggca ttgccaccac ctgtcagctc cttccgggga ctttcgcttt cccctcct     300
attgccacgg cggaactcat cgccgcctgc cttgcccgct gctggacagg ggctcggctg    360
ttgggcactg acaattccgt ggtgttgtcg gggaaatcat cgtcctttcc ttggctgctc    420
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc taagcttatc     600
gataccgtcg agatctaact tgtttattgc agcttataat ggttacaaat aaagcaatag    660
catcacaaat ttcacaaata aagcattttt ttcactgcat tctagttgtg gtttgtccaa    720
actcatcaat gtatcttatc atgtctggat ctcgacctcg actagagcat ggctacgtag    780
ataagtagca tggcgggtta atcattaact acaaggaacc cctagtgatg gagttggcca    840
ctccctctct gcgcgctcgc tcgctcactg aggccgggcg accaaaggtc gcccgacgcc    900
cgggctttgc ccgggcggcc tcagtgagcg agcgagcgcg cagctggcgt aatagcgaag    960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgtgtattact aatcaaagaa gtattgcgac aacggttaat   1140
ttgcgtgatg gacagactct tttactcggt ggcctcactg attataaaaa cacttctcag   1200
gattctggcg taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg ctcccttta gggttccgat ttagtgcttt    1500
acggcacctc gaccccaaaa aacttgatta gggtgatggt tcacgtagtg gccatcgcc    1560
ctgatagacg gtttttcgcc ctttgacgtt ggagtccacg ttctttaata gtggactctt   1620
gttccaaact ggaacaacac tcaaccctat ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg tgatttgac tgtctccggc ctttctcacc cgtttgaatc tttacctaca    2040
cattactcag gcattgcatt taaaatatat gagggttcta aaaattttta tccttgcgtt   2100
gaaataaagg cttctcccgc aaaagtatta cagggtcata atgtttttgg tacaaccgat   2160
ttagctttat gctctgaggc tttattgctt aattttgcca ttccttgcgg tgcctctaa    2220
gatttattgg atgttggaat cctgatgcg gtatttttctc cttacgcatc tgtgcggtat    2280
ttcacaccgc atatggtgca ctctcagtac aatctgctct gatgccgcat agttaagcca   2340
gccccgacac cgccaacac ccgctgacgc gccctgacgg gcttgtctgc tcccggcatc    2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
```

-continued

```
catgataata atggtttctt agacgtcagg tggcactttt cggggaaatg tgcgcggaac   2580
ccctatttgt ttattttct aaatacattc aaatatgtat ccgctcatga gacaataacc   2640
ctgataaatg cttcaataat attgaaaaag gaagagtatg agtattcaac atttccgtgt   2700
cgcccttatt cccttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cactttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
tttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctgttt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggcctttt   4320
acggttcctg gccttttgct ggccttttgc tcacatgttc tttcctgcgt tatccccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgacccccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgcccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tcccccccc   5100
ccccacccc aattttgtat ttatttattt tttaattatt ttgtgcagcg atggggggcgg   5160
gggggggggg gggcgcgcgc caggcggggc ggggcggggc gaggggcggg gcggggcgag   5220
gcggagaggt gcggcggcag ccaatcagag cggcgcgctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg cgagcgctg ccacgtcaga cgaagggcgc agcgagcgtc   5520
ctgatccttc cgcccggacg ctcaggacag cggcccgctg ctcataagac tcggccttag   5580
aaccccagta tcagcagaag gacatttag gacgggactt gggtgactct agggcactgg   5640
ttttctttcc agagagcgga acaggcgagg aaaagtagtc ccttctcggc gattctgcgg   5700
agggatctcc gtggggcggt gaacgccgat gatgcctcta ctaaccatgt tcatgttttc   5760
tttttttttc tacaggtcct gggtgacgaa cagggtaccg ccaccatggc caccggctct   5820
cgcacaagcc tgctgctggc tttcggactg ctgtgcctgc cttggctcca ggaggggctcc   5880
gccgctagca tcgataccgt cgctatgtgc tggaggcttg ctgaaggctg tatgctgata   5940
atcaccgctg caggttcagc gttttggcct ctgactgacg ctgaacctgg cggtgattat   6000
caggacacaa ggcctgttac tagcactcac atggaacaaa tggcctctag cctggaggct   6060
tgctgaaggc tgtatgctgt tcaatcgcgt attggtaatc gcgttttgac ctctgactga   6120
cgcgattacc aacgcgattg aacaggacac aaggcctgtt actagcactc acatggaaca   6180
aatgccctct agcctggagg cttgctgaag gctgtatgct gtgatcatgc tgaaaatggt   6240
gcacgttttg gcctctgact gacgtgcacc attcagcatg atcacaggac acaaggcctg   6300
ttactagcac tcacatggaa caaatggcct ctctagaat                          6339
```

```
SEQ ID NO: 18            moltype = DNA   length = 6339
FEATURE                 Location/Qualifiers
source                  1..6339
                        mol_type = other DNA
                        organism = synthetic construct
SEQUENCE: 18
aatcaacctc tggattacaa aatttgtgaa agattgactg gtattcttaa ctatgttgct   60
cctttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccccact   240
ggttggggca ttgccaccac ctgtcagctc ctttccggga ctttcgcttt ccccctcctt   300
attgccacgc cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
```

-continued

```
aatccagcgg accttccttc ccgcggcctg ctgccggctc tgcggcctct tccgcgtctt    540
cgccttcgcc ctcagacgag tcggatctcc ctttgggccg cctccccgcc taagcttatc    600
gataccgtcg agatctaact tgtttattgc agcttataat ggttacaaat aaagcaatag    660
catcacaaat ttcacaaata aagcattttt ttcactgcat tctagttgtg gtttgtccaa    720
actcatcaat gtatcttatc atgtctggat ctcgacctcg actagagcat ggctacgtag    780
ataagtagca tggcgggtta atcattaact acaaggaacc cctagtgatg gagttggcca    840
ctccctctct gcgcgctcgc tcgctcactg aggccgggcg accaaaggtc gcccgacgcc    900
cgggctttgc ccgggcggcc tcagtgagcg agcgagcgcg cagctggcgt aatagcgaag    960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggcg taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg gctcccttta gggttccgat ttagtgcttt   1500
acggcacctc gaccccaaaa aacttgatta gggtgatggt tcacgtagtg ggccatcgcc   1560
ctgatagacg gtttttcgcc ctttgacgtt ggagtccacg ttctttaata gtggactctt   1620
gttccaaact ggaacaacac tcaaccctat ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt taaaatatat gagggttcta aaaattttta tccttgcgtt   2100
gaaataaagg cttctcccgc aaaagtatta cagggtcata atgtttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcactttt cggggaaatg tgcgcggaac   2580
ccctatttgt ttatttttct aaatacattc aaatatgtat ccgctcatga gacaataacc   2640
ctgataaatg cttcaataat attgaaaaag gaagagtatg agtattcaac atttccgtgt   2700
cgcccttatt cccttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
ttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acgggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga aaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggcctttt   4320
acggttcctg gccttttgct ggccttttgc tcacatgttc tttcctgcgt tatccccttga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcgcgg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgacccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgccccct attgacgtca atgacgtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tcccccccct   5100
ccccacccc aattttgtat ttatttattt tttaattatt ttgtgcagcg atggggggcgg   5160
gggggggggg ggcgcgcgc caggcggggc ggggcggggc gaggggcggg gcggggcgag   5220
```

-continued

```
gcggagaggt gcggcggcag ccaatcagag cggcgcgctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg gcgagcgctg ccacgtcaga cgaagggcgc agcgagcgtc   5520
ctgatccttc cgcccggacg ctcaggacag cggcccgctg ctcataagac tcggccttag   5580
aaccccagta tcagcagaag gacattttag gacgggactt gggtgactct agggcactgg   5640
ttttctttcc agagagcgga acaggcgagg aaaagtagtc ccttctcggc gattctgcgg   5700
agggatctcc gtggggcggt gaacgccgat gatgcctcta ctaaccatgt tcatgttttc   5760
tttttttttc tacaggtcct gggtgacgaa cagggtaccg ccaccatggc caccggctct   5820
cgcacaagcc tgctgctggc tttcggactg ctgtgcctgc cttggctcca ggagggctcc   5880
gccgctagca tcgataccgt cgctatgtgc tggaggcttg ctgaaggctg tatgctgagg   5940
taatatcctg acgctcagcc gttttggcct ctgactgacg gctgagcgtg gatattacct   6000
caggacacaa ggcctgttac tagcactcac atggaacaaa tggcctctag cctggaggct   6060
tgctgaaggc tgtatgctgt acagaatcag ataatcagcg ccgtttttggc ctctgactga   6120
cggcgctgat tctgattctg tacaggacac aaggcctgtt actagcactc acatggaaca   6180
aatggcctct agcctggagg cttgctgaag gctgtatgct gtcatgttta aaaattcgct   6240
gcgcgttttg gcctctgact gacgcgcagc gaatttaaac atgacaggac acaaggcctg   6300
ttactagcac tcacatggaa caaatggcct ctctagaat   6339
```

SEQ ID NO: 19       moltype = DNA   length = 6339
FEATURE             Location/Qualifiers
source              1..6339
                    mol_type = other DNA
                    organism = synthetic construct
SEQUENCE: 19

```
aatcaacctc tggattacaa aatttgtgaa agattgactg gtattcttaa ctatgttgct   60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aacccccact   240
ggttgggggca ttgccaccac ctgtcagctc ctttccggga ctttcgcttt cccccctccct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcattttt ttcactgcat tctagttgtg gtttgtccaa   720
actcatcaat gtatcttatc atgtctggat ctcgacctcg actagagcat ggctacgtag   780
ataagtagca tggcgggtta atcattaact acaaggaacc cctagtgatg gagttggcca   840
ctccctctct gcgcgctcgc tcgctcactg aggccgggcg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggcg taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg gctccctttta gggttccgat ttagtgcttt   1500
acggcacctc gaccccaaaa aacttgatta gggtgatggt tcacgtagtg ggccatcgcc   1560
ctgatagacg gttttttcgcc ctttgacgtt ggagtccacg ttctttaata gtggactctt   1620
gttccaaact ggaacaacac tcaacccttat ctcggtctat tctttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt aaaaatatat gagggttcta aaaatttta tccttgcgtt   2100
gaaataaagg cttctcccgc aaaagtatta cagggtcata atgtttttgg tacaaccgat   2160
ttagcttttat gctctgaggc tttattgctt aattttgcta attctttgcc ttgcctgtat   2220
gatttattgg aat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcactttt cggggaaatg tgcgcggaac   2580
ccctatttgt ttatttttct aaatacattc aaatatgtat ccgctcatga caataacc   2640
ctgataaatg cttcaataat attgaaaaag gaagagtatg agtattcaac atttccgtgt   2700
cgcccttatt cccttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
ttttttgcac aacatggggg atcatgtaac tcgccttgat cgttgggaac cggagctgaa   3180
```

```
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctcgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggccttttt   4320
acggttcctg gccttttgct ggccttttgc tcacatgttc tttcctgcgt tatcccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtga   4740
agttccgcgt tacataactt acggtaaatg gcccgcctgg ctgaccgccc aacgacccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgccccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tccccccct   5100
ccccacccc aattttgtat ttatttattt tttaattatt ttgtgcagcg atgggggcgg   5160
ggggggggg gggcgcgcgc caggcggggc ggggcggggc gaggggcggg gcggggcgag   5220
gcggagaggt gcggcggcag ccaatcagag cggcggctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg gcgagcgctg ccacgtcaga cgaagggcgc agcgagcgtc   5520
ctgatccttc cgcccggacg ctcaggacag cggcccgctg ctcataagac tcggccttag   5580
aacccccagta tcagcagaag gacattttag gacgggactt gggtgactct agggcactgg   5640
ttttctttcc agagagcgga acaggcgagg aaaagtagtc ccttctcggc gattctgcgg   5700
agggatctcc gtggggcggt gaacgccgat gatgcctcta ctaaccatgt tcatgtttc   5760
ttttttttc tacaggtcct gggtgacgaa cagggtaccg ccaccatggc caccggctct   5820
cgcacaagcc tgctgctggc tttcggactg ctgtgcctgc cttggctcca ggagggctcc   5880
gccgctagca tcgataccgt cgctatgtgc tggaggcttg ctgaaggctg tatgctgatg   5940
aatcgggttg tctgaatcgc gttttggcct ctgactgacg cgattcagaa cccgattcat   6000
caggacacaa ggcctgttac tagcactcac atggaacaaa tggcctctag cctgtgaggct   6060
tgctgaaggc tgtatgctga acactttgct atatcatcct gcgttttggc ctctgactga   6120
cgcaggatga tagcaaagtg ttcaggacac aaggcctgtt actagcactc acatggaaca   6180
aatgcctct agcctggagg cttgctgaag gctgtatgct gttctgttcg ttaagctaat   6240
gctcgttttg gcctctgact gacgagcatt agcaacgac agaacaggac acaaggcctg   6300
ttactagcac tcacatggaa caaatggcct ctctagaat                          6339
```

```
SEQ ID NO: 20          moltype = DNA   length = 6339
FEATURE                Location/Qualifiers
source                 1..6339
                       mol_type = other DNA
                       organism = synthetic construct
SEQUENCE: 20
aatcaacctc tggattacaa aatttgtgaa agattgactg gtattcttaa ctatgttgct   60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aacccccact   240
ggttggggca ttgccaccac ctgtcagctc ctttccggga ctttcgcttt ccccctccct   300
attgccacgg cggaactcat cgccgcctgc cttcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcatttt ttcactgcat tctagttgtg gtttgtccaa   720
actcatcaat gtatcttatc atgtctggat ctcgacctcg actagagcat ggctacgtag   780
ataagtagca tggcgggtta atcattaact acaaggaacc cctagtgatg gagttggcca   840
ctccctctct gcgcgctcgc tcgctcactg aggccggcg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa gtattgcgac aacggttaat   1140
```

-continued

```
ttgcgtgatg gacagactct tttactcggt ggcctcactg attataaaaa cacttctcag   1200
gattctggcg taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg gctcccttta gggttccgat ttagtgcttt   1500
acggcacctc gaccccaaaa aacttgatta gggtgatggt tcacgtagtg ggccatcgcc   1560
ctgatagacg gtttttcgcc ctttgacgtt ggagtccacg ttctttaata gtggactctt   1620
gttccaaact ggaacaacac tcaaccctat ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttaacctaca   2040
cattactcag gcattgcatt taaaatatat gagggttcta aaaattttta tccttgcgtt   2100
gaaataaagg cttctcccgc aaaagtatta cagggtcata atgttttgg tacaaccgat   2160
ttagctttat gctctgaggc tttattgctt aattttgcta attctttgcc ttgcctgtat   2220
gatttattgg atgttggaat tcctgatgcg gtatttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctattttat aggttaatgt   2520
catgataata atggtttctt agacgtcagg tggcactttt cggggaaatg tgcgcggaac   2580
ccctatttgt ttatttttct aaatacattc aaatatgtat ccgctcatga gacaataacc   2640
ctgataaatg cttcaataat attgaaaaag gaagagtatg agtattcaac atttccgtgt   2700
cgcccttatt ccctttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgtttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
ttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatcctt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtcctc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga gaaaggcgga   4140
caggtatccg gtaagcggca gggtcggaac aggagagcgc acgagggagc ttccagggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggccttttt   4320
acggttcctg gccttttgct ggccttttgc tcacatgttc tttcctgcgt tatcccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctaggc cattgattat tgactagtga   4740
agttccgcgt tacataactt acggtaaatg gcccgcctgg ctgaccgccc aacgacccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgccccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tcccccccct   5100
ccccaccccc aattttgtat ttatttattt ttaattattt ttgtgcagcg atgggggcgg   5160
gggggggggg gggcgcgcgc caggcggggc ggggcggggc gaggggcggg gcggggcgag   5220
gcggagaggt gcggcggcag ccaatcagag cggcgcgctc cgaaagtttc ctttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg gcgagcgctg ccacgtcaga cgaagggcgc agcgagcgtc   5520
ctgatccttc cgcccgacg ctcaggacag cggcccgctg ctcataagac tcggccttag   5580
aaccccagta tcagcagaag gacatttag gacgggactt gggtgactct agggcactgg   5640
ttttctttcc agagagcgga acaggcgagg aaaagtagtc ccttctcggc gattctgcgg   5700
agggatctcc gtggggcggt gaacgccgat gatgcctcta ctaaccatgt tcatgttttc   5760
tttttttttc tacaggtcct gggtgacgaa cagggtaccg ccaccatggc caccggctct   5820
cgcacaagcc tgctgctggc tttcggactg ctgtgcctgc cttggctcca ggagggctcc   5880
```

```
gccgctagca tcgataccgt cgctatgtgc tggaggcttg ctgaaggctg tatgctggag   5940
cattagcaat gcgaacagaa gttttggcct ctgactgact tctgttcgtt gctaatgctc   6000
caggacacaa ggcctgttac tagcactcac atggaacaaa tggcctctag cctggaggct   6060
tgctgaaggc tgtatgctga aacataatgg attcagcagc gcgtttggc ctctgactga    6120
cgcgctgctg accattatgt ttcaggacac aaggcctgtt actagcactc acatggaaca   6180
aatggcctct agcctggagg cttgctgaag gctgtatgct gttatctttg cgaagctgcc   6240
atccgttttg gcctctgact gacggatggc agccgcaaag ataacaggac acaaggcctg   6300
ttactagcac tcacatggaa caaatggcct ctctagaat                         6339

SEQ ID NO: 21          moltype = DNA  length = 6337
FEATURE                Location/Qualifiers
source                 1..6337
                       mol_type = other DNA
                       organism = synthetic construct
SEQUENCE: 21
aatcaacctc tggattacaa aatttgtgaa agattgactg gtattcttaa ctatgttgct     60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccccact   240
ggttgggggca ttgccaccac ctgtcagctc ctttccggga ctttcgcttt cccctccct    300
attgccacgg cggaactcat cgccgcctgc cttgcccgct gctggacagg ggctcggctg    360
ttgggcactg acaattccgt ggtgttgtcg gggaaatcat cgtcctttcc ttggctgctc    420
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc taagcttatc    600
gataccgtcg agatctaact tgtttattgc agcttataat ggttacaaat aaagcaatag    660
catcacaaat ttcacaaata aagcatttt ttcactgcat tctagttgtg gtttgtccaa     720
actcatcaat gtatcttatc atgtctggat ctcgacctcg actagagcat ggctacgtag    780
ataagtagca tggcgggtta atcattaact caaggaacc cctagtgatg gagttggcca     840
ctccctctct gcgcgctcgc tcgctcactg aggccgcgcg accaaaggtc gcccgacgcc     900
cgggctttgc ccgggcggcc tcagtgagcg agcgagcgcg cagctggcgt aatagcgaag     960
aggcccgcac cgatcgccct tcccaacagt tgcgcagcct gaatggcgaa tggcgattcc    1020
gttgcaatgc ctggcggtaa tattgttctg gatattacca gcaaggccga tagtttgagt    1080
tcttctactc aggcaagtga tgttattact aatcaaagaa gacttgcgac aacggttaat   1140
ttgcgtgatg gacagactct tttactcggt ggcctcactg attataaaaa cacttctcag   1200
gattctggcg taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg ctcccctta gggttccgat ttagtgcttt     1500
acggcacctc gaccccaaaa aacttgatta gggtgatggt tcacgtagtg ggccatcgcc   1560
ctgatagacg gtttttcgcc ctttgacgtt ggagtccacg ttctttaata gtggactctt   1620
gttccaaact ggaacaacac tcaaccctat ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacggattacc  1860
gttcatcgat tctcttgttt gctccagact tccaggcaat gacctgatag cctttgtaga   1920
gacctctcaa aaatagctac cctctccggc atgaatttat cagctagaac ggttgaatat   1980
catattgatg tgatttgac tgtctccggc ctttctcacc cgtttgaatc tttacctaca    2040
cattactcag gcattgcatt taaaatatat gagggttcta aaaattttta tccttgcgtt   2100
gaaataaagg cttctcccgc aaaagtatta cagggtcata atgtttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcactttt cggggaaatg tgcgcggaac   2580
ccctatttgt ttatttttct aaatacattc aaatatgtat ccgctcatga gacaataacc   2640
ctgataaatg cttcaataat attgaaaaag gaagagtatg agtattcaac atttccgtgt   2700
cgcccttatt cccttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
ttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga atagacagat cgctgagata ggtgcctcac tgattaagc attggtaact    3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
```

```
gataccaaat actgtccttc tagtgtagcc gtagttaggc caccacttca agaactctgt  3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg gggggttcgt gcacacagcc cagcttggag cgaacgacct acaccgaact  4080
gagataccta cagcgtgagc tatgagaaag cgccacgctt cccgaaggga gaaaggcgga  4140
caggtatccg gtaagcggca gggtcggaac aggagagcgc acgagggagc ttccaggggg  4200
aaacgcctgg tatctttata gtcctgtcgg gtttcgccac ctctgacttg agcgtcgatt  4260
tttgtgatgc tcgtcagggg ggcggagcct atggaaaaac gccagcaacg cggccttttt  4320
acggttcctg gccttttgct ggcctttgc tcacatgttc tttcctgcgt tatcccctga  4380
ttctgtggat aaccgtatta ccgcctttga gtgagctgat accgctcgcc gcagccgaac  4440
gaccgagcgc agcgagtcag tgagcgagga agcggaagag cgcccaatac gcaaaccgcc  4500
tctccccgcg cgttggccga ttcattaatg cagcagctgc gcgctcgctc gctcactgag  4560
gccgcccggg caaagcccgg gcgtcgggcg acctttggtc gcccggcctc agtgagcgag  4620
cgagcgcgca gagagggagt ggccaactcc atcactaggg gttccttgta gttaatgatt  4680
aacccgccat gctacttatc tacgtagcca tgctctagga cattgattat tgactagtgg  4740
agttccgcgt tacataactt acggtaaatg gcccgcctgg ctgaccgccc aacgaccccc  4800
gcccattgac gtcaataatg acgtatgttc ccatagtaac gccaataggg actttccatt  4860
gacgtcaatg ggtggagtat ttacggtaaa ctgcccactt ggcagtacat caagtgtatc  4920
atatgccaag tacgcccct attgacgtca atgacggtaa atggcccgcc tggcattatg  4980
cccagtacat gaccttatgg gactttccta cttggcagta catctacgta ttagtcatcg  5040
ctattaccat ggtcgaggtg agccccacgt tctgcttcac tctccccatc tccccccct  5100
ccccacccc aattttgtat ttatttattt tttaattatt ttgtgcagcg atggggggcgg  5160
ggggggggggg gggcgcgcgc caggcgggggc ggggcgggggc gaggggcggg gcggggcgag  5220
gcgggagaggt gcggcggcag ccaatcagag cggcgcgctc cgaaagtttc cttttatggc  5280
gaggcggcgg cggcggcggc cctataaaaa gcgaagcgcg cggcgggcgg gagtcgctgc  5340
gcgctgcctt cgccccgtgc cccgctccgc cgccgcctcg cccggccctg cccggctctg  5400
actgaccgcg ttactaaaac aggtaagtcc ggcctccgcg ccgggttttg gcgcctcccg  5460
cgggcgcccc cctcctcacg gcgagcgctg ccacgtcaga cgaagggcgc agcgagcgtc  5520
ctgatccttc cgcccggacg ctcaggacag cggcccgctg ctcataagac tcggccttag  5580
aaccccagta tcagcagaag gacattttag gacgggactt gggtgactct agggcactgg  5640
ttttctttcc agagagcgga acaggcgagg aaaagtagtc ccttctcggc gattctgcgg  5700
agggatctcc gtgggcggt gaacgccgat gatgcctcta ctaaccatgt tcatgttttc  5760
ttttttttc tacaggtcct gggtgacgaa cagggtaccg ccaccatggc caccggctct  5820
cgcacaagcc tgctgctggc tttcggacte ctgtgcctgc cttggcttca ggagggctcc  5880
gccgctagca tcgataccgt cgctatgtgc tggaggcttg ctgaaggctg tatgctggct  5940
cctccacttg gtggtttggt tttggcctct gactgacgcg gcaacattct ggtgattaca  6000
ggacacaagg cctgttacta gcactcacat ggaacaaatg gcctctagcc tggaggcttg  6060
ctgaaggctg tatgctgtca taatcgctat ttggtcggc gttttggcct ctgactgacg  6120
ccgcaccaaa gcgattatga caggacacaa ggcctgttac tagcactcac atggaacaaa  6180
tggcctctag cctggaggct tgctgaaggc tgtatgctgt tctgatcctg aagttcgggt  6240
tcgttttggc ctctgactga cgaacccgaa ccaggatcag aacaggacac aaggcctgtt  6300
actagcactc acatggaaca aatggcctct ctagaat  6337
```

```
SEQ ID NO: 22         moltype = DNA   length = 6339
FEATURE               Location/Qualifiers
source                1..6339
                      mol_type = other DNA
                      organism = synthetic construct
SEQUENCE: 22
aatcaacctc tggattacaa aatttgtgaa agattgactg gtattcttaa ctatgttgct  60
ccttttacgc tatgtggata cgctgcttta atgcctttgt atcatgctat tgcttcccgt  120
atggctttca ttttctcctc cttgtataaa tcctggttgc tgtctctttta tgaggagttg  180
tggcccgttg tcaggcaacg tggcgtggtg tgcactgtgt ttgctgacgc aaccccccact  240
ggttggggca ttgccaccac ctgtcagctc ctttccggga ctttcgcttt ccccctccct  300
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgc taagcttatc  600
gataccgtcg agatctaact tgtttattgc agcttataat ggttacaaat aaagcaatag  660
catcacaaat ttcacaaata aagcattttt ttcactgcat tctagttgtg tttgtccaa  720
actcatcaat gtatcttatc atgtctggat ctcgacctcg actagagcat ggctacgtag  780
ataagtagca tggcgggtta tcattaact acaaggaacc cctagtgatg gagttggcca  840
ctccctctct gcgcgctcgc tcgctcactg aggccgggcg accaaaggtc gcccgacgcc  900
cgggctttgc ccgggcggcc tcagtgagcg agcgagcgcg cagctggcgt aatagcgaag  960
aggcccgcac cgatcgccct tcccaacagt tgcgcagcct gaatggcgaa tggcgattcc  1020
gttgcaatgg ctggcggtaa tattgttctg gatattacca gcaaggccga tagtttgagt  1080
tcttctactc aggcaagtga tgttattact aatcaaagaa gtattgcgac aacggttaat  1140
ttgcgtgatg gacagactct tttactcggt ggcctcactg attataaaaa cacttctcag  1200
gattctggcg taccgttcct gtctaaaatc cctttaatcg gcctcctgtt tagctcccgc  1260
tctgattcta cgaggaaag cacgttatac gtgctcgtca aagcaaccat agtacgcgcc  1320
ctgtagcggc gcattaagcg cggcgggtgt ggtggttacg cgcagcgtga ccgctacact  1380
tgccagcgcc ctagcgcccg ctcctttcgc tttcttccct tcctttctcg ccacgttcgc  1440
cggctttccc cgtcaagctc taaatcgggg gctccctttag ggttccgat ttagtgcttt  1500
acggcaccctc gaccccaaaa aacttgatta gggtgatggt tcacgtagtg gccatcgcc  1560
ctgatagacg gtttttcgcc ctttgacgtt ggagtccacg ttctttaata gtggactctt  1620
gttccaaact ggaacaacac tcaacccat ctcggtctat tctttgatt tataagggat  1680
tttgccgatt tcggcctatt ggttaaaaaa tgagctgatt taacaaaaat ttaacgcgaa  1740
ttttaacaaa atattaacgt ttacaattta aatatttgct tatacaatct tcctgttttt  1800
```

-continued

```
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaaatat   1980
catattgatg gtgatttgac tgtctccggc ctttctcacc cgtttgaatc tttacctaca   2040
cattactcag gcattgcatt taaaatatat gagggttcta aaaattttta tccttgcgtt   2100
gaaataaagg cttctcccgc aaaagtatta cagggtcata atgttttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctattttat aggttaatgt   2520
catgataata atggtttctt agacgtcagg tggcactttt cggggaaatg tgcgcggaac   2580
ccctatttgt ttatttttct aaatacattc aaatatgtat ccgctcatga gacaataacc   2640
ctgataaatg cttcaataat attgaaaaag gaagagtatg agtattcaac atttccgtgt   2700
cgcccttatt cccttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
tttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggccttttt   4320
acggttcctg gccttttgct ggccttttgc tcacatgttc tttcctgcgt tatcccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgacccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgccccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tcccccccc   5100
ccccaccccc aattttgtat ttatttattt tttaattatt ttgtgcagcg atggggggcgg   5160
gggggggggg gggcgcgcgc caggcggggc ggggcggggc gaggggcggg gcggggcgag   5220
gcggagaggt gcggcggcag ccaatcagag cggcgcgctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg gcgagcgctg ccacgtcaga cgaagggcgc agcgagcgtc   5520
ctgatccttc cgcccggacg ctcaggacag cggcccgctg ctcataagac tcggccttag   5580
aaccccagta tcagcagaag gacattttag gacgggactt gggtgactct agggcactgg   5640
ttttctttcc agagagcgga acaggcgagg aaaagtagtc ccttctcggc gattctgcgg   5700
agggatctcc gtggggcggt gaacgccgat gatgcctcta ctaaccatgt tcatgttttc   5760
tttttttttc tacaggtcct gggtgacgaa cagggtaccg ccaccatggc caccggctct   5820
cgcacaagcc tgctgctggc tttcggactg ctgtgcctgc cttggcttca ggagggctct   5880
gccgctagca tcgataccgt cgctatgtgc tggaggcttg tcgaaggctg tatgctgaaa   5940
tcttccggtg gttccactgc gtttttggcct ctgactgacg cagtggaacc cggaagattt   6000
caggacacaa ggcctgttac tagcactcac atggaacaaa tggcctctag cctggaggct   6060
tgctgaaggc tgtatgctga tatcctgaat atggtatgca gcgttttggc ctctgactga   6120
cgctgcatac cattcaggat atcaggacac aaggcctgtt actagcactc acatggaaca   6180
aatggcctct agcctggagg cttgctgaag ctgtatgct gtttaaagct caaacgcgtt   6240
gccgtttttg gcctctgact gacggcgaac gcgtgagctt aaacaggac acaaggcctg   6300
ttactagcac tcacatggaa caaatggcct ctctagaat              6339
```

SEQ ID NO: 23      moltype = DNA  length = 6339
FEATURE            Location/Qualifiers -continued

```
source                  1..6339
                        mol_type = other DNA
                        organism = synthetic construct
SEQUENCE: 23
aatcaacctc tggattacaa aatttgtgaa agattgactg gtattcttaa ctatgttgct   60
cctttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccact   240
ggttgggggca ttgccaccac ctgtcagctc ctttccggga ctttcgcttt cccctcct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcatttt ttcactgcat tctagttgtg gtttgtccaa   720
actcatcaat gtatcttatc atgtctggat ctcgacctcg actagagcat ggctacgtag   780
ataagtagca tggcgggtta atcattaact acaaggaacc cctagtagtg gagttggcca   840
ctccctctct gcgcgctcgc tcgctcactg aggccgggcg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggc taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg ctccctttta gggttccgat ttagtgcttt   1500
acggcacctc gaccccaaaa aacttgatta gggtgatggt tcacgtagtg ggccatcgcc   1560
ctgatagacg gtttttcgcc ctttgacgtt ggagtccacg ttctttaata gtggactctt   1620
gttccaaact ggaacaacac tcaaccctat ctcggtctat tctttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt taaaatatat gagggttcta aaaattttta tccttgcgtt   2100
gaaataaagg cttctcccgc aaaagtatta cagggtcata atgtttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcactttt cggggaaatg tgcgcggaac   2580
ccctatttgt ttatttttct aaatacattc aaatatgtat ccgctcatga gacaataacc   2640
ctgataaatg cttcaataat attgaaaaag gaagagtatg agtattcaac atttccgtgt   2700
cgcccttatt ccctttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
tttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactact atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagatacctata cagcgtgagc tatgagaaag cgccacgctt cccgaaggga gaaaggcgga   4140
caggtatccg gtaagcggca gggtcggaac aggagagcgc acgagggagc ttccagggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggcctttt   4320
acggttcctg gccttttgct ggccttttgc tcacatgttc tttcctgcgt tatccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
```

-continued

```
tctccccgcg cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgaccccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgccccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tcccccccct   5100
ccccaccccc aattttgtat ttatttattt tttaattatt ttgtgcagcg atggggcgg   5160
gggggggggg gggcgcgcgc caggcggggc ggggcggggc gaggggcggg gcggggcgag   5220
gcggagaggt gcggcggcag ccaatcagag cggcgcgctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg gcgagcgctg ccacgtcaga cgaagggcgc agcgagcgtc   5520
ctgatccttc cgcccggacg ctcaggacag cggcccgctg ctcataagac tcggccttag   5580
aaccccagta tcagcagaag gacattttag gacgggactt gggtgactct agggcactgg   5640
ttttctttcc agagagcgga acaggcgagg aaaagtagtc ccttctcggc gattctgcgg   5700
agggatctcg gtggggcggt gaacgccgat gatgcctcta ctaaccatgt tcatgttttc   5760
ttttttttc tacaggtcct gggtgacgaa cagggtaccg ccaccatggc caccggctct   5820
cgcacaagcc tgctgctggc tttcggactg ctgtgcctgc cttggctcca ggagggctcc   5880
gccgctagca tcgataccgt cgctatgtgc tggaggcttg ctgaaggctg tatgctgtaa   5940
taaaggtctg ggaatcaccc gttttggcct ctgactgacg ggtgattccg acctttatta   6000
caggacacaa ggcctgttac tagcactcac atggaacaaa tggcctctag cctggaggct   6060
tgctgaaggc tgtatgctga aatacgccag atcaccatca gcgttttggc ctctgactga   6120
cgctgatggt gctggcgtat tacaggacac aaggcctgtt actagcactc acatggaaca   6180
aatgccctct agcctggagg cttgctgaag gctgtatgct gatacagaaa cgaaggttca   6240
ggccgttttg gcctctgact gacggcctga acccgtttct gtatcaggac acaaggcctg   6300
ttactagcac tcacatggaa caaatggcct ctctagaat                          6339
```

SEQ ID NO: 24                  moltype = DNA   length = 6339
FEATURE                        Location/Qualifiers
source                         1..6339
                               mol_type = other DNA
                               organism = synthetic construct
SEQUENCE: 24

```
aatcaacctc tggattacaa aatttgtgaa agattgactg gtattcttaa ctatgttgct   60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccccact   240
ggttggggca ttgccaccac ctgtcagctc ctttccgggt ctttcgcttt ccccctccct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcattttt ttcactgcat tctagttgtg gtttgtccaa   720
actcatcaat gtatcttatc atgtctggat ctcgacctcg actagagcat ggctacgtag   780
ataagtagca tggcgggtta atcattaact acaaggaacc cctagtgatg gagttggcca   840
ctccctctct gcgcgctcgc tcgctcactg aggccgggcg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggc taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg ctcccttta gggttccgat ttagtgcttt   1500
acggcacctc gaccccaaaa aacttgatta gggtgatggt tcacgtagtg ggccatcgcc   1560
ctgatagacg gtttttcgcc ctttgacgtt ggagtccacg ttctttaata gtggactctt   1620
gttccaaact ggaacaacac tcaaccctat ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt aaaaatatat gagggttcta aaaattttta tccttgcgtt   2100
gaaataaagg cttctcccgc aaaagtatta caggggtcata atgtttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
```

```
atcaccgaaa cgcgcgagac gaaagggcct cgtgatacgc ctattttat aggttaatgt  2520
catgataata atggtttctt agacgtcagg tggcactttt cggggaaatg tgcgcggaac  2580
ccctatttgt ttattttct aaatacattc aaatatgtat ccgctcatga gacaataacc  2640
ctgataaatg cttcaataat attgaaaaag gaagagtatg agtattcaac atttccgtgt  2700
cgcccttatt ccctttttg cggcattttg ccttcctgtt tttgctcacc cagaaacgct  2760
ggtgaaagta aaagatgctg aagatcagt gggtgcacga gtgggttaca tcgaactgga  2820
tctcaacagc ggtaagatcc ttgagagttt tcgccccgaa gaacgttttc caatgatgag  2880
cactttaaa gttctgctat gtggcgcggt attatcccgt attgacgccg ggcaagagca  2940
actcggtcgc cgcatacact attctcagaa tgacttggtt gagtactcac cagtcacaga  3000
aaagcatctt acggatggca tgacagtaag agaattatgc agtgctgcca taaccatgag  3060
tgataacact gcggccaact tacttctgac aacgatcgga ggaccgaagg agctaaccgc  3120
tttttgcac aacatggggg atcatgtaac tcgccttgat cgttgggaac cggagctgaa  3180
tgaagccata ccaaacgacg agcgtgacac cacgatgcct gtagcaatgg caacaacgtt  3240
gcgcaaacta ttaactggcg aactacttac tctagcttcc cggcaacaat taatagactg  3300
gatggaggcg gataaagttg caggaccact tctgcgctcg gcccttccgg ctggctggtt  3360
tattgctgat aaatctggag ccggtgagcg tgggtctcgc ggtatcattg cagcactggg  3420
gccagatggt aagccctccc gtatcgtagt tatctacacg acggggagtc aggcaactat  3480
ggatgaacga aatagacaga tcgctgagat aggtgcctca ctgattaagc attggtaact  3540
gtcagaccaa gtttactcat atatacttta gattgattta aaacttcatt tttaatttaa  3600
aaggatctag gtgaagatcc tttttgataa tctcatgacc aaaatccctt aacgtgagtt  3660
ttcgttccac tgagcgtcag accccgtaga aaagatcaaa ggatcttctt gagatccttt  3720
ttttctgcgc gtaatctgct gcttgcaaac aaaaaaacca ccgctaccag cggtggtttg  3780
tttgccggat caagagctac caactctttt tccgaaggta actggcttca gcagagcgca  3840
gataccaaat actgtccttc tagtgtagcc gtagttaggc caccacttca agaactctgt  3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg ggggggttcgt gcacacagcc cagcttggag cgaacgacct acaccgaact  4080
gagataccta cagcgtgagc tatgagaaag cgccacgctt cccgaaggga gaaaggcgga  4140
caggtatccg gtaagcggca gggtcggaac aggagagcgc acgagggagc ttccaggggg  4200
aaacgcctgg tatctttata gtcctgtcgg gtttcgccac ctctgacttg agcgtcgatt  4260
tttgtgatgc tcgtcagggg ggcggagcct atggaaaaac gccagcaacg cggcctttt  4320
acggttcctg gccttttgct ggccttttgc tcacatgttc tttcctgcgt tatcccctga  4380
ttctgtggat aaccgtatta ccgcctttga gtgagctgat accgctcgcc gcagccgaac  4440
gaccgagcgc agcgagtcag tgagcgagga agcggaagag cgcccaatac gcaaaccgcc  4500
tctccccgcg cgttggccga ttcattaatg cagcagctgc gcgctcgctc gctcactgac  4560
gccgcccggg caaagcccgg gcgtcgggcg accttggtc gcccggcctc agtgagcgag  4620
cgagcgcgca gagagggagt ggccaactcc atcactaggg gttccttgta gttaatgatt  4680
aacccgccat gctacttatc tacgtagcca tgctctagga cattgattat tgactagtgg  4740
agttccgcgt tacataactt acggtaaatg gcccgcctgg cctgaccgcc aacgaccccc  4800
gcccattgac gtcaataatg acgtatgttc ccatagtaac gccaataggg actttccatt  4860
gacgtcaatg ggtggagtat ttacggtaaa ctgcccactt ggcagtacat caagtgtatc  4920
atatgccaag tacgccccct attgacgtca atgacggtaa atggcccgcc tggcattatg  4980
cccagtacat gaccttatgg gactttccta cttggcagta catctacgta ttagtcatcg  5040
ctattaccat ggtcgaggtg agccccacgt tctgcttcac tctccccatc tcccccccct  5100
ccccacccc aattttgtat ttatttattt tttaattatt ttgtgcagcg atggggggcgg  5160
gggggggggg gggcgcgcgc caggcggggc ggggcggggc gaggggcggg gcggggcgag  5220
gcggagaggt gcggcggcag ccaatcagag cggcgcgctc cgaaagtttc cttttatggc  5280
gaggcggcgg cggcggcggc cctataaaaa gcgaagcgcg cggcgggcgg gagtcgctgc  5340
gcgctgcctt cgccccgtgc cccgctccgc cgccgcctcg cgccgcccgc cccggctctg  5400
actgaccgcg ttactaaaac aggtaagtcc ggcctccgcg ccgggttttg gcgcctcccg  5460
cgggcgcccc cctcctcacg gcgagcgctg ccacgtcaga cgaagggcgc agcgagcgtc  5520
ctgatccttc cgcccggacg ctcaggacag cggcccgctg ctcataagac tcggccttag  5580
aaccccagta tcagcagaag gacattttag gacgggactt gggtgactct agggcactgg  5640
ttttctttcc agagagcgga acaggcgagg aaaagtagtc ccttctcggc gattctgcgg  5700
agggatctcc gtggggcggt gaacgccgat gatgcctcta ctaaccatgt tcatgttttc  5760
ttttttttc tacaggtcct gggtgacgaa cagggtaccg ccaccatggc caccggctct  5820
cgcacaagcc tgctgctggc tttcggactc ctgtgcctgc cttggctcca ggaggctcc  5880
gccgctagca tcgataccgt cgctatgtgc tggaggcttg ctgaaggctg tatgctgtca  5940
gatcgctgtg gtaaacaggc gttttggcct ctgactgacg cctgtttacc agcgatctga  6000
caggacacaa ggcctgttac tagcactcac atggaacaat tggcctctag cctggaggct  6060
tgctgaaggc tgtatgctga gaatcagatc agatagcgat ccgtttttggc ctctgactga  6120
cggatcgcta tctgctgatt ctcaggcaca aaggcctgtt actagcactc acatggaaca  6180
aatggcctct agcctggagg cttgctgaag gctgtatgct gaaacatgcc aacagcagaa  6240
tgccgttttg gcctctgact gacggcattc tgctgggcat gtttcaggac acaaggcctg  6300
ttactagcac tcacatggaa caaatggcct ctctagaat                          6339
```

```
SEQ ID NO: 25          moltype = DNA   length = 6339
FEATURE                Location/Qualifiers
source                 1..6339
                       mol_type = other DNA
                       organism = synthetic construct
SEQUENCE: 25
aatcaacctc tggattacaa aatttgtgaa agattgactg gtattcttaa ctatgttgct   60
cctttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aaccccact  240
ggttggggca ttgccaccac ctgtcagctc ctttccggga ctttcgcttt ccccctccct  300
attccacgtg cggaactcat cgccgcctgc cttgcccgct gctggacagg ggctcggctg  360
ttgggcactg acaattccgt ggtgttgtcg gggaaatcat cgtcctttcc ttggctgctc  420
```

```
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc taagcttatc    600
gataccgtcg agatctaact tgtttattgc agcttataat ggttacaaat aaagcaatag    660
catcacaaat ttcacaaata aagcattttt ttcactgcat tctagttgtg gtttgtccaa    720
actcatcaat gtatcttatc atgtctggat ctcgacctcg actagagcat ggctacgtag    780
ataagtagca tggcgggtta atcattaact acaaggaacc cctagtgatg gagttggcca    840
ctccctctct gcgcgctcgc tcgctcactg aggccgggcg accaaaggtc gcccgacgcc    900
cgggctttgc ccgggcggcc tcagtgagcg agcgagcgcg cagctggcgt aatagcgaag    960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggcg taccgttcct gtctaaaatc cctttaatcg gcctcctgtt tagctccgac   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg gctcccttta gggttccgat ttagtgcttt   1500
acggcacctc gaccccaaaa aacttgatta gggtgatggt tcacgtagtg ggccatcgcc   1560
ctgatagacg gtttttcgcc ctttgacgtt ggagtccacg ttctttaata gtggactctt   1620
gttccaaact ggaacaacac tcaaccctat ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta atatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt taaaatatat gagggttcta aaaatttta tccttgcgtt   2100
gaaataaagg cttctcccgc aaaagtatta cagggtcata atgtttttgg tacaaccgat   2160
ttagctttat gctctgaggc tttattgctt aattttgcta attctttgcc ttgcctgtat   2220
gatttattgg atgttggaat tcctgatgcg gtatttttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcactttt cggggaaatg tgcgcggaac   2580
ccctatttgt ttatttttct aaatacattc aaatatgtat ccgctcatga gacaataacc   2640
ctgataaatg cttcaataat attgaaaaag gaagagtatg agtattcaac atttccgtgt   2700
cgcccttatt ccctttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
tttttttcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga aaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggccttttt   4320
acggttcctg gccttttgct ggccttttgc tcacatgttc tttcctgcgt tatcccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctcg cgctcgctc gctcactgag   4560
gccgcccggg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgacccccc   4800
gcccattgac gtcaataatg acgtatgttc ccatagtaac gccaataggg actttccatt   4860
gacgtcaatg gtggagtat ttacggtaaa ctgcccactt ggcagtacat caagtgtatc   4920
atatgccaag tacgccccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tcccccccct   5100
cccacccccc aattttgtat ttatttattt tttaattatt ttgtgcagcg atggggggcgg   5160
```

-continued

```
gggggggggg gggcgcgcgc caggcggggc ggggcggggc gaggggcggg gcggggcgag   5220
gcggagaggt gcggcggcag ccaatcagag cggcgcgctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg gcgagcgctg ccacgtcaga cgaagggcgc agcgagcgtc   5520
ctgatccttc cgcccggacg ctcaggacag cggcccgctg ctcataagac tcggccttag   5580
aaccccagta tcagcagaag gacattttag gacgggactt gggtgactct agggcactgg   5640
ttttctttcc agagagcgga acaggcgagg aaaagtagtc ccttctcggc gattctgcgg   5700
agggatctcc gtggggcggt gaacgccgat gatgcctcta ctaaccatgt tcatgttttc   5760
tttttttttc tacaggtcct gggtgacgaa cagggtaccg ccaccatggc caccggctct   5820
cgcacaagcc tgctgctggc tttcggactg ctgtgcctgc cttggctcca ggagggctcc   5880
gccgctagca tcgataccgt cgctatgtgc tggaggcttg ctgaaggctg tatgctgaca   5940
atcagatatg gttgctcggc gttttggcct ctgactgacg ccgagcaact atctgattgt   6000
caggacacaa ggcctgttac tagcactcac atggaacaaa tggcctctag cctggaggct   6060
tgctgaaggc tgtatgctgt ttcacaatgc atcgttcagc gcgttttggc ctctgactga   6120
cgcgctgaac ggcattgtga aacaggacac aaggcctgtt actagcactc acatggaaca   6180
aatggcctct agcctggagg cttgctgaag gctgtatgct gacaataatg ccaacagggt   6240
ggtcgttttg gcctctgact gacgaccacc ctgggcatta ttgtcaggac acaaggcctg   6300
ttactagcac tcacatggaa caaatggcct ctctagaat                          6339
```